(12) United States Patent
Gagnon et al.

(10) Patent No.: US 11,267,779 B2
(45) Date of Patent: *Mar. 8, 2022

(54) SUBSTITUTED AROMATIC COMPOUNDS FOR THE TREATMENT OF PULMONARY FIBROSIS, LIVER FIBROSIS, SKIN FIBROSIS AND CARDIAC FIBROSIS

(71) Applicant: PROMETIC PHARMA SMT LIMITED, Cambridge (GB)

(72) Inventors: Lyne Gagnon, Laval (CA); Pierre Laurin, Ville Mont-Royal (CA); Brigitte Grouix, Montreal (CA); Lilianne Geerts, St-Lazare (CA); François Sarra-Bournet, Laval (CA); Martin Leduc, Laval (CA)

(73) Assignee: PROMETIC PHARMA SMT LIMITED, Cambridge (GB)

(*) Notice: Subject to any disclaimer, the term of this patent is extended or adjusted under 35 U.S.C. 154(b) by 35 days.

This patent is subject to a terminal disclaimer.

(21) Appl. No.: 16/580,747

(22) Filed: Sep. 24, 2019

(65) Prior Publication Data
US 2020/0017432 A1    Jan. 16, 2020

Related U.S. Application Data

(63) Continuation of application No. 15/852,977, filed on Dec. 22, 2017, now Pat. No. 10,450,258, which is a
(Continued)

(51) Int. Cl.
| | |
|---|---|
| *C07C 57/30* | (2006.01) |
| *A61K 31/192* | (2006.01) |
| *C07C 57/58* | (2006.01) |
| *C07C 59/52* | (2006.01) |
| *A61K 31/4418* | (2006.01) |
| *A61K 45/06* | (2006.01) |
| *C07C 57/42* | (2006.01) |
| *C07C 57/60* | (2006.01) |
| *C07C 59/84* | (2006.01) |

(52) U.S. Cl.
CPC ............ *C07C 57/30* (2013.01); *A61K 31/192* (2013.01); *A61K 31/4418* (2013.01); *A61K 45/06* (2013.01); *C07C 57/42* (2013.01); *C07C 57/58* (2013.01); *C07C 57/60* (2013.01); *C07C 59/52* (2013.01); *C07C 59/84* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 9,884,802 B2* | 2/2018 | Gagnon | A61K 31/192 |
| 10,023,518 B2* | 7/2018 | Zacharie | A61P 43/00 |

(Continued)

FOREIGN PATENT DOCUMENTS

| | | |
|---|---|---|
| WO | 03043625 A1 | 5/2003 |
| WO | 2010127440 A1 | 11/2010 |

(Continued)

OTHER PUBLICATIONS

Kusunose, M. et al., "Effect of Sho-saiko-to Extract on Hepatic Inflammation and Fibrosis in Dimethylnitrosamine Induced Liver Injury Rats." Biol. Pharm. Bull., 2002, 25 (11): 1417-1421.
Liu, X. et al., "Therapeutic strategies against TGF-β signaling pathway in hepatic fibrosis." Liver International, 2006, 26: 8-22.
Moriconi, A. et al., "Design of noncompetitive interleukin-8 inhibitors acting on CXCR1 and CXCR2." J. Med. Chem., Aug. 2007, 50 (17): Abstract.

(Continued)

*Primary Examiner* — Jeffrey S Lundgren
*Assistant Examiner* — Michael J Schmitt
(74) *Attorney, Agent, or Firm* — Saliwanchik, Lloyd & Eisenschenk

(57) ABSTRACT

The present invention relates to substituted aromatic compounds for use in prevention or treatment of various fibrotic diseases and conditions in subjects, including pulmonary fibrosis, liver fibrosis, skin fibrosis and cardiac fibrosis, where the compound has the following formula:

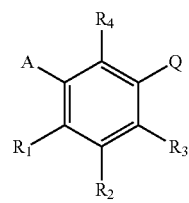

or a pharmaceutically acceptable salt thereof, wherein

A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4;

$R_1$ is H, OH or F;

$R_2$ is H, OH, F or $CH_2$—OH;

$R_3$ is H, OH, F or $CH_2Ph$;

$R_4$ is H, OH or F;

Q is

1) $(CH_2)_mC(O)OH$ wherein m is 1 or 2,
2) $CH(CH_3)C(O)OH$,
3) $C(CH_3)_2C(O)OH$,
4) $CH(F)$—$C(O)OH$,
5) $CF_2$—$C(O)OH$, or
6) $C(O)$—$C(O)OH$.

19 Claims, 18 Drawing Sheets

Related U.S. Application Data continuation of application No. 14/775,882, filed as application No. PCT/CA2014/000237 on Mar. 14, 2014, now Pat. No. 9,884,802.

(60) Provisional application No. 61/798,427, filed on Mar. 15, 2013.

(56) References Cited

U.S. PATENT DOCUMENTS

| 10,391,073 B2* | 8/2019 | Gagnon | A61K 8/365 |
| 10,450,258 B2* | 10/2019 | Gagnon | C07C 57/30 |

FOREIGN PATENT DOCUMENTS

| WO | 2010127448 A1 | 11/2010 | |
| WO | WO-2010127440 A1 * | 11/2010 | A61P 3/06 |
| WO | 2012097427 A1 | 7/2012 | |

OTHER PUBLICATIONS

Peters-Golden, M., "Arachidonic Acid Metabolites: Potential Mediators and Therapeutic Targets in Fibrotic Lung Disease." University of Michigan Health System, Ann Arbor, Michigan, U.S.A., Iopathic Pulmonary Fibrosis, edited by Joseph P. Lynch, CRC Press, 2003, 419-449.

Schaefer, C. J. et al., "Antifibrotic activities of pirfenidone in animal models." European Respiratory Review, 2011, 20 (120): 85-97.

Thrall, R. S. et al., "Bleomycin-Induced Pulmonary Fibrosis in the Rat: Inhibition by Indomethacin." American Journal of Pathology, Apr. 1979, 95 (1): 117-130.

* cited by examiner

Compound I (iv and po) reduces heart lesions in catheterized 5/6-nephrectomized rats.

Compound I (iv and po) reduces heart inflammation in catheterized 5/6-nephrectomized rats

Compound I (iv and po) reduces heart necrosis in catheterized 5/6-nephrectomized rats

Compound I (iv and po) reduces hydroxyproline (collagen) content in catheterized 5/6-nephrectomized rats

Decrease in interstitial fibrosis in Compound I-treated catheterized 5/6-Nx rats, as demonstrated by Masson's trichrome staining

Decrease in interstitial fibrosis in Compound I-treated catheterized 5/6-Nx rats, as demonstrated by Masson's trichrome staining

Decrease in interstitial fibrosis in Compound I-treated catheterized 5/6-Nx rats, as demonstrated by Masson's trichrome staining

SUBSTITUTED AROMATIC COMPOUNDS FOR THE TREATMENT OF PULMONARY FIBROSIS, LIVER FIBROSIS, SKIN FIBROSIS AND CARDIAC FIBROSIS

CROSS REFERENCE TO RELATED APPLICATIONS

This application is a continuation of co-pending application Ser. No. 15/852,977, filed Dec. 22, 2017; which is a continuation of application Ser. No. 14/775,882, filed Sep. 14, 2015 (now U.S. Pat. No. 9,884,802); which is a National Stage Application of International Application Number PCT/CA2014/000237, filed Mar. 14, 2014; which claims the benefit of U.S. Provisional Application No. 61/798,427, filed Mar. 15, 2013; all of which are incorporated herein by reference in their entirety.

FIELD OF INVENTION

The present invention relates to substituted aromatic compounds, their preparation, compositions comprising the same and their use for prevention or treatment of various fibrotic diseases and conditions in subjects, including pulmonary fibrosis, liver fibrosis, skin fibrosis and cardiac fibrosis.

BACKGROUND OF INVENTION

Pulmonary Fibrosis

Lung fibrosis, also referred to as pulmonary fibrosis, is a serious medical condition that involves scarring of the lung tissue. This condition occurs when the alveoli and interstitial tissue of the lungs become inflamed and develop scars on the tissue in an attempt to repair themselves. Pulmonary fibrosis involves gradual exchange of normal lung parenchyma with fibrotic tissue (fibrous scar). The replacement of normal lung with scar tissue causes irreversible decrease in oxygen diffusion capacity. Currently, there is no cure or means by which to reverse this scarring of the lung tissue.

Pulmonary fibrosis can be caused by many conditions which includes chronic inflammatory processes (sarcoidosis, Wegener's granulomatosis), infections, environmental agents (asbestos, silica, exposure to certain gases), exposure to ionizing radiation (such as radiation therapy to treat tumors of the chest), chronic conditions (lupus), and certain medications (e.g. amiodarone, bleomycin, pingyangmycin, busulfan, methotrexate, and nitrofurantoin).

In a condition known as hypersensitivity pneumonitis, fibrosis of the lung can develop following a heightened immune reaction to inhaled organic dusts or occupational chemicals. This condition most often results from inhaling dust contaminated with bacterial, fungal, or animal products.

COPD (chronic obstructive pulmonary disease) is another form of lung fibrosis (Gosker et al. (2003) "Myopathological features in skeletal muscle of patients with chronic obstructive pulmonary disease" Eur. Respir. J. 22(2), 280-285) that is caused by smoke irritation of the lung tissue. Tobacco smoking is the most common cause of COPD, with a number of other factors such as air pollution and genetics playing a smaller role. In the developing world, one of the common sources of air pollution is from poorly vented cooking and heating fires. Long-term exposure to these irritants causes an inflammatory response in the lungs resulting in narrowing of the small airways and breakdown of lung tissue known as emphysema. The diagnosis is based on poor airflow as measured by lung function tests. In contrast to asthma, the airflow reduction does not improve significantly with the administration of currently approved medications. COPD can be prevented by reducing exposure to the known causes. This includes efforts to decrease rates of smoking and to improve indoor and outdoor air quality. COPD treatments include: quitting smoking, vaccinations, rehabilitation, and often inhaled bronchodilators and steroids. Some people may benefit from long-term oxygen therapy or lung transplantation. In those who have periods of acute worsening, increased use of medications and hospitalization may be needed.

Cystic fibrosis (CF) is also another form of lung fibrosis. CF is an autosomal recessive genetic disorder that affects most critically the lungs, and also the pancreas, liver, and intestine. It is characterized by abnormal transport of chloride and sodium across an epithelium, leading to thick, viscous secretions. The name cystic fibrosis refers to the characteristic scarring (fibrosis) and cyst formation within the pancreas, first recognized in the 1930s. Difficulty breathing is the most serious symptom and results from frequent lung infections that are treated with antibiotics and other medications. Other symptoms (including sinus infections, poor growth, and infertility) affect other parts of the body. CF is caused by a mutation in the gene for the protein cystic fibrosis transmembrane conductance regulator (CFTR). This protein is required to regulate the components of sweat, digestive fluids, and mucus. CFTR regulates the movement of chloride and sodium ions across epithelial membranes, such as the alveolar epithelia located in the lungs. Most people without CF have two working copies of the CFTR gene, and both copies must be missing for CF to develop, due to the disorder's recessive nature. CF develops when neither copy works normally (as a result of mutation) and therefore has autosomal recessive inheritance. Studies in mast cells in cystic fibrosis and idiopathic pulmonary fibrosis, diseases that have peripheral lung fibrosis as a significant pathological feature (Andersson et. al. (2011) "Activated MC(TC) mast cells infiltrate diseased lung areas in cystic fibrosis and idiopathic pulmonary fibrosis" Respiratory Research 12(1), 139). Although CF and IPF have different etiologies, the basic pathological features of the fibrotic lesions include excessive collagen deposition.

In some subjects, chronic pulmonary inflammation and fibrosis develop without an identifiable cause. Most of these subjects have a condition called idiopathic pulmonary fibrosis (IPF). IPF is a chronic progressive pulmonary fibrosis of unknown etiology. Prednisone is the usual treatment for IPF but it can be treated with other immunosuppressive therapies with the objective of reduction of inflammation that is the prelude to lung fibrosis. Although prednisone has a modest measurable effect on improving lung function, the scarce evidence for its long-term efficacy, as well as concerns regarding its safety, limits its use. Indeed most immunosuppressive drugs have little therapeutic effects and lung transplantation may be necessary. Unfortunately, transplants are of limited success in patients with end-stage long disease and median survival time with patients is four to six years after diagnosis. As such, there is need for novel yet efficacious treatment for IPF.

Some clinical trials are ongoing with candidate drugs that specifically address the inhibition or slowing down of fibrosis in the lungs such as IFN-γ and mycophenolate mofetil. Further examples include: pirfenidone which mechanism of action is not well defined but seems to reduce CTGF and has shown some results in clinical phase; substituted biphenyl carboxylic acids which function as lysophosphatidic acid receptor antagonists and display significant antifibrotic activity in the standard pulmonary fibrosis mouse model (bleomycin-induced lung fibrosis). As such, this compound is reported to be in clinical trials for the treatment of IPF. Inhibition of protein kinase enzymes with orally active candidate drugs or treatment with orally active antioxidants provide two treatment approaches for pulmonary fibrosis: multiple kinase inhibitors (such as nintedanib) and JNK (kinase) inhibitors (such as tanzisertib). Also, drug candidates for IPF includes antioxidant N-acetylcysteine. However, to date the progress of protein kinase inhibitors and antioxidants have been questionable for the treatment of IPF due to issues of toxicity and/or efficacy. Protein kinase enzymes and associated receptors are ubiquitous amongst normal and diseased cell populations and so inhibition may result in toxicity arising in particular amongst rapidly proliferating cell populations.

Additionally, clinical trials are in progress with monoclonal antibodies that target different profibrotic proteins (cytokines (CTGF, TGF-β, MCP-1, IL-4 and IL-13), integrins (αvβ6) and enzymes (LOXL2 enzyme) for the treatment of IPF. However, a number of issues are associated with the development and use of monoclonal antibodies for the treatment of IPF (which apply to other recombinant proteins) which include toxicity (including protein immunogenicity), difficulty of manufacture (batch consistency, scale-up, expense) and administration (need for refrigeration, not orally active).

Furthermore, though research trials are ongoing, there is no evidence that any medications can significantly help this condition. Lung transplantation is the only therapeutic option available in severe cases. Unfortunately, transplants are of limited success in patients with end-stage lung disease. As such, there is a need for novel yet efficacious treatments for IPF. Therefore, there is a need for novel yet conveniently administered (orally active) efficacious synthetic (readily manufactured) compounds.

Liver Fibrosis

Liver fibrosis or hepatic fibrosis is the excessive accumulation of extracellular matrix proteins (including collagen), and subsequent scarring process, that occurs in most chronic liver diseases. With time, advanced liver fibrosis results in cirrhosis of the liver. Cirrhosis is the final phase of the chronic liver disease and is generally irreversible with a poor long-term prognosis. In the advanced stage, the only option is the liver transplant. The risk of liver cancer is significant increased with cirrhosis and cirrhosis may be viewed as a premalignant condition (hepatocellular carcinoma). Indeed, cirrhosis and liver cancer are among the ten causes of death worldwide. As such, there is a need for novel yet efficacious treatment for liver fibrosis and subsequent cirrhosis of the liver. Unfortunately, few treatment options are available and most often treatment consists of addressing the causes and/or symptoms of liver cirrhosis. No treatment will cure liver fibrosis subsequent scarring and cirrhosis. Liver transplantation is the only treatment available for patients with advanced stage of fibrosis. Therefore, alternative methods that would be less intrusive are needed to cure, treat, slow the progression of, or prevent liver fibrosis.

Accumulation of fluid in the abdomen (ascites) is a common problem associated with liver cirrhosis. Treatment options include a low sodium diet, diuretics and removal of fluid by insertion of a needle into the abdominal cavity (paracentesis). Cirrhosis of the liver is caused by alcohol abuse, viral hepatitis (B, C and D), non-alcoholic fatty liver disease (NAFLD) associated with obesity, diabetes, protein malnutrition, coronary artery disease, corticosteroids, auto-immune hepatitis, inherited diseases (cystic fibrosis, alpha-1-antitrypsin deficiency, etc), primary biliary cirrhosis, drug reaction and exposure to toxins.

A limited number of clinical trials are in progress with candidate drugs that specifically address the inhibition or slowing down of fibrosis in the liver. However, these trials target specific liver disease such as NASH (Non-alcoholic Steatohepatitis). NASH refers to a combination of fatty liver (NAFLD) with inflammation and occurs in individuals who drink little or no alcohol. Cysteamine is a precursor of the potent liver antioxidant glutathione and increased in vivo production of glutathione is believed to offer improvement of NASH-related liver disease. As such, cysteamine is under evaluation in clinical trial in pediatric patients with NASH. Other antioxidants are under evaluation such as vitamin E and selenium but their effectiveness for the treatment of NASH is unknown. Also under evaluation for the treatment of NASH is the use of anti-diabetic drug even in patients without diabetes. This approach addresses the fact that most NASH patients have insulin resistance. Once again, there is a need for novel yet conveniently administered (orally active) efficacious compound for the treatment of liver fibrosis, subsequent scarring and liver cirrhosis.

Skin Fibrosis

Skin fibrosis or dermal fibrosis is excessive scarring of the skin, and is a result of a pathologic wound healing response. There is a wide spectrum of fibrotic skin diseases: scleroderma, nephrogenic fibrosing dermopathy, mixed connective tissue disease, scleromyxedema, scleredema, and eosinophilic fasciitis. Exposures to chemicals or physical agents (mechanical trauma, burn wounds) are also potential causes of fibrotic skin disease. Dermal fibrosis may be driven by immune, autoimmune, and inflammatory mechanisms. The balance of collagen production and degradation by fibroblasts plays a critical role in the pathophysiology of fibrotic processes in the skin. Certain cytokines promote would healing and fibrosis, such as transforming growth factor-β (TGF-β) and interleukin-4 (IL-4), whereas others are antifibrotic, such as interferon-γ (IFN-γ) and tumor necrosis factor-α (TNF-α). Fibroblasts of normal skin are quiescent. They synthesize controlled amounts of connective tissue proteins and have low proliferative activity. Following skin injury, these cells become activated, i.e. they proliferate, express α-smooth muscle actin (α-SMA) and synthesize large amounts of connective tissue proteins. The activated cells are often called myofibroblasts.

Scar formation as part of the wound healing process and which accompanies fibrosis is particularly undesired from a cosmetic perspective during skin fibrosis, especially when the scars are formed on the face and/or other exposed parts of the body. Scleroderma refers to skin fibrosis; sclera means hard and derma means skin. However, skin fibrosis may have important health consequences, especially if it is part of systemic scleroderma. The latter refers to a connective tissue disease of auto-immune etiology. Whereas limited cutaneous scleroderma is restricted to skin on the face and on feet, diffuse cutaneous scleroderma covers more of the skin and may progress to the visceral organs.

The most popular approach for treating skin fibrosis is the use of immunosuppressive therapy. The rationale is that the auto-immune etiology is responsible for the inflammation aspect of the disease along with subsequent tissue damage and fibrosis. Studied drugs include methotrexate, mycophenolate, mofetil, cyclophosphamide and cyclosporine. Although some improvement has been observed with immunosuppressive therapy, concerns regarding drug safety along with a lack of definitive clinical data and demonstrable efficacy, remain.

There is a need to develop efficacious pharmaceutical preparation for treating skin fibrosis, fibrotic skin diseases and pathological scarring of the skin.

Cardiac Fibrosis

Cardiac fibrosis, a hallmark of heart disease, is thought to contribute to sudden cardiac death, ventricular tachyarrhythmia, left ventricular (LV) dysfunction, and heart failure. Cardiac fibrosis is characterized by a disproportionate accumulation of fibrillated collagen that occurs after myocyte death, inflammation, enhanced workload, hypertrophy, and stimulation by a number of hormones, cytokines, and growth factors.

Cardiac fibrosis may also refer to an abnormal thickening of the heart valves due to inappropriate proliferation of cardiac fibroblasts but more commonly refers to the proliferation of fibroblasts in the cardiac muscle. Fibrocyte cells normally secrete collagen, and function to provide structural support for the heart. When over-activated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

The most obvious treatment for cardiac valve fibrosis or fibrosis in other locations, consists of stopping the stimulatory drug or production of serotonin. Surgical tricuspid valve replacement for severe stenosis (blockage of blood flow) has been necessary in some patients. Also, a compound found in red wine, resveratrol, has been found to slow the development of cardiac fibrosis. [Olson et al. (2005) "Inhibition of cardiac fibroblast proliferation and myofibroblast differentiation by resveratrol". American journal of physiology. Heart and circulatory physiology 288 (3): H1131-8; Aubin, et al. (2008) "Female rats fed a high-fat diet were associated with vascular dysfunction and cardiac fibrosis in the absence of overt obesity and hyperlipidemia: Therapeutic potential of resveratrol". The Journal of Pharmacology and Experimental Therapeutics 325 (3): 961-8. More sophisticated approaches of countering cardiac fibrosis like microRNA inhibition (miR-21, for example) are being tested in animal models.

No medication is on the market to prevent or treat cardiac fibrosis and there is a need to develop efficacious pharmaceutical preparation.

SUMMARY OF THE INVENTION

Surprisingly, the inventors have determined that the compounds of the present invention display antifibrotic activity in the lungs, liver, skin and heart. Knowing that the compounds of the present invention have a good safety profile; the inventors concluded that the compounds of the present invention are excellent drug candidates for the prevention/treatment of pulmonary fibrosis, liver fibrosis, skin fibrosis and cardiac fibrosis. Cardiac fibrosis and heart fibrosis are interchangeably used herein and are intended to designate the same.

More particularly, the present invention concerns a method for preventing and/or slowing progression of and/or treating a fibrotic disease in a subject in need thereof. The fibrotic disease is pulmonary fibrosis, liver fibrosis, skin fibrosis or cardiac fibrosis. The method comprises the administration of a therapeutically effective amount of a compound represented by the formula:

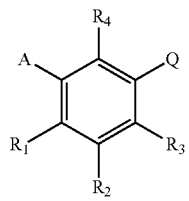

or a pharmaceutically acceptable salt thereof, wherein

A is $C_5$ alkyl, $C_6$ alkyl, $C_5$ alkenyl, $C_6$ alkenyl, $C(O)$—$(CH_2)_n$—$CH_3$ or $CH(OH)$—$(CH_2)_n$—$CH_3$ wherein n is 3 or 4; or is preferably $C_5$ alkyl, $C_5$ alkenyl, $C(O)$—$(CH_2)_n$—$CH_3$ or $CH(OH)$—$(CH_2)_n$—$CH_3$ wherein n is 3; or is preferably $C_6$ alkyl, $C_6$ alkenyl, $C(O)$—$(CH_2)_n$—$CH_3$ or $CH(OH)$—$(CH_2)_n$—$CH_3$ wherein n is 4;

$R_1$ is H, OH or F; or is preferably H or OH;

$R_2$ is H, OH, F or $CH_2$—OH; or is preferably H, OH or F; or is preferably H or OH;

$R_3$ is H, OH, F or $CH_2Ph$; or is preferably H, OH or F; or is preferably H or OH;

$R_4$ is H, OH or F; or is preferably H or OH;

Q is

1) $(CH_2)_mC(O)OH$ wherein m is 1 or 2,
2) $CH(CH_3)C(O)OH$,
3) $C(CH_3)_2C(O)OH$,
4) $CH(F)$—$C(O)OH$,
5) $CF_2$—$C(O)OH$, or
6) $C(O)$—$C(O)OH$.

In a preferred embodiment, the pharmaceutically acceptable salt of the compound is sodium, potassium, lithium, ammonium, calcium, magnesium, manganese, zinc, iron, or copper. The preferred pharmaceutically acceptable salt of the compound is sodium.

According to a preferred embodiment of the invention, the compound is one of the following compounds:

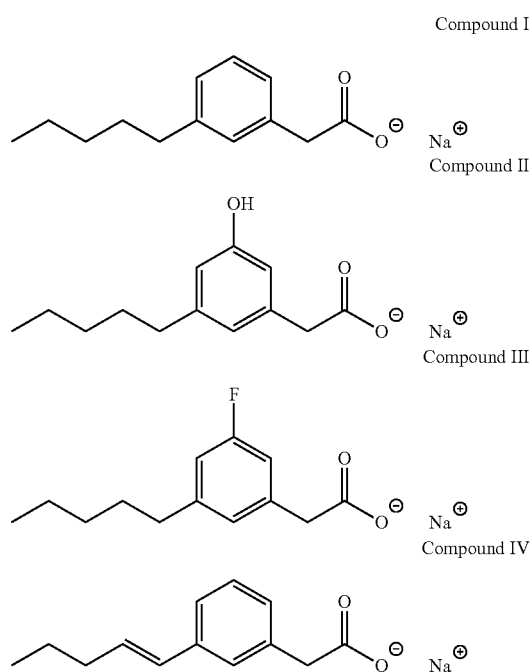

Compound V
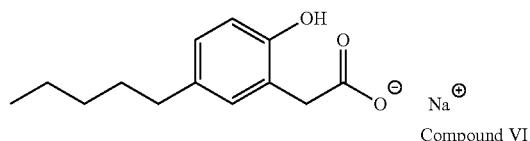

Compound VI
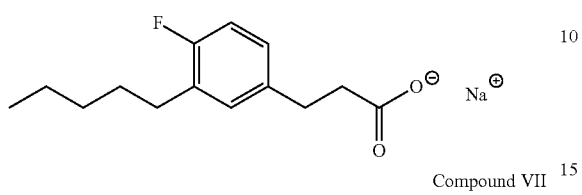

Compound VII
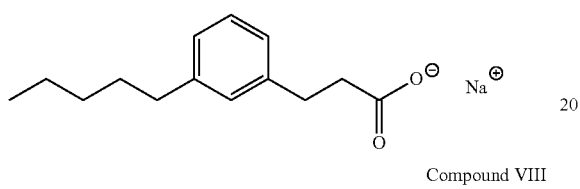

Compound VIII
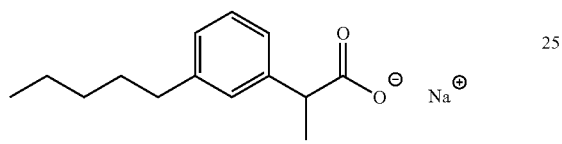

Compound IX
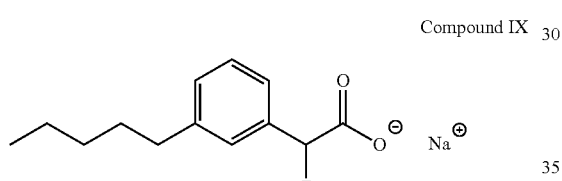

Compound X
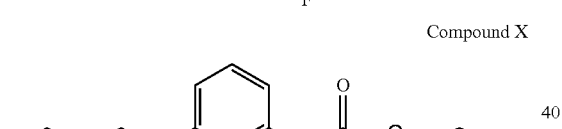

Compound XI
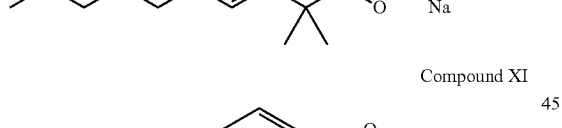

Compound XII
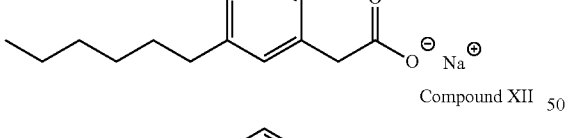

Compound XIII
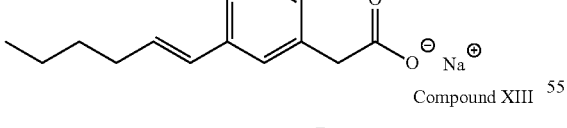

Compound XIV
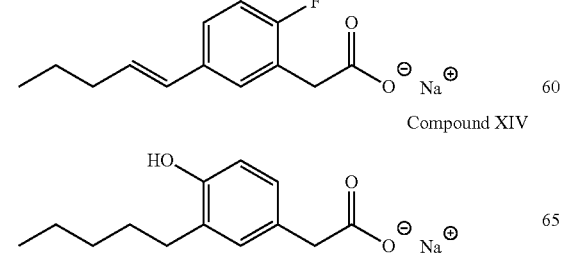

Compound XV
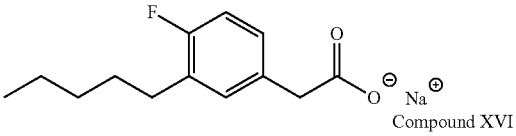

Compound XVI
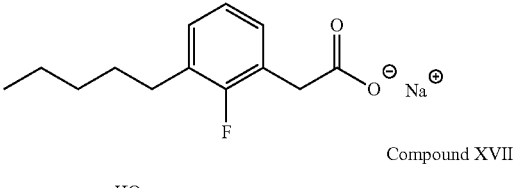

Compound XVII
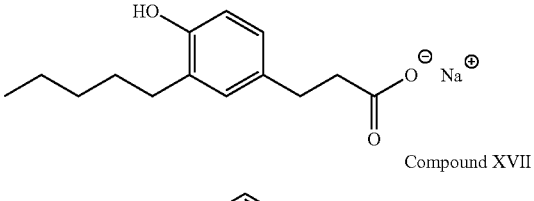

Compound XVII
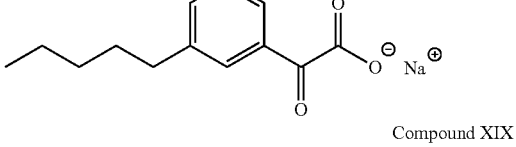

Compound XIX
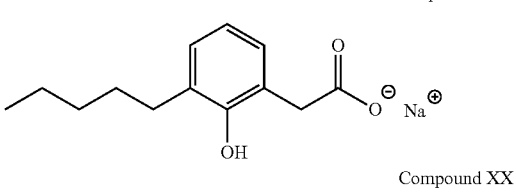

Compound XX
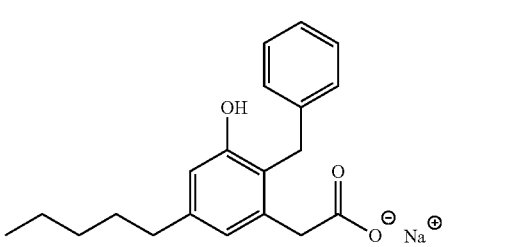

In an embodiment, the fibrotic disease is pulmonary fibrosis. In this embodiment, the therapeutically effective amount is preferably between about 1 to about 50 mg/kg, and preferably between about 1 to about 20 mg/kg. The compound is preferably administered orally. The subject is preferably a human. According to a preferred embodiment of the invention, the pulmonary fibrosis is idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension.

In an embodiment, the fibrotic disease is liver fibrosis. In this embodiment, the therapeutically effective amount is preferably between about 1 to about 50 mg/kg. The compound is preferably administered orally. The subject is preferably human. According to a preferred embodiment of the invention, the liver fibrosis is resulting from a chronic liver disease, hepatitis B virus infection, hepatitis C virus infection, hepatitis D virus infection, schistosomiasis, alcoholic liver disease or non-alcoholic steatohepatitis, obesity, diabetes, protein malnutrition, coronary artery disease, autoimmune hepatitis, cystic fibrosis, alpha-1-antitrypsin deficiency, primary biliary cirrhosis, drug reaction and exposure to toxins.

In an embodiment, the fibrotic disease is skin fibrosis. In this embodiment, the compound is preferably administered topically or orally. When administered topically, the therapeutically effective amount of the compound of the present invention is preferably between about 0.01 to about 10% (w/w). The subject is preferably human. When administered orally, the therapeutically effective amount of the compound of the present invention is preferably between about 1 to about 50 mg/kg and the subject is human. According to a preferred embodiment of the invention, the skin fibrosis is scarring, hypertrophic scarring, keloid scarring, dermal fibrotic disorder, wound healing, delayed wound healing, psoriasis or scleroderma. Said scarring may derived from a burn, a trauma, a surgical injury, a radiation or an ulcer. Said ulcer can be a diabetic foot ulcer, a venous leg ulcer or a pressure ulcer.

In an embodiment, the fibrotic disease is cardiac fibrosis. In this embodiment, the therapeutically effective amount is preferably between about 1 to about 50 mg/kg, and preferably between about 1 to about 20 mg/kg. The compound is preferably administered orally. The subject is preferably a human.

In addition to the previous embodiments of dosages, for all above mentioned fibrotic diseases, when the compound of the present invention is topically administered to a human, the therapeutically effective amount of a compound corresponds to preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). In all above mentioned fibrotic diseases, when the compound of the present invention is orally administered to a human, the therapeutically effective amount of a compound corresponds preferably between about 1 to about 50 mg/kg, or between about 1 to 25 mg/kg, or between about 1 to about 10 mg/kg, between about 5 to about 25 mg/kg, or between about 10 to about 20 mg/kg.

According to a preferred embodiment, the invention also concerns a method for antagonizing collagen secretion or collagen deposition in an organ, such as the lung, the liver, the skin or the heart, of a mammal comprising the administration of a therapeutically effective amount of a compound of the present invention to the mammal that is in need thereof, wherein the organ is lung, liver, skin or heart. The mammal that is in need thereof is a mammal that is subject to an excessive collagen secretion or collagen deposition in an organ such as the lung, the liver, the skin or the heart. Usually, the excessive collagen secretion or collagen deposition in an organ results from an injury or an insult. Such injury and insult are organ-specific and are described herein in details in the background section and in the whole specification. The therapeutically effective amount described hereinabove in detail also applies to the present method for antagonizing collagen secretion or collagen deposition in an organ. The route of administration described herein also applies to the present method. The compound is preferably administered over a sufficient period of time to antagonize the level of collagen deposition in the organ, completely or partially. The term "antagonizing" used herein is intended to mean "decreasing" or "reducing". A sufficient period of time can be during one week, or between 1 week to 1 month, or between 1 to 2 months, or 2 months or more. For chronic condition, the compound of the present invention can be advantageously administered for life time period.

The present invention also concerns a method for reducing the collagen production in cells, which comprises contacting the cells with a therapeutically effective amount of a compound of the present invention. The collagen is preferably collagen 1. The collagen production is preferably the collagen mRNA expression or the production of the collagen protein. According to a preferred embodiment, the cells are in culture, are part of an organ or are part of an organ that is entirely part of a live animal, where said animal includes, without limitation, a mouse, a rat or a human. In the case that the cells are part of an organ that is entirely part of a live animal, the step of contacting the cells with a therapeutically effective amount of a compound of the present invention is equivalent to administering the compound to the animal. In the case that the cells are part of an organ that is entirely part of a live animal and the live animal is a human, the therapeutically effective amount of a compound corresponds to a topical administration of preferably between about 0.01 to about 10% (w/w), or between about 0.1 to 10% (w/w), or between about 1.0 to about 10% (w/w), between about 0.1 to about 5% (w/w), or between about 1.0 to about 5% (w/w), or to an oral administration of preferably between about 1 to about 50 mg/kg, or between about 1 to 25 mg/kg, or between about 1 to about 10 mg/kg, between about 5 to about 25 mg/kg, or between about 10 to about 20 mg/kg. In the case of cultured cells, the therapeutically effective amount of a compound corresponds to 0.01 to 0.5 mM, and preferably of about 0.2 mM.

In another preferred embodiment, the compound of the present invention is administered in combination with a therapeutically effective amount of second compound where the second compound is preferably a therapeutic agent known for being effective in preventing or treating or potentially preventing or treating a pulmonary fibrosis, a liver fibrosis or skin fibrosis. In another preferred embodiment, the compound is administered in combination with a therapeutically effective amount of second compound, the second compound is an immunosuppressive drug, an anti-inflammatory drug, a cytokine, a monoclonal antibody, a multiple receptor tyrosine kinase inhibitor, an antioxidant, an enzyme inhibitor, an integrin inhibitor, a lipid receptor modulator, or a thiazolindione.

In a preferred embodiment where the fibrotic disease is pulmonary fibrosis, the compound of the present invention is administered in combination with a therapeutically effective amount of pirfenidone. In this case, the preferred compound is Compound I. In the case that the subject affected by the pulmonary fibrosis is a human, the therapeutically effective amount of Compound I is between about 1 to about 50 mg/kg, or between about 1 to 25 mg/kg, or between about 1 to about 10 mg/kg, between about 5 to about 25 mg/kg, or between about 10 to about 20 mg/kg and the pirfenidone is between about 10 mg/kg to about 40 mg/kg, or between about 1.0 g/day to about 2.5 g/day, when orally administered. The combination of the compound of the present invention and the second therapeutic agent can be administered in a single preparation or in separate preparations.

The present invention also concerns a kit for preventing and/or slowing progression of and/or treating fibrotic disease in a subject in need thereof. The kit comprises a compound represented by the formula:

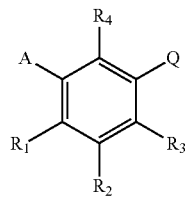

or a pharmaceutically acceptable salt thereof, wherein

A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4; or is preferably $C_5$ alkyl, $C_5$ alkenyl, C(O)—$(CH_2)_n$—$CH_3$ or CH(OH)—$(CH_2)_n$—$CH_3$ wherein n is 3; or is preferably $C_6$ alkyl, $C_6$ alkenyl, C(O)—$(CH_2)_n$—$CH_3$ or CH(OH)—$(CH_2)_n$—$CH_3$ wherein n is 4;

$R_1$ is H, OH or F; or is preferably H or OH;

$R_2$ is H, OH, F or $CH_2$—OH; or is preferably H, OH or F; or is preferably H or OH;

$R_3$ is H, OH, F or $CH_2Ph$; or is preferably H, OH or F; or is preferably H or OH;

$R_4$ is H, OH or F; or is preferably H or OH;

Q is

1) $(CH_2)_mC(O)OH$ wherein m is 1 or 2,
2) $CH(CH_3)C(O)OH$,
3) $C(CH_3)_2C(O)OH$,
4) CH(F)—C(O)OH,
5) $CF_2$—C(O)OH, or
6) C(O)—C(O)OH;

and instructions for administering a therapeutically effective amount of the compound to the subject suffering from said fibrotic disease, wherein the fibrotic disease is pulmonary fibrosis, liver fibrosis, heart fibrosis or skin fibrosis.

When the fibrotic disease is pulmonary fibrosis, heart fibrosis or liver fibrosis, the kit preferably further comprises instructions for administering between about 1 to about 50 mg/kg of the compound daily and orally to the subject who is a human. The kit may also comprises instructions for administering any of the above-disclosed therapeutically effective amount of the compound for oral administration.

When the fibrotic disease is skin fibrosis, the kit preferably further comprises instructions for administering between about 0.01 to about 10% (w/w) of the compound daily and topically to the subject who is a human; or instructions for administering between about 1 to about 50 mg/kg of the compound daily and orally to the subject who is a human. The kit may also comprises instructions for administering any of the above-disclosed therapeutically effective amount of the compound for topical administration.

The present invention also concerns novel compounds represented by the formula:

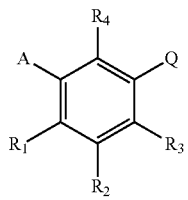

or a pharmaceutically acceptable salt thereof, wherein

A is $C_5$ alkyl, $C_6$ alkyl, $C_5$ alkenyl, $C_6$ alkenyl, C(O)—$(CH_2)_n$—$CH_3$ or CH(OH)—$(CH_2)_n$—$CH_3$ wherein n is 3 or 4;

$R_1$ is H, OH or F;

$R_2$ is H, OH, F or $CH_2$—OH;

$R_3$ is $CH_2Ph$;

$R_4$ is H, OH or F;

Q is

1) $(CH_2)_mC(O)OH$ wherein m is 1 or 2,
2) $CH(CH_3)C(O)OH$,
3) $C(CH_3)_2C(O)OH$,
4) CH(F)—C(O)OH,
5) $CF_2$—C(O)OH, or
6) C(O)—C(O)OH.

A preferred embodiment of this compound is Compound XX having the following structure:

Compound XX

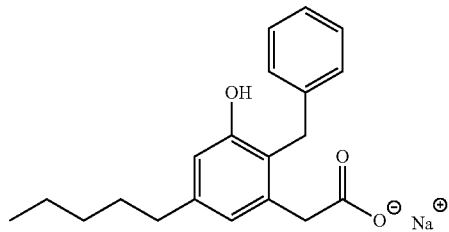

Real-time PCR using rat CTGF TaqMan® Gene Expression Assay was normalized to rat Gapdh endogenous control.

Figure 5:
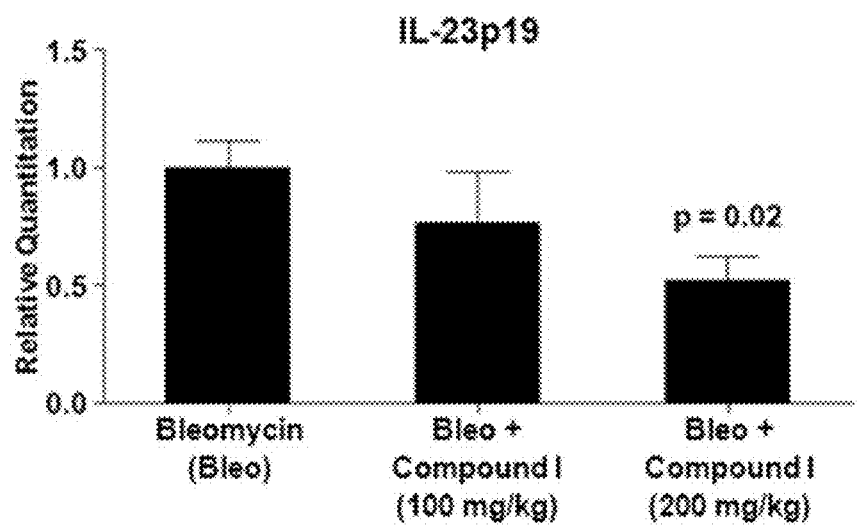

FIG. 5 represents the IL-23p19 content of lung tissue from bleomycin-induced pulmonary fibrosis mouse model following oral treatment with Compound I at a dose of 100 and 200 mg/kg or oral treatment with vehicle (water) (Bleo). Real-time PCR using rat IL-23p19 TaqMan® Gene Expression Assay was normalized to rat Gapdh endogenous control.

Figure 6:
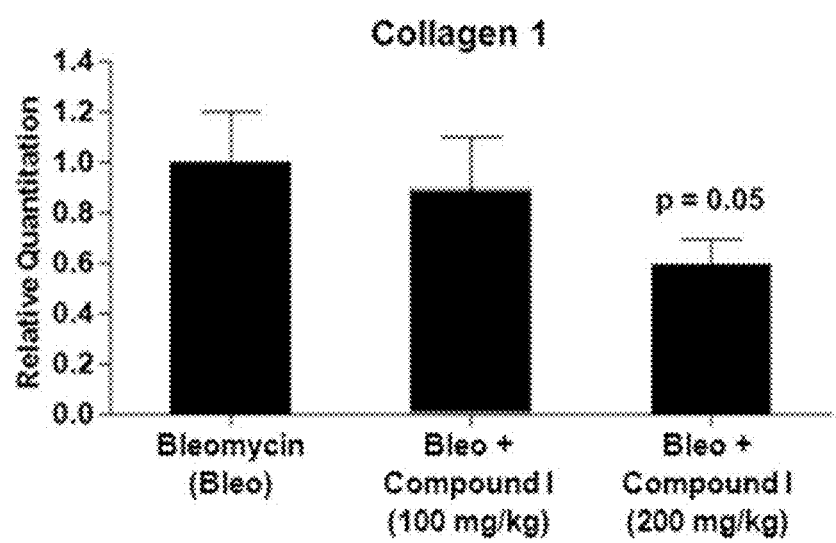

FIG. 6 represents the Collagen 1 content of lung tissue from bleomycin-induced pulmonary fibrosis mouse model following oral treatment with Compound I at a dose of 100 and 200 mg/kg or oral treatment with vehicle (water) (Bleo). Real-time PCR using rat Collagen 1 TaqMan® Gene Expression Assay normalized to rat Gapdh endogenous control.

Figure 7:
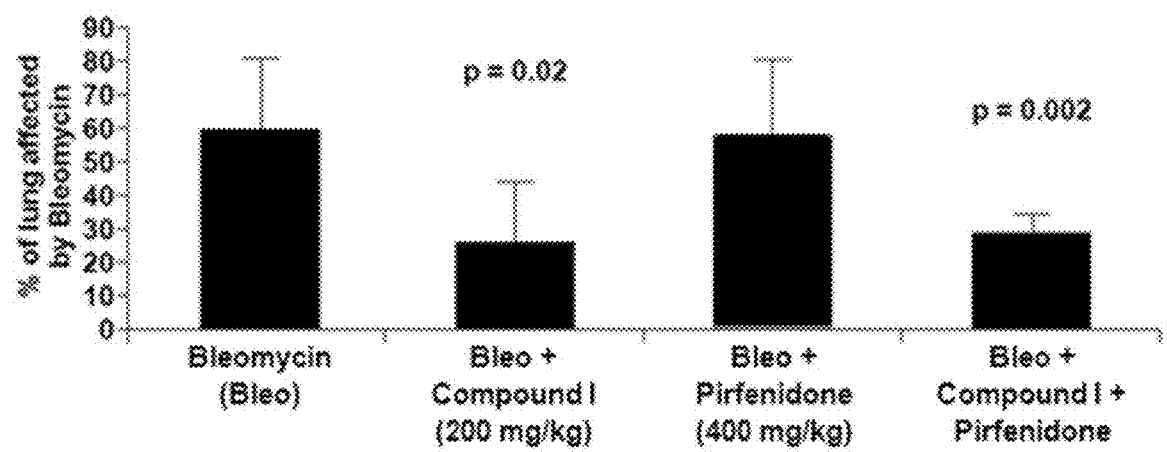

FIG. 7 shows percentage of lungs affected by bleomycin from bleomycin-induced pulmonary fibrosis mouse model following oral treatment with Compound 1 (200 mg/kg), pirfenidone (400 mg/kg), the combination of Compound I (200 mg/kg) and pirfenidone (400 mg/kg), or with vehicle (water) (Bleo).

Figure 8:
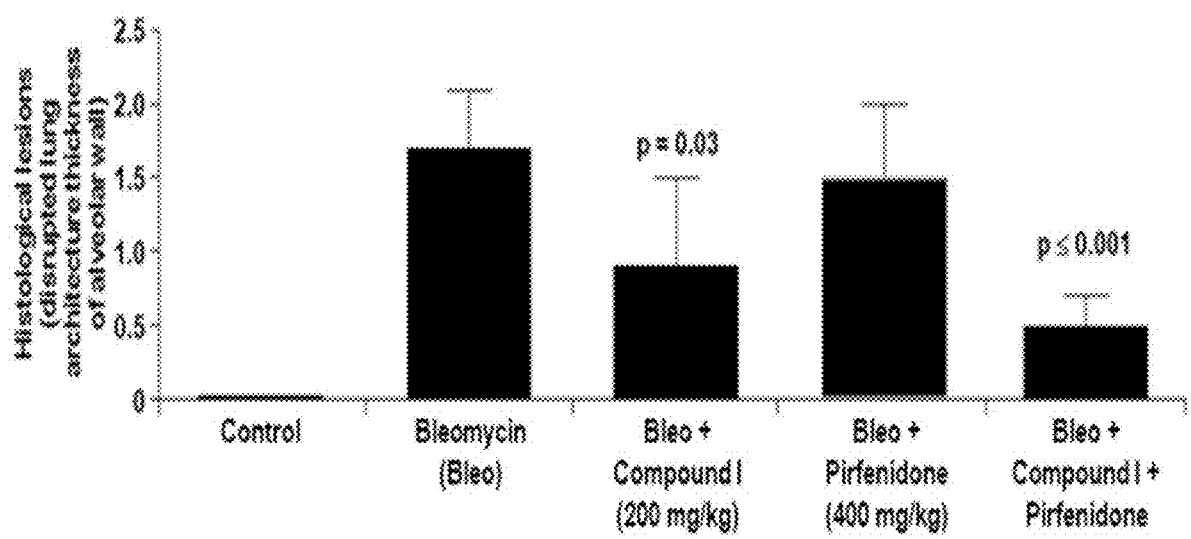

FIG. 8 represents the histological lesion score of lungs affected by bleomycin from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue of normal mouse (no bleomycin) (Control).

Figure 9:
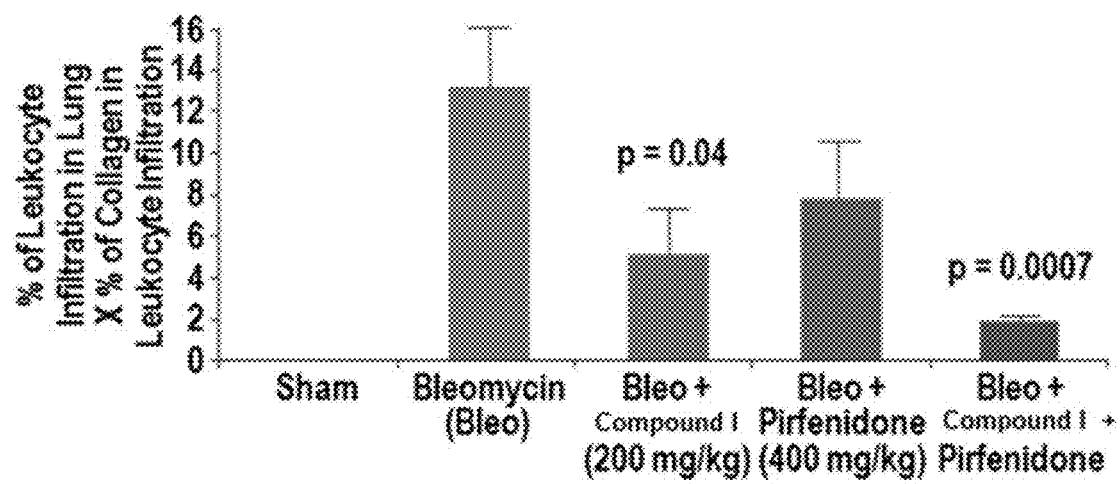

FIG. 9 shows the lesions score as determined by the percentage of leukocyte infiltration (inflammatory zone) multiplied by the percentage of collagen found in the leukocyte infiltrate and quantified by histomorphometry using Masson's trichrome staining in lungs affected by bleomycin from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue of normal mouse (no bleomycin) (Sham).

Figure 10:
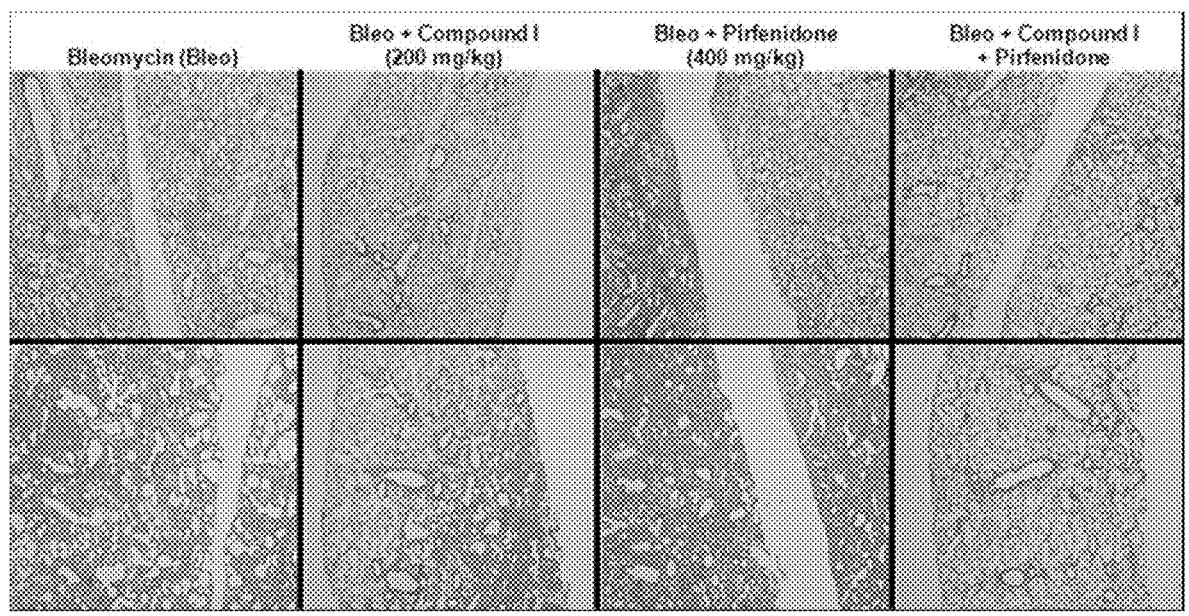

FIG. 10 presents photomicrographs of lung tissue from bleomycin-induced pulmonary fibrosis mouse model stained with HEP following oral treatment with Compound I (200 mg/kg), pirfenidone (400 mg/kg), the combination of Compound I (200 mg/kg) and pirfenidone (400 mg/kg), or oral treatment with vehicle (water) (Bleo).

Figure 11:
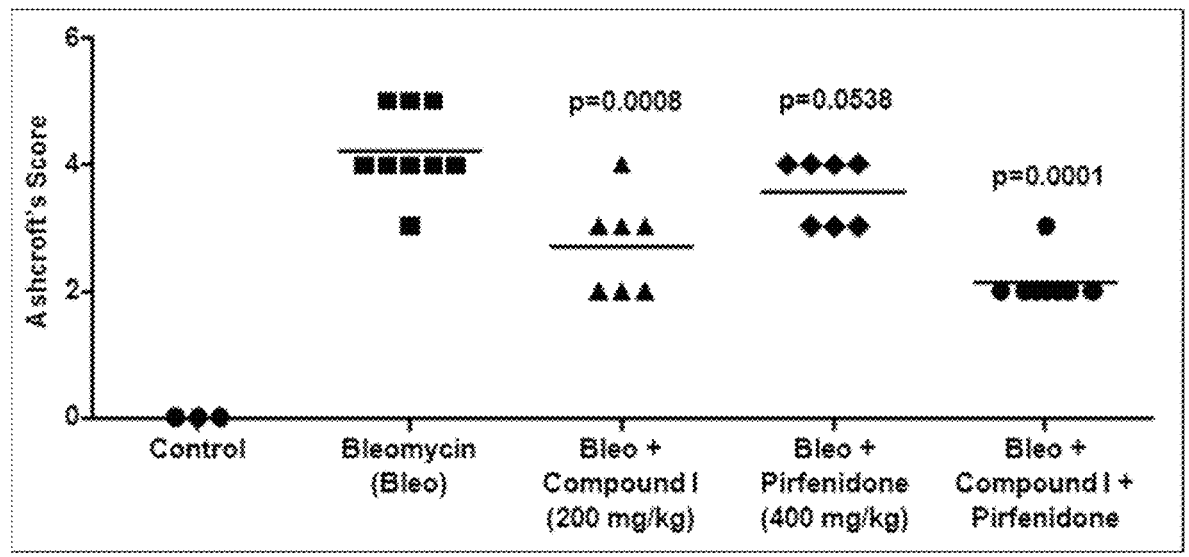

FIG. 11 represents the visual grading of pulmonary fibrosis determined by the Ashcroft's score of lungs from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 12:
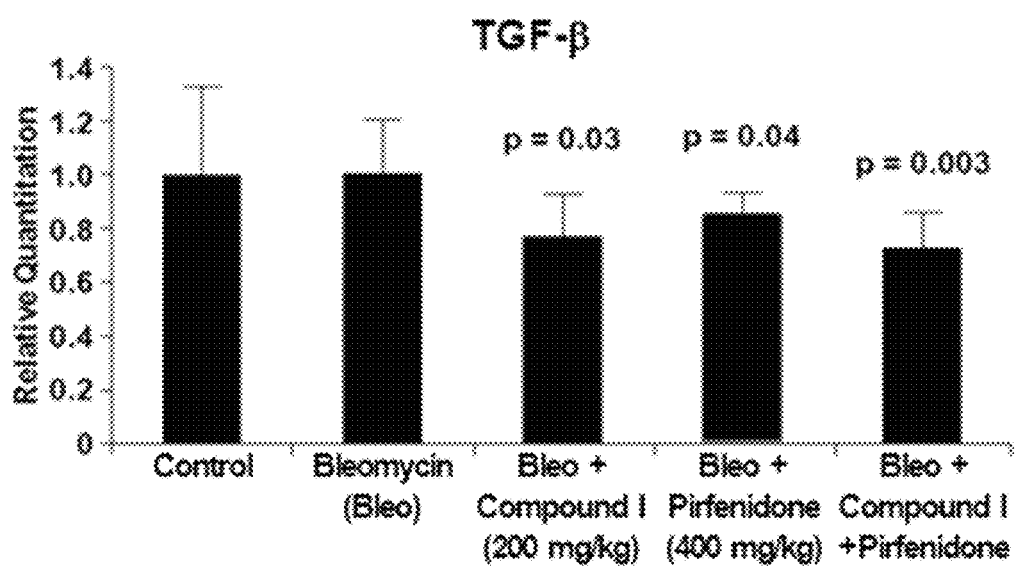

FIG. 12 shows the TGF-β mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 13:
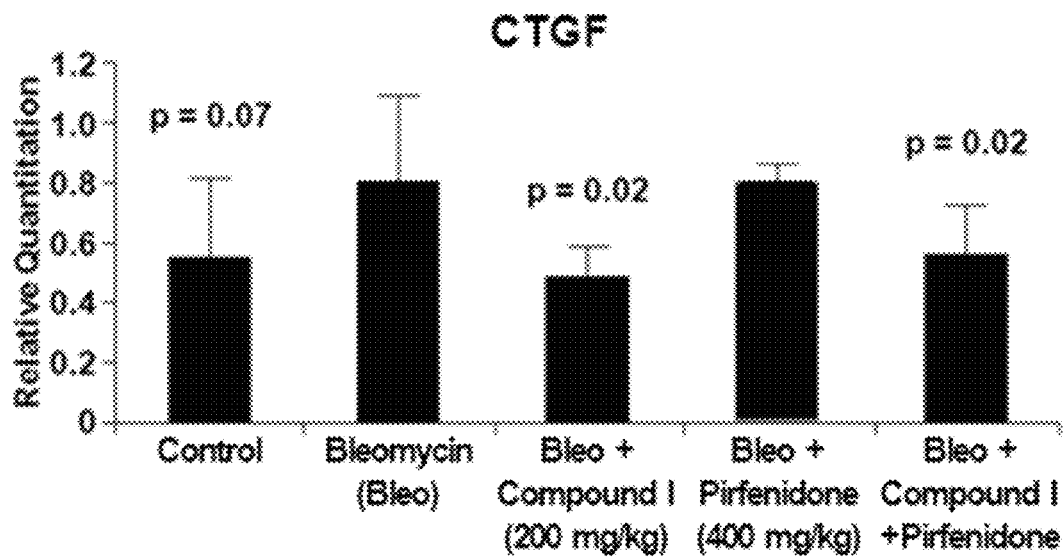

FIG. 13 shows the CTGF mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 14:
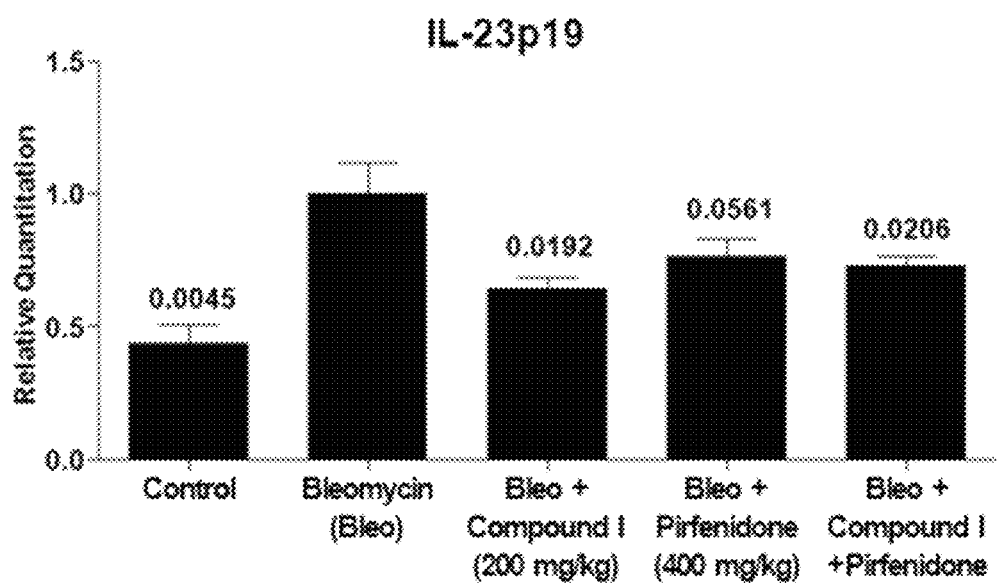

FIG. 14 shows the IL-23p19 mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 15:
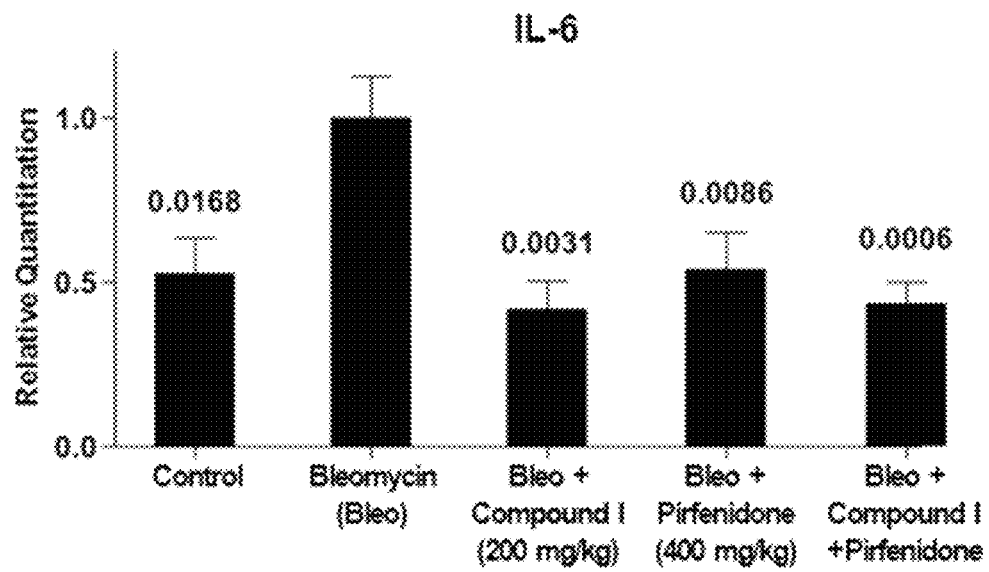

FIG. 15 shows the IL-6 mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 16:
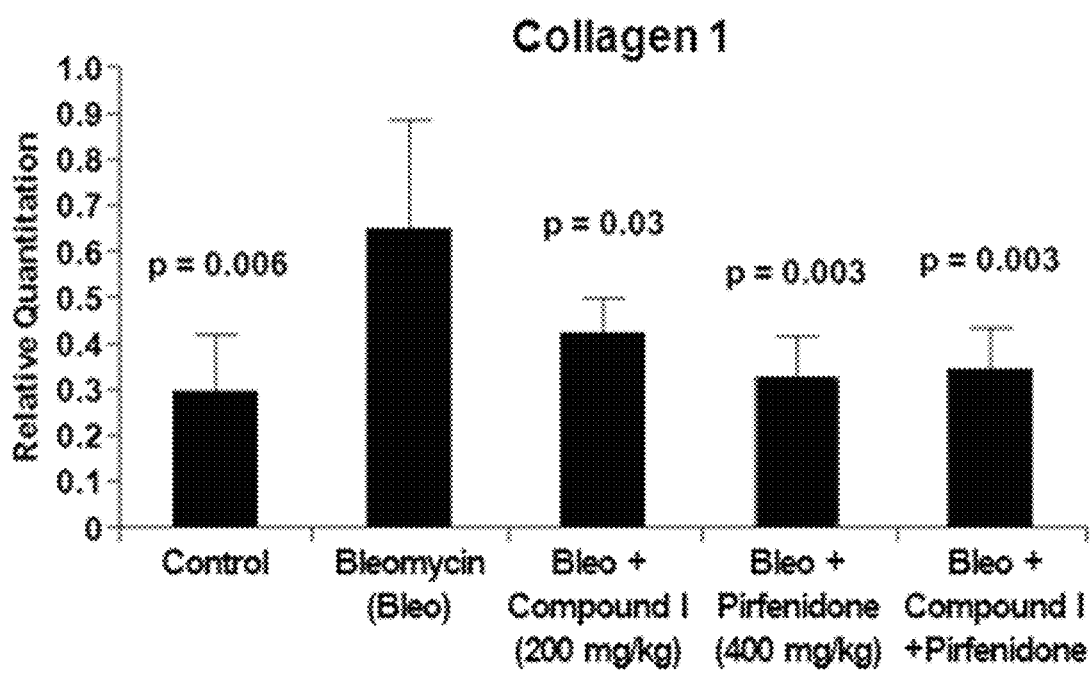

FIG. 16 shows the Collagen 1 mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (control).

Figure 17:
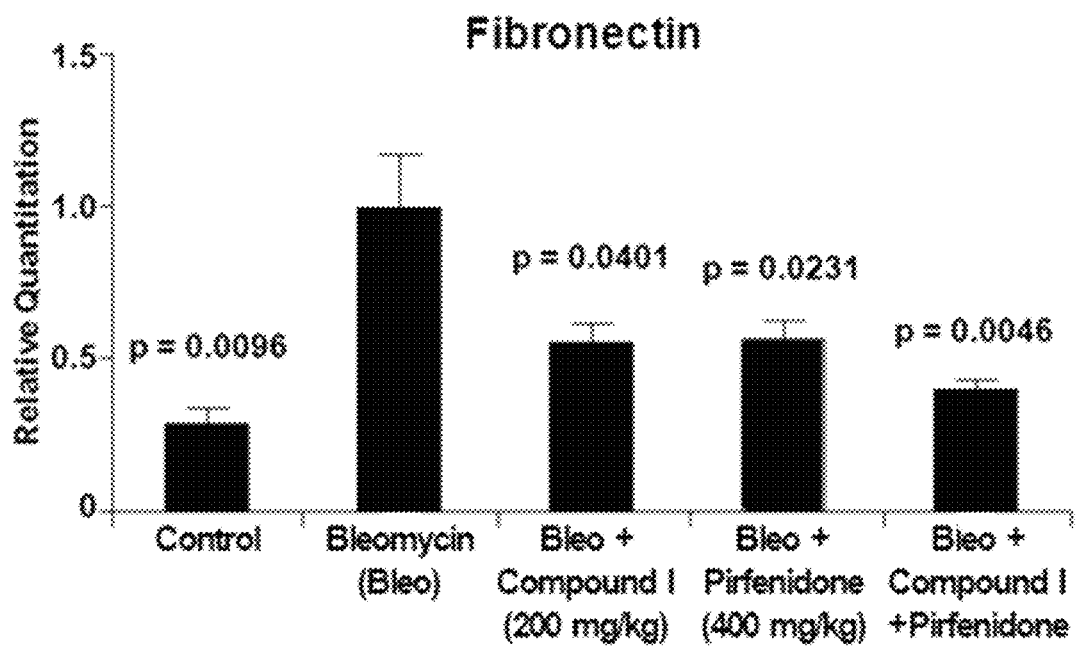

FIG. 17 shows the Fibronectin (FN-1) mRNA content of lung tissue from bleomycin-induced pulmonary fibrosis mouse model following oral treatment with Compound I (200 mg/kg), pirfenidone (400 mg/kg), the combination of Compound 1 (200 mg/kg) and pirfenidone (400 mg/kg), or oral treatment with vehicle (water) (Bleo); and of lung tissue from normal mouse (no bleomycin) (Control).

Figure 18:
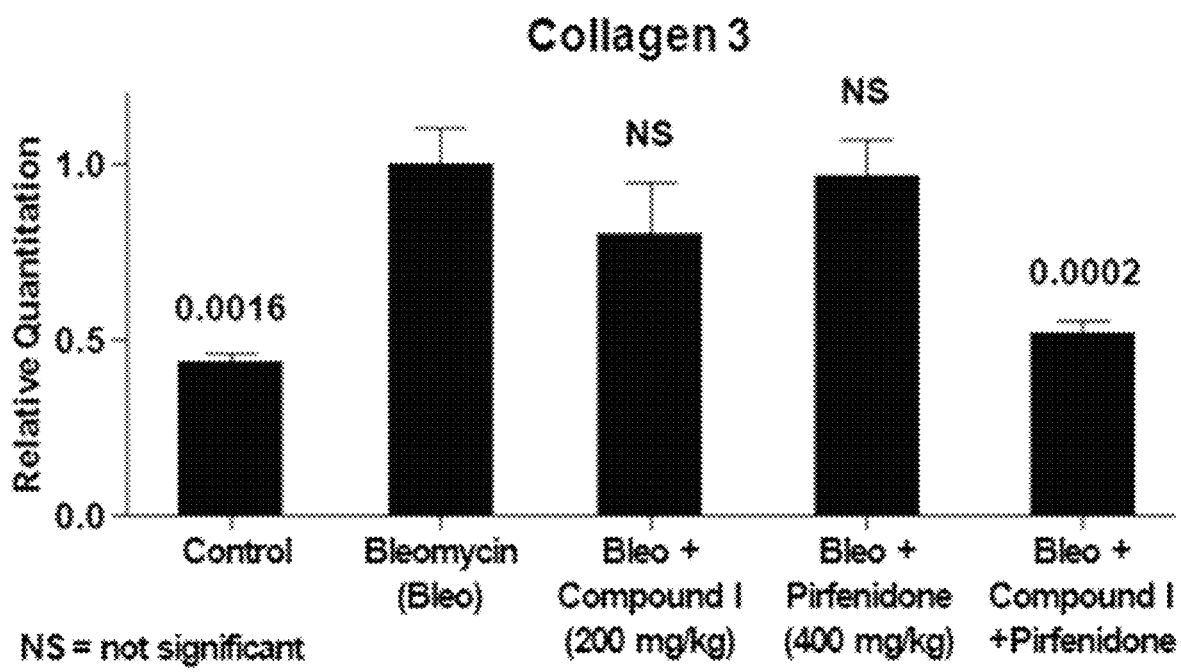

FIG. 18 shows the Collagen 3 mRNA content of lung tissue from bleomycin-induced pulmonary fibrosis mouse model following oral treatment with Compound I (200 mg/kg), pirfenidone (400 mg/kg), the combination of Compound I (200 mg/kg) and pirfenidone (400 mg/kg), or oral treatment with vehicle (water) (Bleo); and of lung tissue from normal mouse (no bleomycin) (Control).

Figure 19:
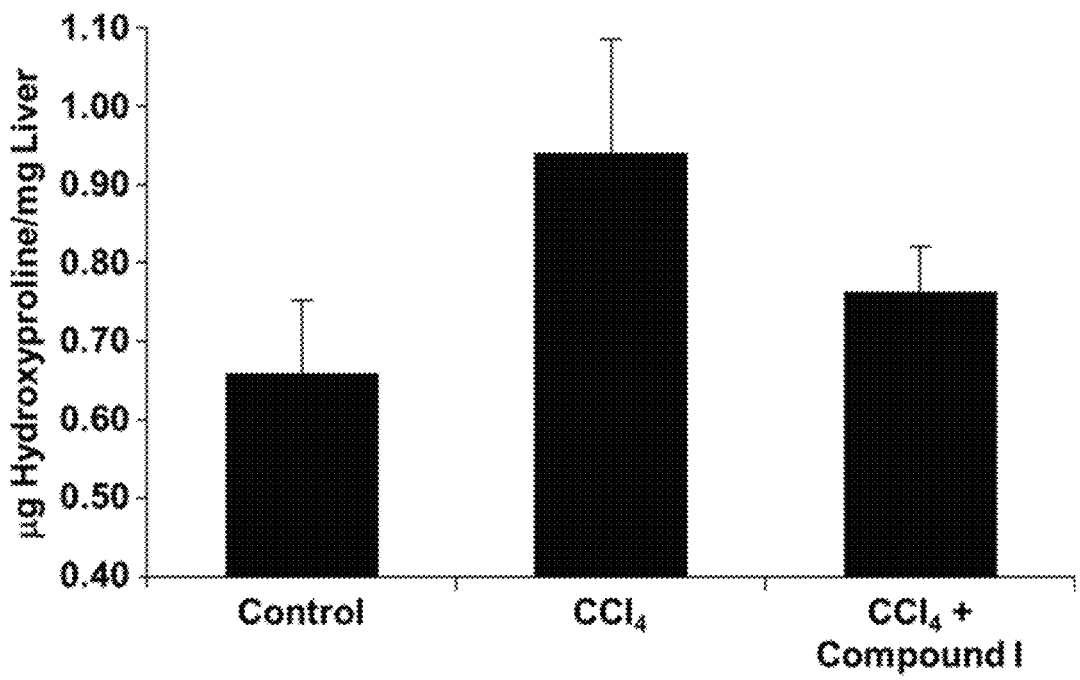

FIG. 19 shows the hydroxyproline level in liver from $CCl_4$-induced liver fibrosis mouse model following daily oral administration with Compound I, or oral administration with vehicle (water) ($CCl_4$); and in liver from normal mouse (no $CCl_4$) (Control).

Figure 20:
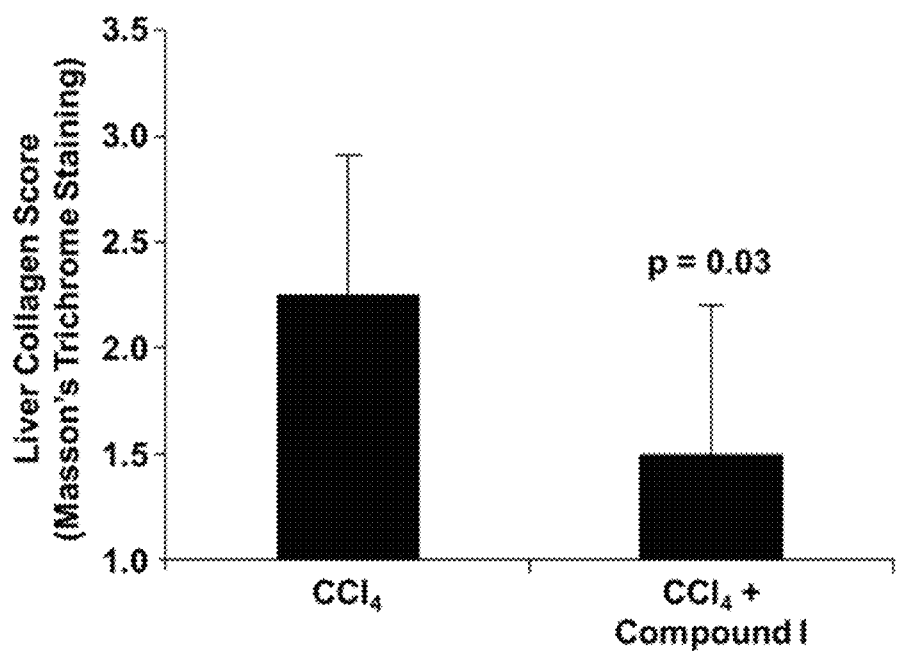

FIG. 20 shows the collagen level in liver from $CCl_4$-induced liver fibrosis mouse model following daily oral administration with Compound I, or oral administration with vehicle (water) ($CCl_4$).

Figure 21:
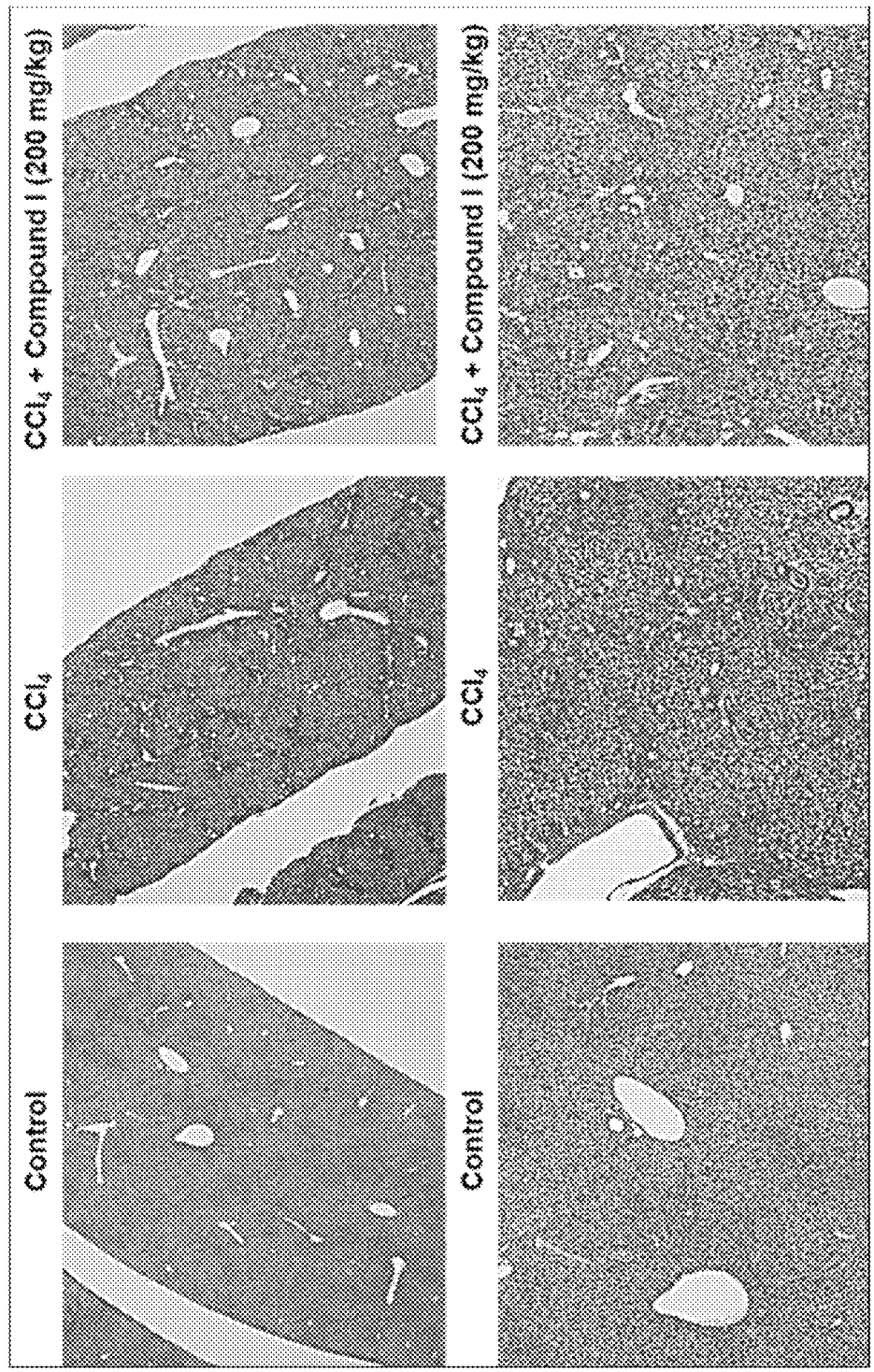

FIG. 21 represents photomicrographs of liver from $CCl_4$-induced liver fibrosis mouse model following daily oral administration with Compound I (200 mg/kg), or oral administration with vehicle (water) ($CCl_4$); and in liver from normal mouse (no $CCl_4$) (Control).

Figure 22:
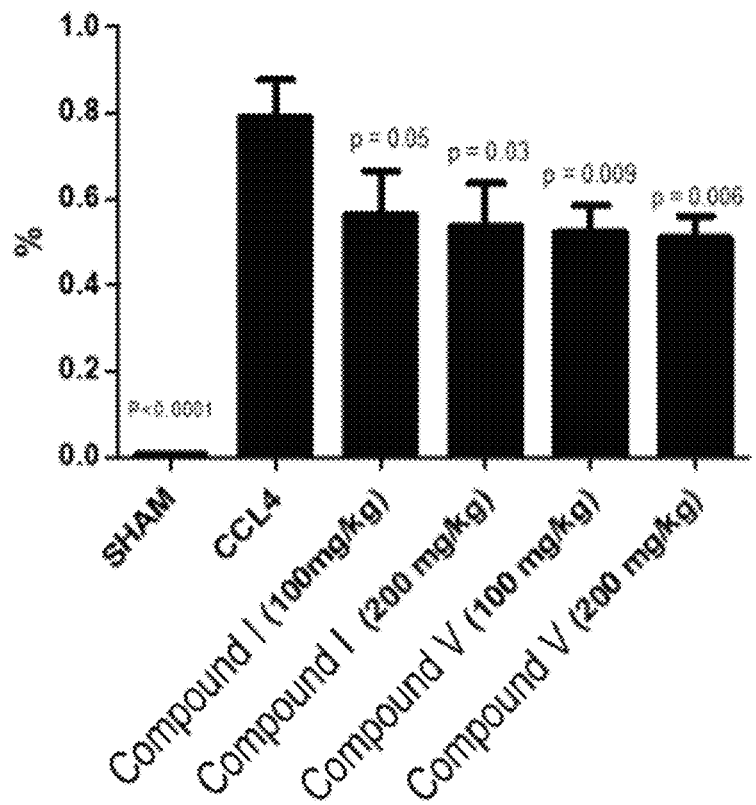

FIG. 22 shows the percentage of collagen content over total liver area, determined by histomorphometry (Masson's trichrome staining), in liver from $CCl_4$-induced liver fibrosis mouse model following daily oral administration with Compound I and Compound V at doses of 100 mg/kg and 200 mg/kg daily, or oral administration with vehicle (water) ($CCl_4$).

Figure 23:
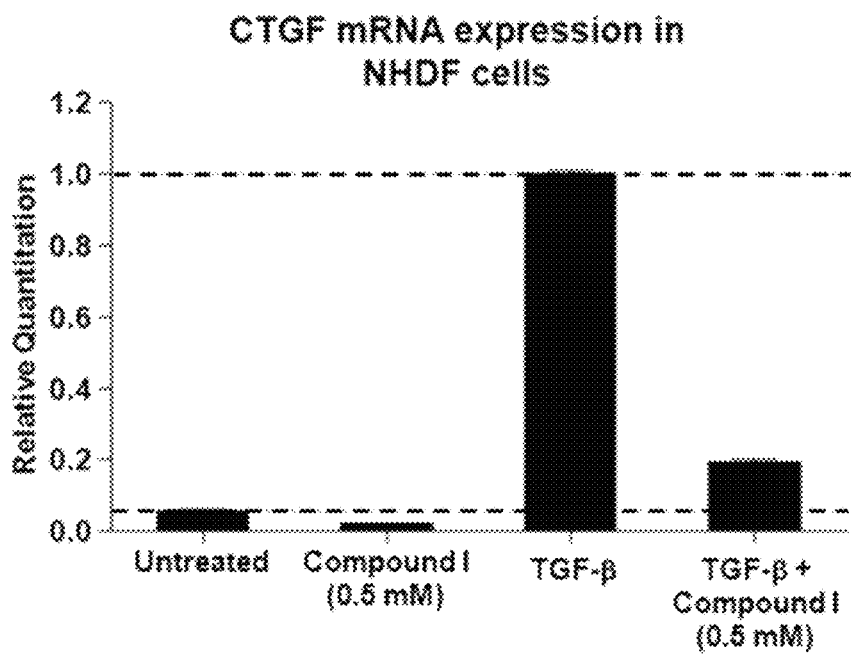

FIG. 23 shows the CTGF mRNA content in normal human dermal fibroblasts (NHDF) cultured with Compound I (0.5 mM) alone, TGF-β alone or in combination, or without (Untreated). Real-time PCR using human CTGF TaqMan® Gene Expression Assay was normalized to human GAPDH endogenous control; reference is TGF-β-treated cells (RQ=1).

Figure 24:
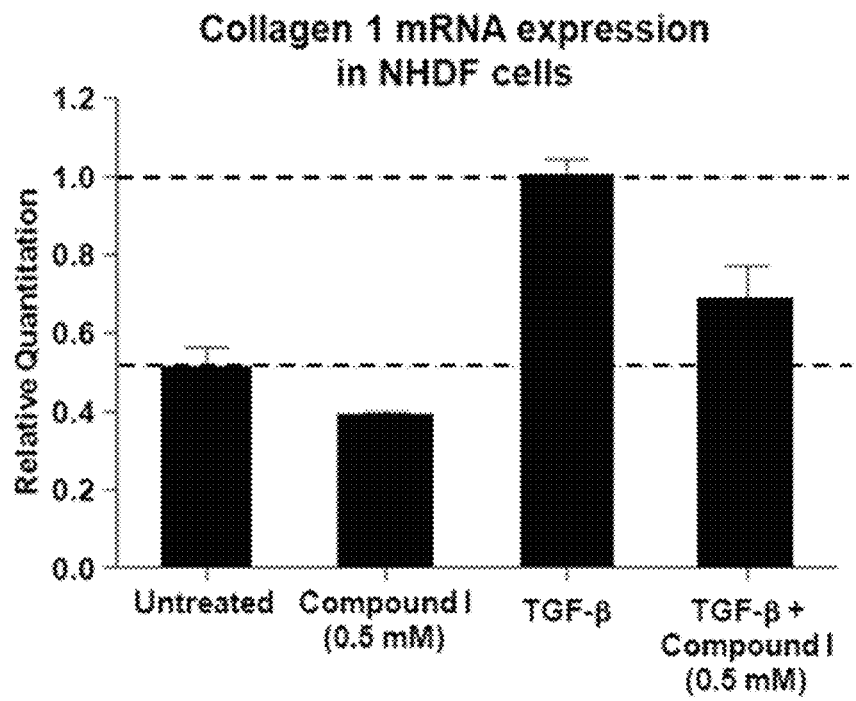

FIG. 24 shows the Collagen 1 mRNA content in normal human dermal fibroblasts (NHIDF) cultured with Compound 1 (0.5 mM) alone, TGF-β alone or in combination, or without (Untreated). Real-time PCR using human Collagen 1 TaqMan® Gene Expression Assay was normalized to human GAPDH endogenous control; reference is TGF-β-treated cells (RQ=1).

Figure 25:
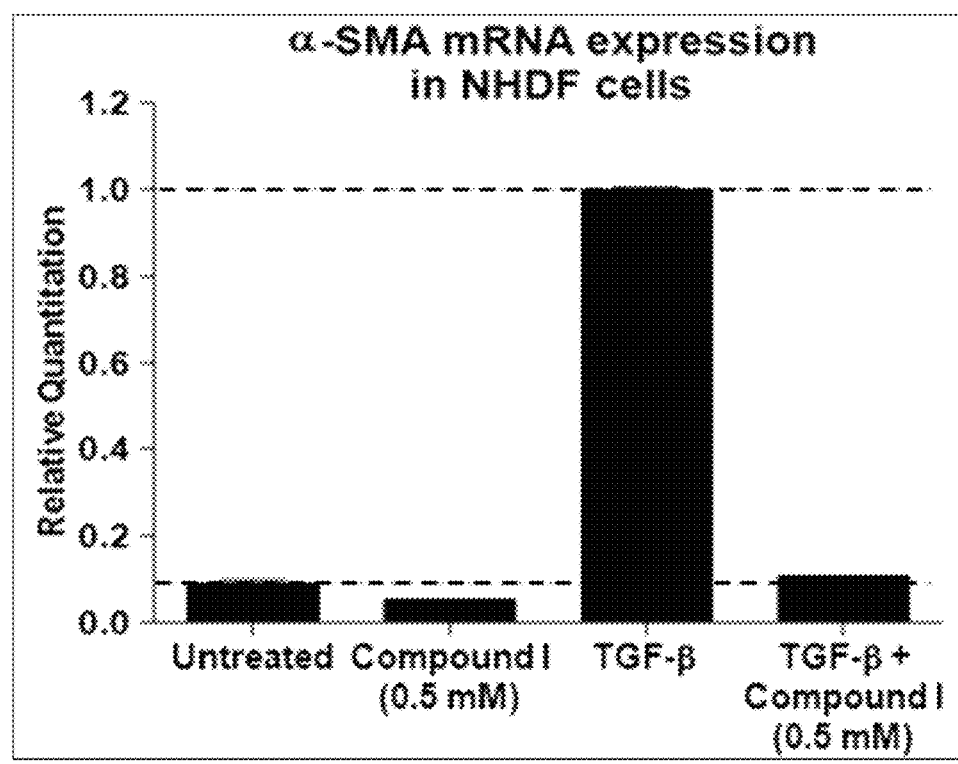

FIG. 25 shows the α-SMA mRNA content in normal human dermal fibroblasts (NHDF) cultured with Compound I (0.5 mM) alone, TGF-β alone or in combination, or without (Untreated). Real-time PCR using human α-SMA TaqMan® Gene Expression Assay was normalized to human GAPDH endogenous control; reference is TGF-β-treated cells (RQ=1).

Figure 26:
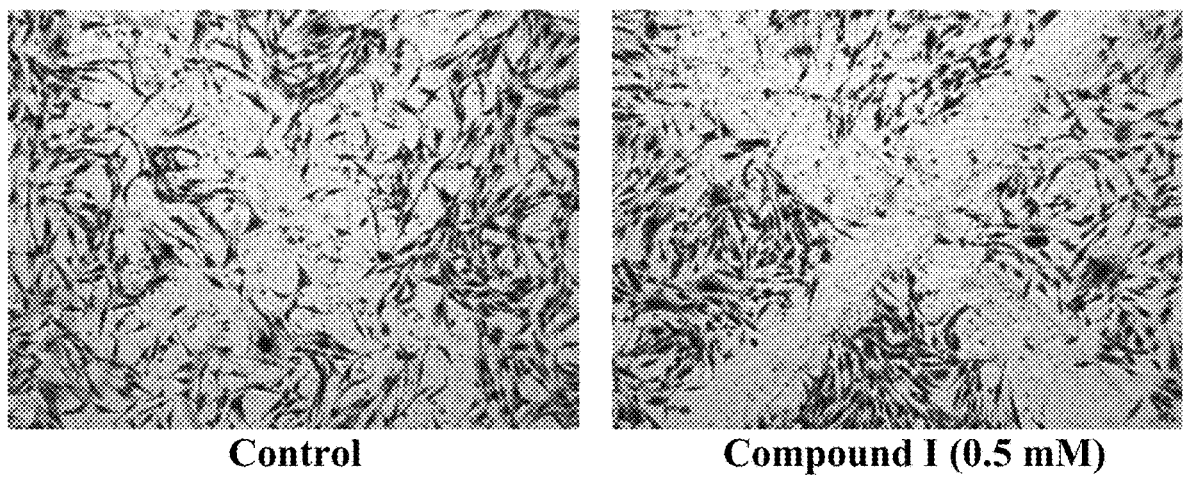

FIG. 26 represents a scratch assay (migration and invasion assay) of normal human dermal fibroblasts (NHDF) cultured with and without Compound I (0.5 mM) showing the reduction of the migration and invasion of the treated cells into the scratch.

Figure 27:
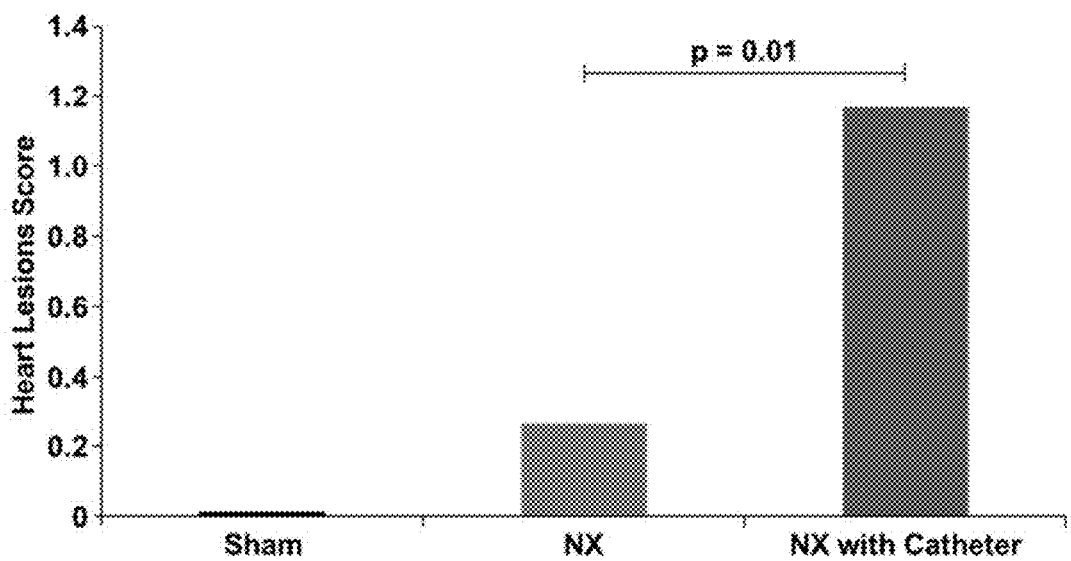

FIG. 27 shows that use of a catheter in 5/6-Nx rats (NX with Catheter) induces an increased in heart lesion level compared to the 5/6-Nx rats not implanted with a catheter (NX), and compared to the non nephrectomized rats (Sham).

Figure 28:
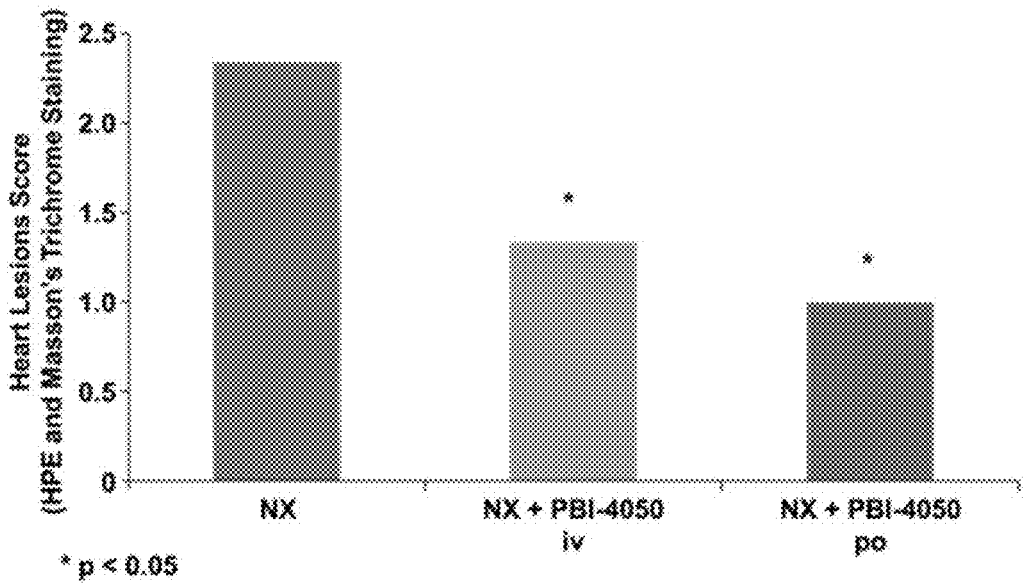

FIG. 28 represents the lesion level determined by histological evaluation (HPE and Masson's trichrome staining) in heart from 5/6 nephrectomized-catheterized (5/6-Nx) rats following intravenous (iv) administration with Compound I or the oral (po) administration with Compound I compared to non-treated 5/6-Nx rats (NX).

Figure 29:
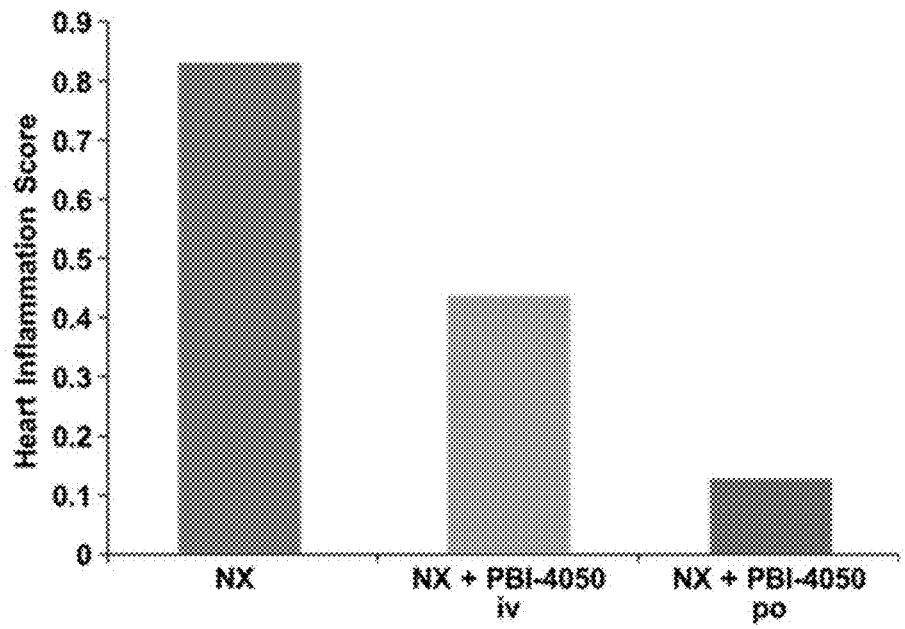

FIG. 29 represents the inflammation level in heart from 5/6 nephrectomized-catheterized (5/6-Nx) rats following intravenous (iv) administration with Compound I or the oral (po) administration with Compound I compared to non-treated 5/6-Nx rats (NX).

Figure 30:
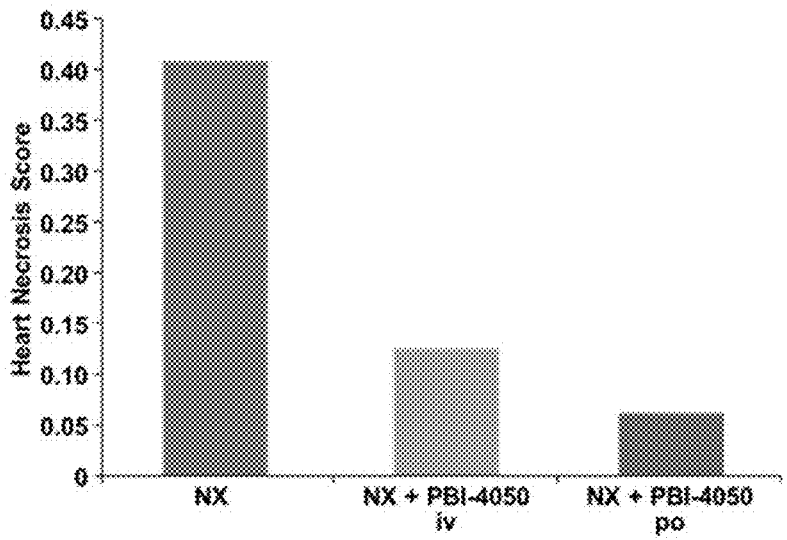

FIG. 30 represents the necrosis level in heart from 5/6 nephrectomized-catheterized (5/6-Nx) rats following intravenous (iv) administration with Compound I or the oral (po) administration with Compound I compared to non-treated 5/6-Nx rats (NX).

Figure 31:
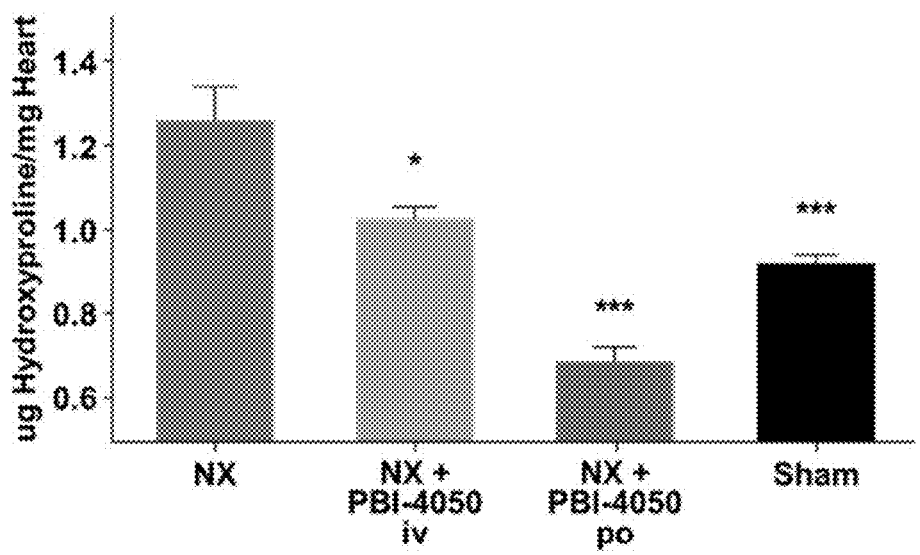

FIG. 31 represents the hydroxyproline (collagen) content in heart from 5/6 nephrectomized-catheterized (5/6 Nx) rats following intravenous (iv) administration with Compound I or the oral (po) administration with Compound I compared to non-treated 5/6-Nx rats (NX) and non-nephrectomized rats (Sham).

Figure 32:
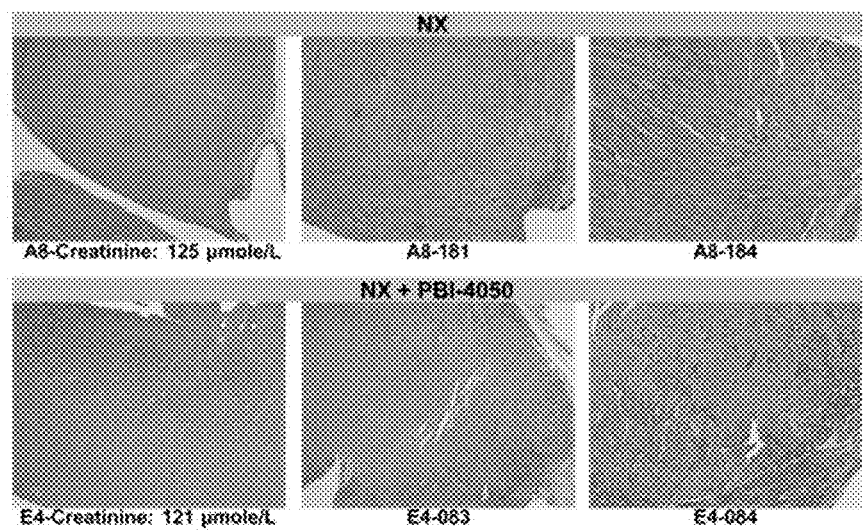

FIG. 32 shows photomicrographs at a magnification view of 40× of the heart of a 5/6 nephrectomized-catheterized (5/6 Nx) rats treated with oral administration of Compound I, and non-treated 5/6-Nx rats (NX).

Figure 33:
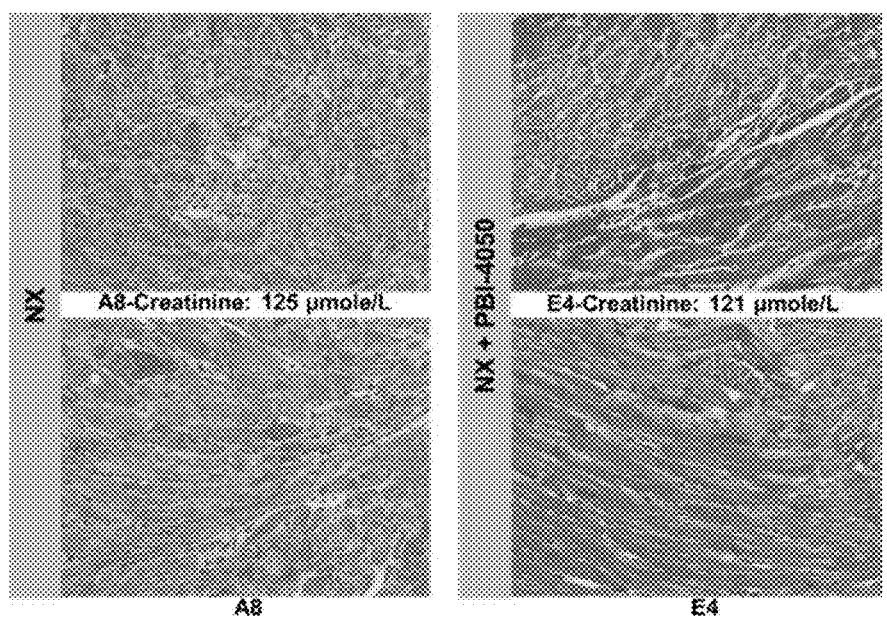

FIG. 33 shows photomicrographs at a magnification view of 100× of the heart of a 5/6 nephrectomized-catheterized (5/6 Nx) rats treated with oral administration of Compound I, and non-treated 5/6-Nx rats (NX).

Figure 34:
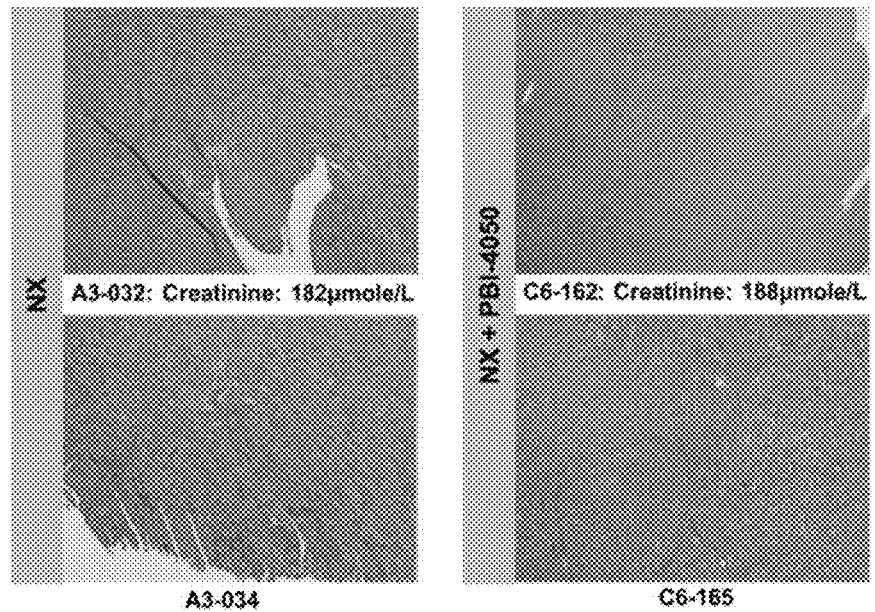

FIG. 34 shows photomicrographs at a magnification view of 40× of the heart of a 5/6 nephrectomized-catheterized (5/6 Nx) rats treated with intravenous administration of Compound I, and non-treated 5/6-Nx rats (NX).

DETAILED DESCRIPTION OF THE INVENTION

As used herein, the term "alkyl" is intended to include both branched and straight chain saturated aliphatic hydrocarbon groups having five or six carbon atoms. Examples of alkyl defined above include, but are not limited to, n-pentyl, n-hexyl, iso-pentyl, iso-hexyl, t-pentyl and t-hexyl. Similarly, as used herein, the term "alkenyl" is intended to include unsaturated straight or branched chain hydrocarbon groups having five or six carbon atoms, and in which at least two carbon atoms are bonded to each other by a double bond, and having E or Z regiochemistry and combinations thereof. Examples of alkenyl defined above include, but are not limited to, 1-pentenyl, 2-pentenyl, 1-hexenyl and 2-hexenyl.

The compounds of the present invention, or their pharmaceutically acceptable salts may contain one or more asymmetric centers, chiral axes and chiral planes, and may thus give rise to enantiomers, diastereomers and other stereoisomeric forms and subsequently may be defined in terms of absolute stereochemistry such as (R)- or (S)-. The present invention is therefore intended to include all such possible isomers, as well as their racemic and optically pure forms. Optically active (+) and (−), (R)- and (S)-, or (D)- and (L); isomers may be prepared using chiral synthons or chiral reagents or resolved using conventional techniques, such as reverse phase HPLC. The racemic mixtures may be prepared and subsequently separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, or selective reaction of one enantiomer with an enantiomer specific reagent.

As used herein, the term "pharmaceutically acceptable salt" is intended to mean those salts which retain the biological effectiveness and properties of the free acids, which are not biologically or otherwise undesirable. These salts are derived from addition of an inorganic base or an organic base to the organic acid. Salts prepared from inorganic bases include, but are not limited to, the sodium, potassium, lithium, ammonium, calcium, magnesium, manganese, zinc, iron, copper and the like. Salts prepared from organic bases include, but are not limited to, salts of primary, secondary and tertiary amines, substituted amines including naturally occurring substituted amines, cyclic amines and basic amino acids (lysine, arginine, and histidine). Examples of pharmaceutically acceptable salts are also described, for example, in Berge et al., "Pharmaceutical Salts", J. Pharm. Sci. 66, 1-19 (1977). Preferred salt of the compound of the present invention are sodium, potassium, lithium, ammonium, calcium and magnesium; and more preferably sodium. Pharmaceutically acceptable salts may be synthesized from the parent compound that contains an acid moiety by conventional chemical methods. Generally, such salts are prepared by reacting the free acid form of these compounds with a stoichiometric amount of the appropriate base in water or in an organic solvent, or in an aqueous/organic solvent mixture. Salts may be prepared in situ, during the final isolation or purification of the compound or by separately reacting the purified compound of the invention in the free acid form with the desired corresponding base, and isolating the product salt.

As indicated herein above and exemplified herein below, the compound of the invention has beneficial pharmaceutical properties and may have useful pharmaceutical applications in the prevention and/or treatment of various diseases and conditions in a subject. Medical and pharmaceutical applications contemplated by the inventors include, but are not limited to, those addressing pulmonary fibrosis, liver fibrosis, heart fibrosis and skin fibrosis.

The term "subject" includes living organisms in which pulmonary fibrosis can occur, or which are susceptible to such a condition. The term "subject" includes animals such as mammals or birds. Preferably, the subject is a mammal.

More preferably, the subject is a human. Even more preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The present invention relates to methods, compounds, compositions and kit for preventing and/or treating pulmonary fibrosis, liver fibrosis, heart fibrosis or skin fibrosis in a subject in need thereof.

The term "pulmonary fibrosis" or "lung fibrosis" means the formation or development of excess fibrous connective tissue (fibrosis) in the lung thereby resulting in the development of scarred (fibrotic) tissue. More precisely, pulmonary fibrosis is a chronic disease that causes swelling and scarring of the alveoli and interstitial tissues of the lungs. The scar tissue replaces healthy tissue and causes inflammation. This chronic inflammation is, in turn, the prelude to fibrosis. This damage to the lung tissue causes stiffness of the lungs which subsequently makes breathing more and more difficult.

Pulmonary fibrosis is a complicated illness that can arise from many different causes which include microscopic damage to the lungs induced by inhalation of small particles (asbestos, ground stone, metal dust, particles present in cigarette smoke, silica dust, etc). Alternatively, pulmonary fibrosis may arise as a secondary effect of other diseases (autoimmune disease, viral or bacterial infections, etc). Certain drugs such as cytotoxic agents (e.g. bleomycin, busulfan and methotrexate); antibiotics (e.g. nitrofurantoin, sulfasalazine); antiarrhythmics (e.g. amiodarone, tocainide); anti-inflammatory medications (e.g. gold, penicillamine); illicit drugs (e.g. crack, cocaine, heroin); also can cause pulmonary fibrosis. However, when pulmonary fibrosis appears without a known cause, it is termed as "idiopathic" or idiopathic pulmonary fibrosis (IPF).

Pulmonary fibrotic disorders is thought to begin with acute injury to the pulmonary parenchyma, leading to chronic interstitial inflammation, then to fibroblast activation and proliferation, and finally progressing to the common endpoint of pulmonary fibrosis and tissue destruction. Current research indicates that inflammation is less important in IPF, which appears to be primarily a disorder of fibroblast activation and proliferation in response to some as yet unknown trigger(s). Broadly, the manifestations of fibrotic lung disease can be grouped as follows: they may be chronic, insidious, and slowly progressive; they may be sub-acute, with a resolving, remitting, relapsing, or progressive course; and they may be acute, with a fulminant, progressive, remitting, or resolving course. Disorders with chronic, insidious, and slowly progressive courses are those that clinically resemble IPF and usually share a common pathology (i.e., UIP). Many of the connective-tissue diseases (e.g. rheumatoid arthritis; CREST syndrome (calcinosis cutis, Raynaud's syndrome, esophageal motility disorder, sclerodactyly, and telangiectasia); syndrome/progressive systemic scleroderma; systemic lupus erythematosus; mixed connective-tissue disease; pneumoconioses (e.g. asbestosis, silicosis); chronic hypersensitivity pneumonitis; and drug-related pulmonary fibrosis (e.g. due to bleomycin) generally fit into this category. Development of clinically apparent lung diseases related to occupational exposures (e.g. pneumoconiosis) generally occurs many years after the exposure. Radiation fibrosis often develops months to years after radiation exposure. A lag time of months or years can occur between the use of pulmonary toxic medications and the development of fibrotic disease. The effect can be dose-dependent (e.g. bleomycin), although, in other cases, the relationship is less clear. Pulmonary manifestations of connective-tissue disease may develop in advance of, coincident with, or many years after the onset of articular disease. Pulmonary sarcoidosis, although sometimes acute or sub-acute in onset, in some cases may present insidiously over time. Sub-acute presentations with a variable course are typified by cryptogenic organizing pneumonia (COP). COP often develops weeks or months after the onset of a flulike illness. The course is variable and may either spontaneously remit or progress. The disorder is thought to be very responsive to steroid therapy, although it may recur when steroids are withdrawn or tapered. In some cases, COP may progress to end-stage fibrotic lung disease. Disorders with an acute onset are typified by acute interstitial pneumonitis (AIP), which is an idiopathic form of severe lung injury. The histopathology is that of adult respiratory distress syndrome with diffuse alveolar damage. Patients present either with no antecedent history of lung disease or as part of an accelerated phase of underlying interstitial disease. Most patients progress rapidly to respiratory failure. Some patients may improve with steroids or other immunosuppressive therapy.

The term "liver fibrosis" means the formation or development of excess fibrous connective tissue (fibrosis) in the liver thereby resulting in the development of scarred (fibrotic) tissue. The scarred tissue replaces healthy tissue by the process of fibrosis and leads to subsequent cirrhosis of the liver.

The term "skin fibrosis" or "dermal fibrosis" means the excessive proliferation of epithelial cells or fibrous connective tissue (fibrosis) thereby resulting in the development of scarred (fibrotic) tissue. The scarred tissue replaces healthy tissue by the process of fibrosis and may be the prelude of systemic scleroderma. Skin fibrosis is intended to cover the fibrosis of any skin tissue and epithelial cells including, without limitation, blood vessels and veins, internal cavity of an organ or a gland such as ducts of submandibular, gallbladder, thyroid follicles, sweat gland ducts, ovaries, kidney; epithelial cells of gingival, tongue, palate, nose, larynx, oesophagus, stomach, intestine, rectum, anus and vagina; derma, scar, skin and scalp. The compounds of the present invention are active for promoting healing of wound and one or more of the following activities:

improving collagen organization and/or reducing wound cellularity in said wound;

reducing collagen overproduction by fibroblast and epithelial cells in said wound;

reducing epithelial mesenchymal transition in said wound;

reducing fibroblast migration and activation in said wound;

reducing and/or inhibiting dermal thickening in said wound;

reducing and/or inhibiting recruitment of inflammatory cells to said wound.

The term "cardiac fibrosis" or "heart fibrosis" means an abnormal thickening of the heart valves due to inappropriate proliferation of cardiac fibroblasts but more commonly refers to the proliferation of fibroblasts in the cardiac muscle. Fibrocyte cells normally secrete collagen, and function to provide structural support for the heart. When overactivated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

In general, prophylactic and therapeutic uses comprise the administration of a compound as described herein to a subject, preferably a human patient in need thereof.

The compounds according to the invention may be administered in combination with a therapeutically effective amount of a second compound which can be comprised in the same pharmaceutical composition or in a second pharmaceutical composition. The second compound is advantageously an immunosuppressive drug including, but not limited to, cyclosporine, azathioprine, cyclophosphamide, or mycophenolate mofetil; an anti-inflammatory drug including, but not limited to, corticosteroid (e.g. prednisone), a cytokine including but not limited to, interferon-alpha, interferon gamma, interleukine 12; a monoclonal antibody including but not limited to CTGF, TGF-$\beta$, MCP-1, IL-4 and IL-13; a multiple receptor tyrosine kinase inhibitor including, but not limited to, Nintedanib and the JNK (kinase) inhibitor Tanzisertib (CC-930); an antioxidant such as, but not limited to, N-acetylcysteine, pirfenidone, vitamin E, S-adenosyl methionine, or penicillamine; an enzyme inhibitor including, but not limited, to Lysyloxidase-like-2 (LOXL2 enzyme; an integrin inhibitor such as, but not limited to, $\alpha_v\beta_6$; a lipid receptor modulator including, but not limited to, lysophosphatidic acid receptor antagonists; or a thiazolindione or pirfenidone.

A related aspect of the invention concerns pharmaceutical compositions and kits which comprise one or more of the compounds of the invention described herein. As indicated herein above, the compounds of the invention may be useful in preventing and/or treating pulmonary fibrosis, liver fibrosis, hear fibrosis and skin fibrosis.

A related aspect of the invention concerns the prophylactic and therapeutic uses of a compound in related to pulmonary fibrosis, liver fibrosis, heart fibrosis and skin fibrosis. Pulmonary fibrosis can lead to several severe complications. Because the fibrotic lungs have impaired oxygen intake capacity, low blood oxygen levels (hypoxemia) can develop. Lack of oxygen can affect the entire body. Another complication of pulmonary fibrosis is pulmonary hypertension (high blood pressure in the arteries of the lungs). Scar tissue in the lungs can make it more difficult for blood to flow through them. The increased pressure makes the heart work harder and leads to a weakened and enlarged heart, reducing its pumping efficiency and producing heart failure. This is suspected when people develop fluid accumulations in the abdomen, leg swelling, or prominent pulsations in neck veins.

Liver fibrosis can lead to severe malfunction of the liver and can result in complete non-functioning of the liver.

Skin fibrosis can lead to hash mark, permanent cicatrix and scar causing severe esthetic problems and stiffness of the skin following a skin injury from a surgery or an accident.

Cardiac fibrosis can lead to severe malfunction of the heart and to death.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g., bioavailability, stability, potency, toxicity, etc.), and the particular disorder(s) the subject is suffering from. In addition, the therapeutically effective amount that is administered intravenously may depend on the subject's blood parameters e.g., lipid profile, insulin levels, glycemia or liver metabolism. The therapeutically effective amount will also vary according to the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained. The dose for oral administration of the compounds according to the invention in human is between 1 to 50 mg/kg, preferably 5 to 20 mg/kg, more preferably 5 to 15 mg/kg, also more preferably about 1 to 10 mg/kg in human. The dose of topical administration of the compounds of the present invention in human is between 0.01 to 10% (w/w), preferably 0.1 to 5% (w/w), and more preferably 1 to 5%. The metabolism of a mouse eliminates any compound faster than human metabolism, such that for testing of a compound in mice, the dose may be multiplied 10 times to 20 times.

As used herein, the term "pharmaceutical composition" refers to the presence of at least one compound according to the invention and a pharmaceutically acceptable vehicle.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (e.g. glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In some embodiments, the composition of the present invention comprises an effective amount of a compound of the formula herein above. Particularly preferred are the sodium salts of 3-pentylphenylacetic acid, 3-hydroxy-5-pentylphenylacetic acid and 3-fluoro-5-pentylphenylacetic acid.

In some embodiments, the invention pertains to pharmaceutical compositions for preventing and/or treating pulmonary fibrosis, liver fibrosis, heart fibrosis and skin fibrosis.

The compounds of the invention may be formulated prior to administration into pharmaceutical compositions using available techniques and procedures. For instance, the pharmaceutical compositions may be formulated in a manner suitable for administration by topical, oral, intravenous (iv), intramuscular (im), depo-im, subcutaneous (sc), depo-sc, sublingually, intranasal, intrathecal topical or rectal routes.

Preferably, the compound(s) of the invention can be orally administered or topically administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g., an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g., hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical preparation suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). For instance, metal salts of the compounds of this invention are expected to have physical chemical properties amenable with the preparation of fine particles of active pharmaceutical ingredient (API) for administration by inhalation but not the free acid form of these compounds. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention may also be administered topically to a subject, e.g., by the direct laying on or spreading of the composition on the epidermal or epithelial tissue of the subject, or transdermally via a "patch". Such compositions include, for example, lotions, creams, solutions, gels, emulsions and solids. These topical compositions may comprise an effective amount, usually about 0.01% to about 10% (w/w), or from about 0.1% to about 5% (w/w), or from about 1% to about 5% (w/w), of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like. The carrier may include vernix. Topical formulation includes one or more excipients such as, but not limited to, protectives, adsorbents, demulcents, emollients, preservatives, antioxidants, moisturizers, buffering agents, solubilizing agents, skin-penetration agents, and surfactants. Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide. Suitable demulcents include, but are not limited to, benzoin, hydroxypropyl cellulose, hydroxypropyl methylcellulose, and polyvinyl alcohol. Suitable emollients include, but are not limited to, animal and vegetable fats and oils, myristyl alcohol, alum, and aluminum acetate. Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other anti-microbial agents such as chlorhexidine, chlorocresol, benzoic acid and polymyxin. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, acetate buffers, citrate buffers, phosphate buffers, lactic acid buffers, and borate buffers. Suitable solubilizing agents include, but are not limited to, quaternary ammonium chlorides, cyclodextrins, benzyl benzoate, lecithin, and polysorbates. Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

Other compositions useful for attaining systemic delivery of the subject agents may include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound according to the present invention may also be administered parenterally, intraperitoneally, intraspinally, or intracerebrally. For such compositions, the compound of the invention can be prepared in glycerol, liquid polyethylene glycols, and mixtures thereof and in oils. Under ordinary conditions of storage and use, this preparation may contain a preservative to prevent the growth of microorganisms.

For the method of prevention/slowing progression/treatment of pulmonary fibrosis, liver fibrosis, heart fibrosis or skin fibrosis, the method of the present invention may also include co-administration of the at least one compound according to the invention, or a pharmaceutically acceptable salt thereof together with the administration of another therapeutically effective agent for the prevention and/or slowing the progression and/or treatment of pulmonary fibrosis, liver fibrosis, heart fibrosis or skin fibrosis. Accordingly, the invention also relates to a method for preventing, reducing or eliminating a symptom or complication of any one of the above mentioned diseases or conditions. The method comprises the administration of the compound of the present invention to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of formula I. The second agent may be selected from the list of compounds given herein above.

The present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The invention is further illustrated by the following examples, which should not be construed as further limiting.

EXAMPLES

The examples set forth herein below provide exemplary methods for the preparation of certain representative compounds encompassed by Formula I. Some Examples provide exemplary uses of certain representative compounds of the invention. Also provided are exemplary methods for assaying the compounds of the invention for efficacy.

Example 1: Experimental Procedure for the Preparation of the Sodium Salt of 3-pentylphenylacetic Acid (Compound I) Instrumentation All HPLC chromatograms and mass spectra were recorded on an HP 1100 LC-MS Agilent instrument using an analytical C18 column (250×4.6 mm, 5 microns) with a gradient over 5 min of 50-99% $CH_3CN$—$H_2O$ with 0.01% TFA as the eluant and a flow of 2 mL/min or a gradient over 3 min of 50-99% $CH_3CN$—$H_2O$ with 0.01% TFA as the eluant followed by isocratic over 3 min and a flow of 2 mL/min.

Compound I: Synthesis Using Modified Procedure of Sonogashira:

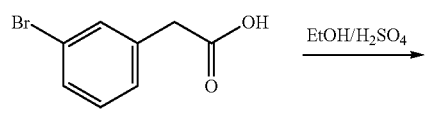

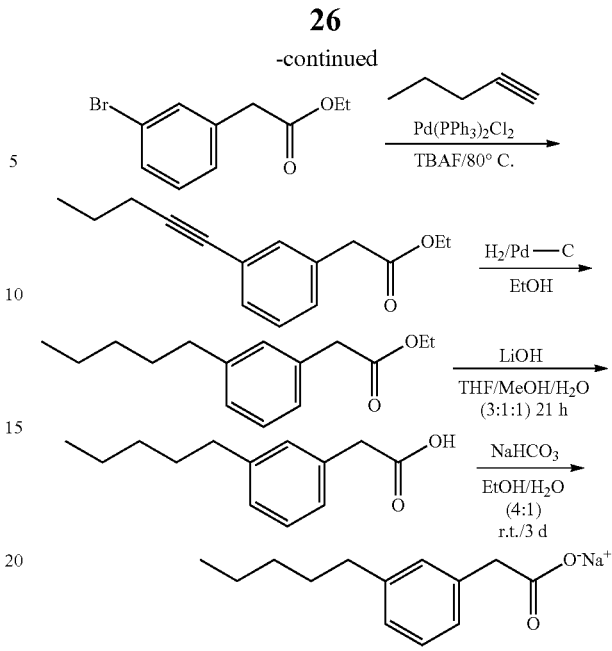

Step 1:

To a solution/suspension of 3-bromophenylacetic acid (5.02 g, 23.33 mmol) in ethanol (100 mL) at room temperature was added concentrated sulfuric acid (1 mL). The colorless solid was then stirred overnight at 80° C. The solution was concentrated under reduced pressure. The residue was diluted with ethyl acetate (25 mL), water (25 mL) and the two layers were separated. The aqueous layer was extracted with 2× ethyl acetate (25 mL) and brine (20 mL). The combined organic layers were washed with 2× saturated solution of sodium bicarbonate (25 mL), brine (25 mL) and dried over sodium sulfate. After filtration the solution it was evaporated to dryness. This gave light yellow oil (5.4 g, 95%). $^1$H-NMR (400 MHz, $CDCl_3$): δ 1.26 (t, J=4.7 Hz, 3H), 3.57 (s, 2H), 4.15 (Q, J=7.0 and 14.3 Hz, 2H), 7.17-7.26 (m, 2H), 7.38-7.44 (m, 1H), 7.44 (d, J=1.56 Hz, 1H).

Step 2:

A mixture of ethyl (3-bromophenyl)acetate (0.3 g, 1.24 mmol) and tetrabutylammonium fluoride hydrate (0.97 g, 3.72 mmol), was treated with $PdCl_2(PPh_3)_2$ (26 mg, 0.037 mmol; 3 mole %) and 1-pentyne (367 μl, 3.72 mmol) in a sealed tube. The tube was heated at 80° C. for 2 h. The mixture was treated with water, and was extracted with diethyl ether. The organic extract was dried over sodium sulfate, filtered and evaporated in vacuo to give the crude product. Purification on a Biotage™ 25M column (silica), eluting with ethyl acetate/hexane 0:1 to 2:98, gave ethyl (3-(pentyne-1-yl)phenyl)acetate as a pale yellow oil (0.23 g, 79%).

Step 3:

To ethyl[3-[pentyne-1-yl]phenyl]-acetate (0.23 g, 0.98 mmol) in ethanol (5 mL) under nitrogen atmosphere was added Pd on carbon (10%, 25 mg, 10% w/w). The mixture was vigorously stirred under hydrogen atmosphere at room temperature overnight. The solution was filtered and the palladium/carbon was washed with ethanol (20 mL). The filtrate was concentrated with silica gel. The crude product was purified by flash chromatography using a mixture of 10% hexanes/ethyl acetate. A clear oil was obtained (0.21 g, 90%).

Step 4:

To a solution of the ester (0.2 g, 0.9 mmol) in tetrahydrofuran (5 mL), methanol (1.5 mL) and water (1.5 mL) was added lithium hydroxide (0.09 g, 3.6 mmol) at 0° C. The reaction mixture was stirred overnight at room temperature. Insolubles were filtered and the filtrate was concentrated under reduced pressure. The residue was then treated with 2M hydrochloric acid and extracted with ethyl acetate. The organic phase was dried over sodium sulfate and evaporated under reduced pressure. The crude material was purified on a Biotage™ 40M column (silica), eluting with 40% ethyl acetate/hexanes. This gave pure (3-pentylphenyl)acetic acid (0.19 g, 99%) as a white gummy solid. $^1$H NMR (400 MHz, CD$_3$OD): δ 0.90 (t, J=7.0 Hz, 3H), 1.28-1.38 (m, 4H), 1.61 (qt, J=7.6 Hz, 15.0 Hz, 2H), 2.58 (t, J=7.6 Hz, 2H), 3.56 (s, 2H), 7.07 (m, 3H), 7.20 (m, 1H); LRMS (ESI): m/z 207 (MH$^+$); HPLC: 4.3 min.

Step 5:

To a stirred solution of the acid (0.19 g, 0.82 mmol) in ethanol (4 mL) and water (1 mL) was added sodium bicarbonate (0.07 g, 0.82 mmol). The reaction mixture was stirred at room temperature overnight. The solvent was evaporated and the white gummy solid was dissolved in water and the solution was lyophilized. This gave pure sodium salt of (3-pentylphenyl)acetic acid (0.17 g, 92%) as a white solid. mp 110-112° C.; $^1$H NMR (400 MHz, CD$_3$OD): δ 0.89 (t, J=6.8 Hz, 3H), 1.28-1.37 (m, 4H), 1.60 (qt, J=7.4 Hz, 15.0 Hz, 2H), 2.56 (t, J=7.6 Hz, 2H), 3.43 (s, 2H), 6.96 (m, 1H), 7.12 (m, 3H); LRMS (ESI): m/z 207 ((MH$^+$); HPLC: 4.3 min.

Example 2: Experimental Procedure for the Preparation of the Sodium Salt of 3-hydroxy-5-pentylphenylacetic Acid (Compound II)

Step 1:

A solution of methyl [3,5-dihydroxyphenyl]acetate (2.1 g, 11.5 mmol) in acetone (100 mL) was treated with potassium carbonate (2.4 g, 17.4 mmol), potassium iodide (383 mg, 2.31 mmol) and benzyl bromide (1.5 mL, 12.7 mmol), and the mixture was stirred at room temperature overnight. The reaction was diluted with water and extracted with dichloromethane (×3). Combined organic extracts were dried over sodium sulfate and evaporated in vacuo. The crude material was purified on a Biotage™ 40M column (silica), eluting with 40% ethyl acetate/hexane, to give methyl [3-benzyloxy-5-hydroxyphenyl]acetate (1.0 g, 33%). $^1$H NMR (400 MHz, CDCl$_3$): δ 7.32-7.42 (m, 5H), 6.48 (d, J=1.4 Hz, 1H), 6.38-6.39 (m, 2H), 4.99 (s, 2H), 3.69 (s, 3H), 3.53 (s, 2H).

Step 2:

A solution of the benzyl ether (1.04 g, 3.8 mmol) in dichloromethane (15 mL) at 0° C., was treated with N-phenyl-bis(trifluorosulfonyl)imide (1.40 g, 3.9 mmol), and then triethylamine (0.6 mL, 4.1 mmol) was added slowly. The reaction was stirred at 0° C. for 1 h, and then at room temperature for 1 h. The reaction mixture was diluted with water, and then extracted with diethylether (×2). Combined organic extracts were washed with 1M aqueous sodium hydroxide, water (×2) and saturated aqueous sodium chloride, then dried over sodium sulfate, filtered and evaporated in vacuo, to give the crude product. Purification on a Biotage™ 40M column (silica), eluting with 25% ethyl acetate/hexane, gave methyl [3-benzyloxy-5-trifluoromethanesulfonyloxyphenyl]acetate (1.2 g, 79%). $^1$H NMR (400 MHz, CDCl$_3$): δ 7.36-7.46 (m, 5H), 6.98 (s, 1H), 6.97 (s, 1H), 6.84 (s, 1H), 5.06 (s, 2H), 3.72 (s, 3H), 3.63 (s, 2H).

Step 3:

A solution of E-1-penten-1-ylboronic acid pinacol ester (0.8 g, 3.9 mmol) in dimethoxyethane (5 mL) was treated with a solution of the triflate (1.2 g, 3.0 mmol) in dimethoxyethane (5 mL). The solution was treated with palladium zero (0.7 g, 0.6 mmol) and 2M aqueous sodium carbonate (1.3 mL, 2.6 mmol). The mixture was then heated at 90° C. for 3 days. The reaction was cooled to room temperature and filtered through celite. The filtrate was evaporated in vacuo, and the crude material was purified on a Biotage™ 25M column (silica), eluting with 5% ethyl acetate/hexane, to give methyl [3-benzyloxy-5-[pent-1-enyl] phenyl]acetate (0.4 g, 40%). $^1$H NMR (400 MHz, CDCl$_3$): δ 7.36-7.47 (m, 5H), 6.90-6.92 (m, 2H), 6.79 (dd, J=2.0, 2.0 Hz, 1H), 6.35 (d, J=15.9 Hz, 1H), 6.24 (dt, J=15.9, 6.8 Hz, 1H), 5.07 (s, 2H), 3.70 (s, 3H), 3.59 (s, 2H), 2.20 (td, J=7.4, 6.8 Hz, 2H), 1.51 (dt, J=7.4 Hz, 2H), 0.98 (t, J=7.4 Hz, 3H).

Step 4:

A solution of the alkene (0.4 g, 1.2 mmol) in ethanol (13 mL) was treated with 1% palladium on carbon (40 mg). The mixture was stirred under 1 atm. of hydrogen at room temperature overnight. The reaction was filtered, evaporated in vacuo, and purified on a Biotage™ 25S column (silica), eluting with 15% ethyl acetate/hexane, to give methyl [3-hydroxy-5-pentylphenyl]acetate (0.3 g, 93%). $^1$H NMR (400 MHz, CDCl$_3$): δ 6.64 (s, 1H), 6.58-6.60 (m, 2H), 3.70 (s, 3H), 3.55 (s, 2H), 2.51 (t, J=7.7 Hz, 2H), 1.55-1.59 (m, 2H), 1.28-1.34 (m, 4H), 0.88 (t, J=7.0 Hz, 3H).

Step 5:

A solution of the ester (0.3 g, 1.3 mmol) in ethanol (12 mL) was treated with water (3 mL) and lithium hydroxide (155 mg, 6.4 mmol), and the mixture was stirred vigorously at room temperature overnight. The reaction mixture was diluted with water (100 mL); washed with dichloromethane; then acidified to pH 1 with 1M aqueous hydrochloric acid and extracted with dichloromethane (×3). Combined organic extracts were dried over sodium sulfate (0.3 g, 95%). This material was used without further purification. $^1$H NMR (400 MHz, CDCl$_3$): δ 6.66 (s, 1H), 6.58-6.59 (m, 2H), 3.55 (s, 2H), 2.52 (t, J=7.7 Hz, 2H), 1.55-1.59 (m, 2H).

Step 6:

A solution of the acid (0.27 g, 1.23 mmol) in ethanol (6 mL) and water (6 mL) was treated with a sodium bicarbonate (0.1 g, 1.2 mmol), and the reaction was stirred at room temperature for a few hours. Solvent was concentrated in vacuo, and the solution was diluted with water, filtered (0.2 m), and lyophilized to give sodium [3-hydroxy-5-pentylphenyl]acetate as a white solid (0.3 g, 95%). mp 63-66° C.; $^1$H NMR (400 MHz, CD$_3$OD): δ 6.63 (s, 1H), 6.58 (s, 1H), 6.42 (s, 1H), 3.36 (s, 2H), 2.48 (t, J=7.6 Hz, 2H), 1.55-1.62 (m, 2H), 1.26-1.38 (m, 4H), 0.89 (t, J=6.8 Hz, 3H); $^{13}$C NMR (101 MHz, CD$_3$OD): δ 177.79, 155.31, 142.36, 137.62, 119.08, 111.66, 111.18, 43.70, 34.17, 29.95, 29.56, 20.87, 11.64; LRMS (ESI): m/z 445.2 (2M-2Na$^+$3H$^+$), m/z 223 (M-Na$^+$+2H$^-$); HPLC: 3.5 min.

Example 3: Experimental Procedure for the Preparation of the Sodium Salt of 3-fluoro-5-pentylphenylacetic Acid (Compound III)

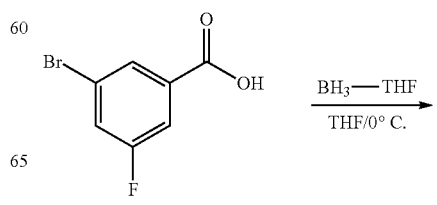

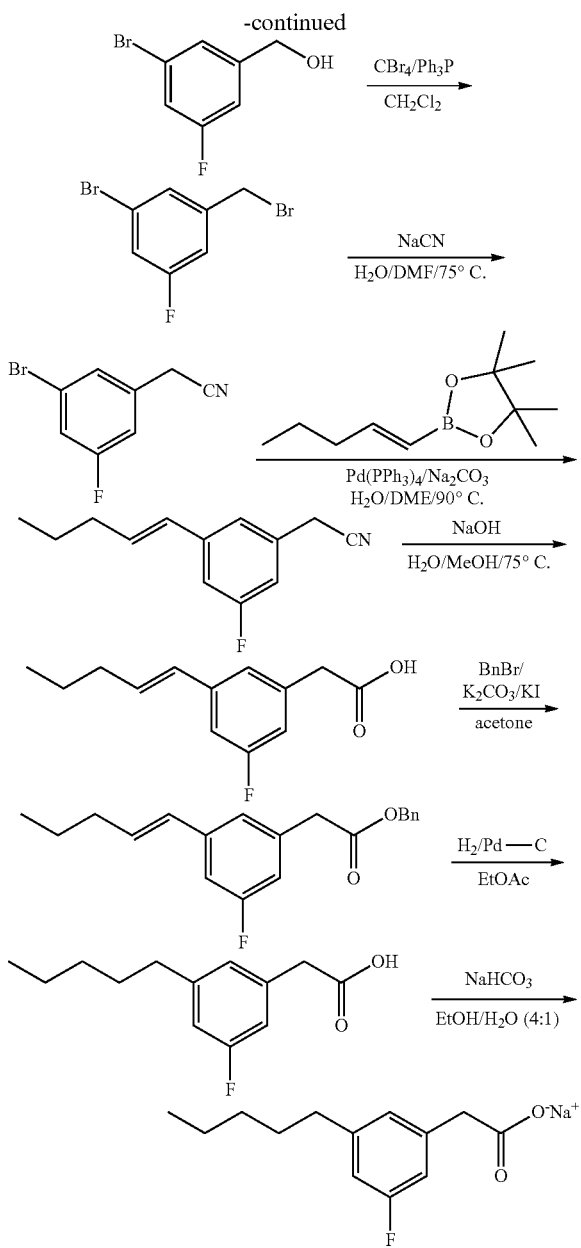

Hz, $J_{HH}$=unresolved, 1H), 4.66 (s, 2H), 2.04 (br s, 1H); $^{19}$F NMR (377 MHz, CDCl$_3$): δ −111.05 (dd, $J_{HF}$=9.3, 8.0 Hz, 1F); $^{13}$C NMR (101 MHz, CDCl$_3$): δ 162.87 (d, $J_{CF}$=250.6 Hz), 145.42 (d, $J_{CF}$=6.9 Hz), 125.45 (d, $J_{CF}$=3.1 Hz), 122.69 (d, $J_{CF}$=9.2 Hz), 118.01 (d, $J_{CF}$=24.6 Hz), 112.51 (d, $J_{CF}$=21.5 Hz), 63.60 (d, $J_{CF}$=2.3 Hz).

Step 2:

A solution of 3-bromo-5-fluorobenzyl alcohol (1.79 g, 8.39 mmol) and triphenylphosphine (3.65 g, 10.10 mmol) in dichloromethane (45 mL), was treated with carbon tetrabromide (3.34 g, 10.10 mmol) in small portions over 10 min, and the reaction was then stirred at room temperature overnight. Solvent was evaporated in vacuo, and the residue was treated with diethyleher (50 mL). The resultant white slurry was stirred at room temperature, and then filtered through celite. The residue was washed with diethylether (2×50 mL), and the combined filtrate and washings were evaporated in vacuo to give the crude product. Purification on a silica pad, eluting with 2% ethyl acetate/hexane, gave 3-bromo-5-fluorobenzyl bromide (2.21 g, 98%). $^1$H NMR (400 MHz, CDCl$_3$): δ 7.33 (s, 1H), 7.18 (ddd, JH$_F$=8.2 Hz, $J_{HH}$=2.0, 2.0 Hz, 1H), 7.05 (ddd, $J_{HF}$=9.0 Hz, $J_{HH}$=1.8, 1.6 Hz, 1H), 4.38 (s, 2H); $^{19}$F NMR (377 MHz, CDCl$_3$): δ −110.19 to −110.14 (m, 1F); $^{13}$C NMR (101 MHz, CDCl$_3$): δ 162.67 (d, $J_{CF}$=252.1 Hz), 141.61 (d, $J_{CF}$=8.5 Hz), 128.17 (d, $J_{CF}$=3.1 Hz), 122.94 (d, $J_{CF}$=10.0 Hz), 119.39 (d, $J_{CF}$=24.6 Hz), 115.34 (d, $J_F$=22.3 Hz), 31.31 (d, $J_{CF}$=2.3 Hz).

Step 3:

A suspension of sodium cyanide (0.38 g, 7.73 mmol) in water (0.35 mL) was treated with a solution of 3-bromo-5-fluorobenzyl bromide (1.38 g, 5.15 mmol) in dimethylformamide (2.6 mL), and the reaction was heated at 75° C. in a sealed tube for 3 h. The reaction was cooled to room temperature and was partitioned between ethyl acetate (50 mL) and 2.5% w/v aqueous sodium bicarbonate (100 mL). The aqueous phase was extracted with a further portion of ethyl acetate (50 mL); and the combined extracts were washed with water (2×50 mL) and with saturated aqueous sodium chloride (50 mL); dried over sodium sulfate; filtered, and evaporated in vacuo to give the crude product. Purification on a Biotage™ 40iM column (silica), eluting with 10% ethyl acetate/hexane, gave 2-[3-bromo-5-fluorophenyl] acetonitrile (0.64 g, 58%). $^1$H NMR (400 MHz, CDCl$_3$): δ 7.26-7.28 (m, 1H), 7.17-7.19 & 7.19-7.21 (dm, $J_{HF}$=8.0 Hz, $J_{HH}$=unresolved, 1H), 6.98-7.00 & 7.00-7.02 (dm, $J_{HH}$=8.8 Hz, $J_{111}$=unresolved, 1H), 3.73 (s, 2H); $^{19}$F NMR (377 MHz, CDCl$_3$): δ 109.46 (dd, $J_{HF}$=8.0, 8.0 Hz, 1F); $^{13}$C NMR (101 MHz, CDCl$_3$): δ 162.90 (d, $J_{CF}$=252.1 Hz), 133.95 (d, $J_{CF}$=8.5 Hz), 127.24 (d, $J_{CF}$=3.8 Hz), 123.53 (d, $J_{CF}$=10.0 Hz), 119.22 (d, $J_{CF}$=23.8 Hz), 117.00, 114.50 (d, $J_{CF}$=23.1 Hz), 23.30 (d, $J_{CF}$=1.5 Hz).

Step 4:

A solution of the aryl bromide (0.55 g, 2.58 mmol) and (E)-1-penten-1-ylboronic acid pinacol ester (0.61 g, 3.13 mmol) in dimethoxyethane (13 mL) was treated with a solution of sodium carbonate (0.55 g, 5.17 mmol) in water (3 mL). The solution was deoxygenated with nitrogen, and was treated with tetrakis(triphenylphosphine)palladium (0.15 g, 0.13 mmol; 5 mole %). The mixture was then heated at 90° C., in a sealed tube for 17 h. The reaction was cooled to room temperature and was partitioned between ethyl acetate (50 mL) and 1M aqueous hydrochloric acid (50 mL). The organic phase was washed with saturated aqueous sodium chloride (30 mL); dried over sodium sulfate; filtered, and evaporated in vacuo to give the crude product. Purification on a Biotage™ 40iM column (silica), eluting with Step 1:

A solution of 3-bromo-5-fluorobenzoic acid (2.74 g, 12.5 mmol) in tetrahydrofuran (6 mL), at 0° C. under nitrogen, was treated with borane-tetrahydrofuran complex (1M, 15 mL, 15 mmol) in small portions over 12 min, and the reaction was then stirred at 0° C. for 70 minutes, and at room temperature for 22 h. The reaction was quenched by addition of methanol (10 mL), and the methanolic mixture was stirred at room temperature for 3 h, and then evaporated in vacuo, with co-evaporation from methanol, then from ethyl acetate, to give the crude product. The material was dissolved in ethyl acetate (200 mL), and the solution was washed with 0.5M aqueous sodium hydroxide (200 mL), and with saturated aqueous sodium chloride (100 mL); then dried over sodium sulfate; filtered and evaporated in vacuo to give 3-bromo-5-fluorobenzyl alcohol (1.79 g, 67%). $^1$H NMR (400 MHz, CDCl$_3$): δ 7.29 (s, 1H), 7.15 (ddd, $J_{HF}$=8.2 Hz, $J_{HH}$=2.2, 1.8 Hz, 1H), 7.00-7.02 and 7.02-7.04 (dm, $J_{HF}$=9.2

(3%) ethyl acetate/hexane, gave (E)-2-[3-fluoro-5-[pent-1-enyl]phenyl]acetonitrile (0.43 g, 82%). $^1$H NMR (400 MHz, CDCl$_3$): δ 7.04 (s, 1H), 6.97 (ddd, $J_{HF}$=9.8 Hz, $J_{HH}$=2.0, 1.5 Hz, 1H), 6.82-6.85 (m, 1H), 6.31 (d, J=15.8 Hz, 1H), 6.25 (ddd, J=15.8, 5.9, 0 Hz, 1H), 3.68 (s, 2H), 2.18 (td, J=7.2, 5.4 Hz, 2H), 1.49 (qt, J=7.4, 7.4 Hz, 2H), 0.95 (t, J=7.4 Hz, 3H); $^{19}$F NMR (377 MHz, CDCl$_3$): δ −112.93 (dd, $J_{HF}$=10.6, 9.3 Hz, 1F); $^{13}$C NMR (101 MHz, CDCl$_3$): δ 163.43 (d, $J_{CF}$=246.0 Hz), 141.44 (d, $J_{CF}$=8.5 Hz), 133.99, 132.37 (d, $J_{CF}$=8.5 Hz), 128.42 (d, $J_{CF}$=2.3 Hz), 121.60 (d, $J_{CF}$=3.1 Hz), 117.66, 113.40 (d, $J_{CF}$=23.1 Hz), 112.21 (d, $J_{CF}$=22.3 Hz), 35.22, 23.49 (d, $J_{CF}$=2.3 Hz), 22.51, 13.94.

Step 5:

A solution of the phenylacetonitrile derivative (0.43 g, 2.10 mmol) in methanol (42 mL) was treated with aqueous sodium hydroxide (5M; 21 mL, 105 mmol), and the mixture was heated at 75° C. in a sealed tube for 4.5 h. The reaction mixture was cooled to room temperature, and was quenched with 6M aqueous hydrochloric acid (21 mL); stirred at room temperature for 10 min; then extracted with ethyl acetate (2×75 mL). The organic extract was washed with saturated aqueous sodium chloride (75 mL); dried over sodium sulfate; filtered, and evaporated in vacuo to give the crude product. Purification on a Biotage™ 40iM column (silica), eluting with 70% ethyl acetate/hexane, gave the methyl ester of the desired product (0.09 g, 18%), and ~95% pure (E)-2-[3-fluoro-5-[pent-1-enyl]phenyl]acetic acid (0.22 g, 48%). $^1$H NMR (400 MHz, CDCl$_3$): δ 11.17 (br s, 1H), 7.02 (s, 1H), 6.98 (ddd, $J_{HF}$=9.8 Hz, $J_{HH}$=2.0, 1.8 Hz, 1H), 6.85 (ddd, $J_{HF}$=9.0 Hz, $J_{HH}$=1.8, 1.6 Hz, 1H), 6.33 (d, J=15.8 Hz, 1H), 6.25 (dt, J=15.8, 6.4 Hz, 1H), 3.62 (s, 2H), 2.17-2.22 (m, 2H), 1.51 (qt, J=7.4, 7.4 Hz, 2H), 0.96 (t, J=7.4 Hz, 3H); $^{19}$F NMR (377 MHz, CDCl$_3$): δ −114.10 (dd, $J_{HF}$=9.3, 9.3 Hz, 1F).

Step 6:

A solution of the partially-purified acid (0.28 g, 1.26 mmol) in acetone (5 mL) was treated with potassium carbonate (0.26 g, 1.90 mmol), potassium iodide (0.04 g, 0.25 mmol) and benzyl bromide (0.18 mL, 1.5 mmol), and the reaction was stirred at room temperature for 18 h. The reaction mixture was partitioned between ethyl acetate (25 mL) and 1M aqueous hydrochloric acid (25 mL). The organic phase was then washed with saturated aqueous sodium chloride (25 mL); dried over sodium sulfate; filtered, and evaporated in vacuo to give the crude product. Purification on a Biotage™ 40iM column (silica), eluting with 5% ethyl acetate/hexane gave benzyl (E)-2-[3-fluoro-5-[pent-1-enyl]phenyl]acetate (0.3 g, 75%). $^1$H NMR (400 MHz, CDCl$_3$): δ 7.32-7.40 (m, 5H), 7.03 (s, 1H), 6.97 (ddd, $J_{HF}$=10.0 Hz, $J_{HH}$=2.3, 1.5 Hz, 1H), 6.86 (ddd, $J_{HF}$=9.0 Hz, $J_{HH}$=2.0, 1.7 Hz, 1H), 6.33 (d, J=15.8 Hz, 1H), 6.23 (dt, J=15.8, 6.5 Hz, 1H), 5.16 (s, 2H), 3.64 (s, 2H), 2.17-2.23 (m, 2H), 1.52 (qt, J=7.4, 7.4 Hz, 2H), 0.97 (t, J=7.4 Hz, 3H); $^{19}$F NMR (377 MHz, CDCl$_3$): δ −114.34 (dd, $J_{HF}$=9.3, 9.3 Hz, 1F); $^{13}$C NMR (101 MHz, CDCl$_3$): δ 171.08, 163.32 (d, $J_{CF}$=244.4 Hz), 140.65 (d, $J_{CF}$=7.7 Hz), 136.17 (d, $J_{CF}$=8.5 Hz), 135.93, 133.05, 128.95 (d, $J_{CF}$=3.1 Hz), 128.84, 128.52 (d, $J_{CF}$=9.2 Hz), 128.48, 123.09 (d, $J_{CF}$=2.3 Hz), 114.78 (d, $J_{CF}$=22.3 Hz), 111.46 (d, $J_{CF}$=22.3 Hz), 67.04, 41.26 (d, $J_{CF}$=1.5 Hz), 35.27, 22.63, 14.00.

Step 7:

A solution of the benzyl ester (0.16 g, 0.50 mmol) in ethyl acetate (2 mL) was treated with palladium on carbon (1% w/w Pd; 15 mg). The mixture was degassed with hydrogen, and was stirred under 1 atmosphere of hydrogen at room temperature overnight. The reaction was filtered, and evaporated in vacuo to give 2-[3-fluoro-5-pentylphenyl]-acetic acid (0.11 g, 97%). 1H NMR (400 MHz, CDCl$_3$): δ 11.47 (br s, 1H), 6.89 (s, 1H), 6.81-6.86 (m, 2H), 3.62 (s, 2H), 2.60 (t, J=7.8 Hz, 2H), 1.58-1.66 (m, 2H), 1.28-1.41 (m, 4H), 0.92 (t, J=6.8 Hz, 3H); $^{19}$F NMR (377 MHz, CDCl$_3$): δ −114.34 (dd, $J_{HF}$=9.3, 9.3 Hz, 1F); $^{13}$C NMR (101 MHz, CDCl$_3$): δ 178.15, 163.08 (d, $J_{CF}$=246.0 Hz), 145.02 (d, $J_{CF}$=7.7 Iz), 135.04 (d, $J_{CF}$=8.5 Hz), 125.49 (d, $J_{CF}$=2.3 Hz), 114.49 (d, $J_{CF}$=20.8 Hz), 113.83 (d, $J_{CF}$=22.3 Hz), 41.01 (d, $J_{CF}$=1.5 Hz), 35.87 (d, $J_{CF}$=1.5 Hz), 31.67, 31.03, 22.74, 14.24.

Step 8:

A solution of the acid (0.11 g, 0.49 mmol) in ethanol (3 mL) was treated with a solution of sodium bicarbonate (0.041 g, 0.49 mmol) in water (0.75 mL), and the reaction was stirred at room temperature for 17 h. Ethanol was evaporated in vacuo, and the residual aqueous syrup was diluted with water (10 mL), filtered (0.2 μm), and lyophilised to give sodium 2-[3-fluoro-5-pentylphenyl]acetate as a white solid (0.12 g, 99%). mp 120-123° C.; $^1$H NMR (400 MHz, CD$_3$OD): δ 6.94 (s, 1H), 6.87 (ddd, $J_{HF}$=9.8 Hz, $J_{HH}$=2.0, 2.0 Hz, 1H), 6.70 (ddd, $J_{HF}$=10.0 Hz, $J_{HH}$=2.0, 2.0 Hz, 1H), 3.45 (s, 2H), 2.56 (t, J=7.7 Hz, 2H), 1.58-1.63 (m, 2H), 1.26-1.39 (m, 4H), 0.90 (t, J=7.0 Hz, 3H); $^{19}$F NMR (377 MHz, CD$_3$OD): δ −117.54 (dd, $J_{HF}$=10.0, 10.0 Hz, 1F); $^{13}$C NMR (101 MHz, CD$_3$OD): δ 178.66, 163.04 (d, $J_{CF}$=242.9 Hz), 145.07 (d, $J_{CF}$=7.7 Hz), 140.42 (d, $J_{CF}$=8.5 Hz), 125.03 (d, $J_{CF}$=2.3 Hz), 112.99 (d, $J_{CF}$=22.3 Hz), 112.30 (d, $J_{CF}$=20.8 Hz), 44.96, 35.53 (d, $J_{CF}$=1.5 Hz), 31.46, 31.00, 22.45, 13.30; HPLC: 1.2 min.

Example 4: Compound IV, Sodium Salt of E-(3-pent-1-enyl-phenyl)acetic Acid

The above compound was prepared as for compound I starting with E-(3-pent-1-enyl-phenyl)acetic acid methyl ester. The latter was prepared by reacting 3-bromophenyl acetic acid methyl ester with trans-1-pentenylboronic acid pinacol ester under Suzuki conditions. White solid; $^1$H NMR (400 MHz, CD$_3$OD): δ=7.32 (s, 1H), 7.11-7.18 (m, 31H), 6.35 (d, J=15.7 Hz, 1H), 6.20-6.27 (m, 1H), 3.44 (s, 2H), 2.19 (m, 2H), 1.45-1.54 (m, 2H), 0.96 (t, J=7.4, 3H); $^{13}$C NMR (101 MHz, CD$_3$OD): δ=179.26, 138.25, 137.92, 130.32, 130.04, 128.06, 127.59, 126.60, 123.52, 45.21, 35.06, 22.52, 12.89; LRMS (ESI): m/z 205 (MH$^+$); HPLC: 4.1 min.

Example 5: Compound V, Sodium Salt of (2-hydroxy-5-pentylphenyl)acetic Acid

The above compound was prepared as for compound I starting with 5-bromo-2-methoxyphenylacetic acid methyl ester. Demethylation of the methoxy group was undertaken using a solution of boron tribromide (1M/CH$_2$Cl$_2$) at −78° C. for 1 h then at 0° C. during 20 min. White solid; $^1$H NMR (400 MHz, CD$_3$OD): δ=6.88 (m, 2H), 6.71 (d, J=8.6 Hz, 1H), 3.50 (s, 2H), 2.49 (t, J=7.6 Hz, 2H), 1.54-1.62 (m, 2H), 1.29-1.38 (m, 4H), 0.91 (t, J=7.0 Hz, 3H); $^{13}$C NMR (101 MHz, CD$_3$OD): δ=180.08, 154.04, 134.03, 130.26, 127.36, 124.15, 116.57, 42.48, 34.91, 31.60, 31.42, 22.45, 13.24; LRMS (ESI): m/z 177 (MH$^+$—CO—NaOH); HPLC: 3.7 min.

Example 6: Compound VI, Sodium Salt of 3-(4-fluoro-3-pentylphenyl)propionic Acid The above compound was prepared as for compound I starting with E-methyl 3-(3-bromo-4-fluorophenyl)acrylate. The latter was prepared by mixing a solution of 3-bromo- 4-fluorobenzaldehyde and ethoxycarbonylmethylenetriphenylphosphorane in dry dichloromethane at room temperature. White solid; $^1$H NMR (400 MHz, CD$_3$OD): δ=6.67-6.74 (m, 2H), 6.58 (m, 1H), 2.49 (t, J=7.6 Hz, 2H), 2.23 (t, J=7.4 Hz, 2H), 2.15 (m, 2H), 1.25 (m, 2H), 0.99-1.06 (m, 4H), 0.61 (t, J=6.7 Hz, 3H); $^{13}$C NMR (101 MHz, D$_2$O): δ=182.38, 160.69, 158.28, 137.37, 130.34, 129.58, 126.84, 114.99, 39.68, 31.51, 29.92, 28.90, 22.31, 16.66; LRMS (ESI): m/z 221 (MH$^+$—H$_2$O); HPLC: 4.5 min.

Example 7: Compound VII, Sodium Salt of 3-(3-pentylphenyl)propionic Acid

The above compound was prepared as for compound I starting with 3-Oxo-3-bromophenylpropionic acid ethyl ester. The ketone group and the double bond were simultaneously reduced using palladium/carbon in ethanol under hydrogen pressure. White solid; $^1$H NMR (400 MHz, CDCl$_3$): δ 7.14-7.10 (m, 1H), 7.04-7.00 (m, 2H), 6.95-6.93 (m, 1H), 2.88-2.84 (m, 2H), 2.55 (t, J=7.4 Hz, 2H), 2.44-2.40 (m, 2H), 1.63-1.55 (m, 2H), 1.35-1.28 (m, 4H), 0.90 (m, 3H); $^{13}$C NMR (101 MHz, CD$_3$OD): δ 179.3, 141.2, 140.8, 126.7, 126.4, 124.0, 123.8, 38.6, 34.2, 31.2, 29.9, 29.8, 20.9, 11.7; LRMS (ESI): m/z 203 (MH—CO—NaOH); HPLC: 4.5 min.

Example 8: Compound VIII, Sodium Salt of 2-(3-pentylphenyl)propionic Acid

The above compound was prepared as for compound I starting with 2-methyl-2-(3-pentylphenyl)malonic acid diethyl ester. The latter was prepared by reacting 2-(3-bromophenyl)malonic acid diethyl ester with methyl iodide followed by Suzuki coupling using trans-1-pentenyl-1-boronic acid pinacol ester then reduction of the double bond by hydrogenation. White solid; $^1$H NMR (400 MHz, CD$_3$OD): δ 7.19-6.95 (m, 4H), 3.54 (q, J=7.0 Hz, 1H), 2.56 (t, J=7.6 Hz, 2H), 1.64-1.56 (m, 2H), 1.38 (d, J=7.2 Hz, 3H), 1.37-1.20 (m, 4H), 0.90 (t, J=7.0 Hz, 3H); $^{13}$C NMR (CD$_3$OD): δ 182.2, 144.4, 142.5, 127.8, 127.6, 125.8, 124.7, 49.2, 35.9, 31.5, 31.3, 22.4, 19.0, 13.2; LRMS (ESI): m/z 221 (M-Na$^+$+2H$^+$); HPLC: 4.5 min.

Example 9: Compound IX, Sodium Salt of 2-Fluoro-2-(3-pentylphenyl)acetic Acid The above compound was prepared from ethyl 2-fluoro-2-(3-pentylphenyl)acetate as for example 1. The ester was prepared by reaction of ethyl 2-(3-pentylphenyl)acetate with lithium diisopropylamide and N-fluorobenzenesulfonimide at −78° C. in Tetrahydrofuran. White solid; $^1$H NMR (400 MHz, CD$_3$OD): δ 7.34 (s, 1H), 7.30 (dd, J=7.6, 1.4 Hz, 1H), 7.24 (dd, J=7.6, 7.6 Hz, 1H), 7.13 (dd, J=7.4, 1.0 Hz, 1H), 5.53 (d, J$_{HF}$=51.3 Hz, 1H), 2.60 (t, J=7.7 Hz, 2H), 1.59-1.65 (m, 2H), 1.27-1.39 (m, 4H), 0.76 (t, J=6.9 Hz, 3H); $^{13}$C NMR (101 MHz, CD$_3$OD): δ 173.73 (d, J$_{CF}$=23.9 Hz), 141.34, 136.37 (d, J$_{CF}$=20.0 Hz), 126.79 (d, J$_{CF}$=2.3 Hz), 126.40, 125.41 (d, J$_{CF}$=5.4 Hz), 122.84 (d, J$_{CF}$=5.4 Hz), 90.34 (d, J$_{CF}$=183.4 Hz), 34.13, 29.91, 29.65, 20.85, 11.64; $^{19}$F NMR (377 MHz, CD$_3$OD): δ −168.83 (d, J$_{HF}$=51.7 Hz, 1F); LRMS (ESI negative): m/z 223.0 (100%, M-Na$^+$); HPLC: 4.1 min.

Example 10: Compound X, Sodium Salt of 2-methyl-2-(3-pentylphenyl)propionic Acid

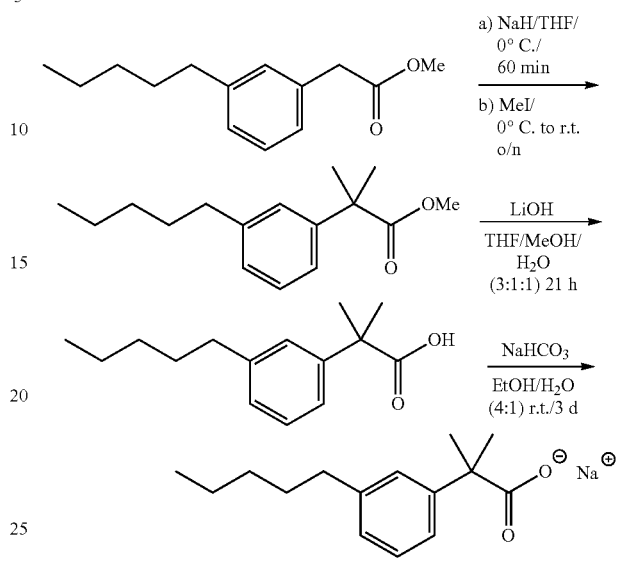

Step 1:

A suspension of sodium hydride (60% w/w in mineral oil; 0.5 g, 13.6 mmol) in anhydrous THF (8 mL) was cooled to 0° C., and was treated with a solution of methyl [3-pentylphenyl]acetate (1.0 g, 4.5 mmol) in anhydrous THF (4 mL). The reaction was stirred at 0° C. for 60 min, and was then treated with methyl iodide (0.7 mL, 11.3 mmol). The reaction was allowed to warm slowly to room temperature, and was stirred at this temperature overnight. The reaction was quenched by addition of saturated aqueous ammonium chloride (10 mL), and the mixture was extracted with ether (3×20 mL). Combined extracts were dried over magnesium sulfate and evaporated to dryness. Purification on a silica pad, eluting with ethyl acetate/hexane 1:99 then 2:98, gave methyl 2-methyl-2-(3-pentylphenyl) propionate as a colorless oil (0.68 g, 60%). $^1$H NMR (400 MHz, CD$_3$OD): δ 7.18-7.22 (m, 1H), 7.08-7.13 (m, 2H), 7.02-7.05 (m, 1H), 3.62 (s, 3H), 2.58 (t, J=7.6 Hz, 2H), 1.55-1.62 (m, 2H), 1.53 (s, 6H), 1.28-1.36 (m, 4H), 0.90 (t, J=7.1 Hz, 3H); HPLC: 5.5 min.

Step 2:

A solution of the ester in THF (8 mL), methanol (2 mL) and water (2 mL) was treated with lithium hydroxide (0.2 g, 8.2 mmol), and the reaction was stirred at room temperature overnight, then at 50° C. for 2 days, and at room temperature for 10 days. The reaction was filtered and the funnel was washed with methanol (2×20 mL). Combined filtrate and washings were treated with 2M hydrochloric acid (7 mL), and the mixture was extracted with ethyl acetate (3×40 mL). Combined extracts were washed with water (2×30 mL), dried over sodium sulfate, filtered and evaporated in vacuo, to give 2-methyl-2-(3-pentylphenyl) propionic acid as a pale yellow syrup (0.64 g, 99%). This material was used without further purification. $^1$H NMR (400 MHz, CDCl$_3$): δ 7.19-7.27 (m, 3H), 7.07-7.10 (m, 1H), 2.60 (t, J=7.8 Hz, 2H), 1.60 (s, 6H), 1.58-1.63 (m, 2H), 1.30-1.37 (m, 4H), 0.89 (t, J=7.0 Hz, 3H); LRMS (ESI): m/z 257 (MNa$^+$); HPLC: 4.7 min.

Step 3:

A solution of the acid in ethanol (16 mL) was treated with water (4 mL) and sodium bicarbonate (0.2 g, 2.7 mmol), and the reaction was stirred at room temperature for 3 days. Solvent was evaporated in vacuo, and the residue was dissolved in water, filtered and lyophilized to give sodium 2-methyl-2-[3-pentylphenyl]propionate as a white solid (0.7 g, 96%). $^1$H NMR (400 MHz, CD$_3$OD): δ 7.19-7.23 (m, 2H), 7.13 (dd, J=7.6, 7.6 Hz, 1H), 6.91-6.95 (m, 1H), 2.56 (t, J=7.7 Hz, 2H), 1.56-1.63 (m, 2H), 1.46 (s, 6H), 1.28-1.39 (m, 4H), 0.90 (t, J=7.0 Hz, 3H); $^{13}$C NMR (101 MHz, CD$_3$OD): δ 184.35, 148.62, 142.13, 127.51, 126.14, 125.32, 123.16, 36.01, 31.57, 31.40, 27.45, 22.44, 13.22; LRMS (ESI): m/z 235; (M-Na$^+$2H$^+$); HPLC: 4.6 min.

Example 11: Compound XI, Sodium Salt of 2-(3-Hexylphenyl)acetic Acid

The above compound was prepared by Suzuki coupling of methyl 2-(3-bromophenyl)acetate and (E)-hex-1-enylboronic acid pinacol ester as for example 2; followed by hydrogenation, ester hydrolysis and sodium salt formation as for example 1. White solid; $^1$H NMR (400 MHz, D$_2$O): δ 7.14 (dd, J=7.8, 7.6 Hz, 1H), 7.01 (s, 1H), 7.00 (d, J=7.8 Hz, 1H), 6.96 (d, J=7.6 Hz, 1H), 3.34 (s, 2H), 2.46 (d, J=7.5 Hz, 2H), 1.41-1.48 (m, 2H), 1.10-1.18 (m, 61H), 0.70 (t, J=6.8 Hz, 3H); $^{13}$C NMR (101 MHz, D$_2$O): δ 181.23, 143.98, 137.46, 129.47, 128.73, 126.63, 126.48, 44.58, 35.14, 31.12, 30.94, 28.23, 22.13, 13.53; LRMS (ESI): m/z 265 (100%, M+Na$^+$); HPLC: 4.6 min.

Example 12: Compound XII, Sodium Salt of 2-(3-(Hex-1-enyl]phenyl)acetic Acid The above compound was prepared by Suzuki coupling of methyl 2-(3-bromophenyl)acetate and (E)-hex-1-enylboronic acid pinacol ester as for example 2; followed by ester hydrolysis and sodium salt formation. White solid; $^1$H NMR (400M Hz, CD$_3$OD): δ 7.33 (s, 1H), 7.12-7.19 (m, 3H), 6.35 (d, J=15.8 Hz, 1H), 6.20 (dt, J=15.8, 6.8 Hz, 1H), 3.46 (s, 2H), 2.17-2.22 (m, 2H), 1.33-1.49 (m, 4H), 0.93 (t, J=7.2 Hz, 3H); $^{13}$C NMR (101 MHz, CD$_3$OD): δ 179.35, 138.27, 137.95, 130.27, 130.16, 128.10, 127.61, 126.64, 123.56, 45.24, 32.66, 31.67, 22.16, 13.22; LRMS (ESI): m/z 263 (100%, M+Na$^+$); HPLC: 4.4 min.

Example 13: Compound XIII, Sodium Salt of 2-(2-Fluoro-5-(pent-1-enyl)phenyl)acetic Acid The above compound was prepared from (E)-pent-1-enylboronic acid pinacol ester and ethyl 2-(5-bromo-2-fluorophenyl)acetate as for example 2. Melting point 215-220° C.; White solid; $^1$H NMR (400 MHz, D$_2$O): δ 7.12-7.17 (m, 2H), 6.90 (dd, J$_{HF}$=9.5 Hz, J$_{HH}$=9.5 Hz, 1H), 6.28 (d, J=16.0 Hz, 1H), 6.15 (dt, J=16.0, 6.8 Hz, 1H), 3.37 (s, 2H), 2.00-2.05 (m, 2H), 1.29-1.34 (m, 2H), 0.76 (t, J=7.4 Hz, 3H); $^{13}$C NMR (101 MHz, D$_2$O): δ 180.02, 160.30 (d, J$_{CF}$=243.5 Hz), 134.09 (d, J$_{CF}$=3.8 Hz), 131.99 (d, J$_{CF}$=1.5 Hz), 128.99 (d, J$_{CF}$=4.6 Hz), 128.49, 125.84 (d, J$_{CF}$=7.7 Hz), 124.60 (d, J$_{CF}$=17.0 Hz), 115.44 (d, J$_F$=21.6 Hz), 37.88 (d, J$_{CF}$=2.3 Hz), 34.56, 22.03, 13.13; $^{19}$F NMR (377 MHz, D$_2$O): δ −121.11 to −121.05 (m, 1F); LRMS (ESI): m/z 267 (100%, M+Na$^+$); HPLC: 2.4 min.

Example 14: Compound XIV, Sodium Salt of 2-(4-Hydroxy-3-pentylphenyl)acetic Acid The above compound was prepared by Suzuki coupling of benzyl 2-(4-(benzyloxy)-3-bromophenyl)acetate and (E)-pent-1-enylboronic acid pinacol ester as for example 2; followed by hydrogenation. White solid; melting point 192-195° C.; $^1$H NMR (400 MHz, CD$_3$OD): δ 7.01 (d, J=2.3 Hz, 1H), 6.93 (dd, J=8.2, 2.3 Hz, 1H), 6.64 (d, J=8.2 Hz, 1H), 3.35 (s, 2H), 2.53 (t, J=7.7 Hz, 2H), 1.54-1.61 (m, 2H), 1.30-1.37 (m, 4H), 0.90 (t, J=7.2 Hz, 3H); $^{13}$C NMR (101 MHz, CD$_3$OD): δ 180.25, 153.20, 130.54, 128.80, 128.76, 127.10, 114.49, 44.45, 31.84, 30.10, 29.73, 22.52, 13.31; LRMS (ESI): m/z 245.2 (55%, MH$^+$), 177.4 (100%, M-CO$_2$Na); HPLC: 1.9 min.

Example 15: Compound XV, Sodium Salt of 2-(4-Fluoro-3-pentylphenyl)acetic Acid The above compound was prepared from methyl 2-(3-bromo-4-fluorophenyl)acetate by Suzuki coupling as for example 3 (step 4); followed by hydrogenation, ester hydrolysis and salt formation as for example 1 (Steps 3, 4 & 5). The starting ester was prepared by reaction of 2-(3-bromo-4-fluorophenyl)acetic acid with methanol in the presence of sulfuric acid. White solid; $^1$H NMR (400 MHz, CD$_3$OD): δ 7.16 (dd, J$_{HF}$=7.4 Hz, J$_{HH}$=2.3 Hz, 2H), 7.08 (ddd, J$_{HF}$=5.0 Hz, J$_{HH}$=8.3, 2.31 Hz, 1H), 6.88 (dd, J$_{HF}$=10.1 Hz, J$_{HH}$=8.3 Hz, 111), 3.40 (s, 2H), 2.59 (t, J=7.7 Hz, 2H), 1.55-1.63 (m, 2H), 1.28-1.40 (m, 4H), 0.90 (t, J=7.0 Hz, 3H); $^{13}$C NMR (101 MHz, CD$_3$OD): δ 179.12, 159.88 (d, J$_{CF}$=240.6 Hz), 133.88 (d, J$_{CF}$=3.8 Hz), 131.26 (d, J$_{CF}$=4.6 Hz), 128.78 (d, J$_{CF}$=16.1 Hz), 127.96 (d, J$_{CF}$=8.5 Hz), 114.26 (d, J$_{CF}$=23.1 Hz), 44.38, 31.51, 30.00, 28.76 (d, J$_{CF}$=1.5 Hz), 22.36, 13.18; $^{19}$F NMR (377 MHz, CD$_3$OD): δ −126.45 to −126.40 (m, 1F); LRMS (ESI): m/z 225.2 (M-Na$^+$+2H$^+$); HPLC: 1.9 min.

Example 16: Compound XVI, Sodium Salt of 2-(2-Fluoro-3-pentylphenyl)acetic Acid The above compound was prepared as for compound III, starting with 3-bromo-2-fluorobenzoic acid. White solid; $^1$H NMR (400 MHz, CD$_3$OD): δ 7.13 (ddd, J$_{HF}$=7.0 Hz, J$_{HH}$=7.4, 1.9 Hz, 2H), 7.03 (ddd, J$_{HF}$=7.0 Hz, J$_{HH}$=7.4, 1.9 Hz, 1H), 6.97 (dd, J$_{HH}$=7.4, 7.4 Hz, 1H), 3.51 (d, J$_{HF}$=1.4 Hz, 2H), 2.61 (t, J=7.6 Hz, 2H), 1.56-1.63 (m, 2H), 1.28-1.40 (m, 4H), 0.90 (t, J=6.9 Hz, 3H); $^{13}$C NMR (101 MHz, CD$_3$OD): δ 178.21, 159.70 (d, J$_{CF}$=242.9 Hz), 129.07 (d, J$_{CF}$=4.6 Hz), 128.88, 128.43 (d, J$_{CF}$=5.4 Hz), 125.02 (d, J$_{CF}$=17.7 Hz), 123.31 (d, J$_{CF}$=4.6 Hz), 37.89 (d, J$_{CF}$=3.8 Hz), 31.55, 29.98, 28.91 (d, J$_{CF}$=3.1 Hz), 22.41, 13.26; $^{19}$F NMR (377 MHz, CD$_3$OD): δ −126.09 to −126.05 (m, 1F); LRMS (ESI): m/z 220.0 (M-CO$_2$Na+acetonitrile), 179.4 (M-CO$_2$Na); HPLC: 1.2 min.

Example 17: Compound XVII, Sodium Salt of 3-(4-Hydroxy-3-pentylphenyl)propanoic Acid The above compound was prepared from methyl 3-(4-benzyloxy-3-bromophenyl)propanoate by Suzuki coupling as for example 3 (step 4); followed by hydrogenation, ester hydrolysis and salt formation as for example 1 (Steps 3, 4 & 5). The starting ester was prepared by reaction of 3-(4-benzyloxy-3-bromophenyl)propanoic acid with methyliodide in acetone/water in the presence of sodium carbonate. Tan solid; $^1$H NMR (400 MHz, CD$_3$OD): δ 7.34 (s, 1H), 6.90 (d, J=2.2 Hz, 1H), 6.84 (dd, J=8.0, 2.2 Hz, 1H), 6.61 (d, J=8.0 Hz, 1H), 2.75-2.79 (m, 2H), 2.52 (t, J=7.8 Hz, 2H), 2.35-2.39 (m, 2H), 1.52-1.60 (m, 2H), 1.28-1.41 (m, 4H), 0.90 (t, J=7.0 Hz, 3H); $^{13}$C NMR (101 MHz, CD$_3$OD): δ 181.15, 152.90, 133.23, 129.71, 128.86, 126.10, 114.57, 40.56, 32.06, 31.79, 30.06, 29.71, 22.48, 13.27; LRMS (ESI negative): m/z 235.3 (M-Na); UPLC (System A): 5.2 min. UPLC System A: Mobile phase A=10 mM aqueous ammonium bicarbonate; mobile phase B=water; solid phase=HSS T3 column; gradient=5-100% B in A over 10 minutes.

Example 18: Compound XVIII, Sodium Salt of 2-Oxo-2-(3-pentylphenyl)acetic Acid

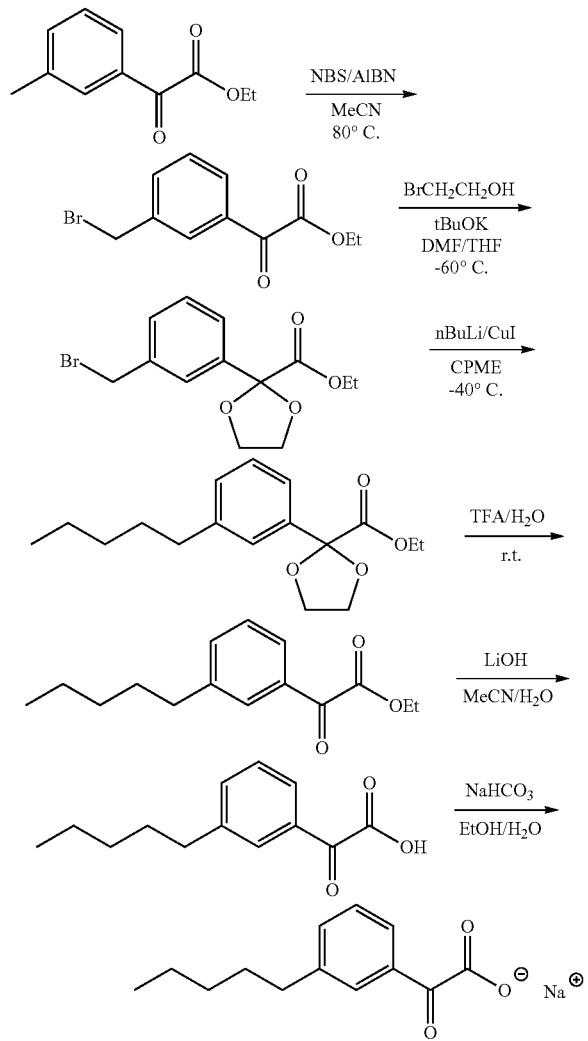

Step 1

A solution of ethyl 2-(3-methylphenyl)-2-oxoacetate (1.06 g, 5.5 mmol) and azobisisobutyronitrile (9 mg, 0.06 mmol) in acetonitrile (3 ml) was heated to 80° C. under nitrogen, and was treated dropwise, over 60 minutes, with a solution of N-bromosuccinimide (1.17 g, 6.6 mmol) and azobisisobutyronitrile (9 mg, 0.06 mmol) in acetonitrile (6 ml). The reaction was stirred at 80° C. for 30 minutes; a further portion of azobisisobutyronitrile (9 mg, 0.06 mmol) was added; and the mixture was stirred at 60° C. for 21.5 hours. The mixture was cooled to room temperature and was diluted with ethyl acetate (50 ml). The solution was washed with water (2×50 ml) and with saturated aqueous sodium chloride (50 ml); then dried over sodium sulfate; filtered and evaporated in vacuo to give the crude product. Purification on a Biotage™ SP1 system (120 g silica cartridge), eluting with 0-10% ethyl acetate in hexanes, gave ethyl 2-(3-(bromomethyl)phenyl)-2-oxoacetate (1.30 g, 95%). $^1$H NMR (400 MHz, CDCl$_3$): δ 7.96-7.97 (m, 1H), 7.84-7.87 (m, 1H), 7.60-7.62 (m, 1H), 7.41 (dd, J=7.7, 7.7 Hz, 1H), 4.45 (s, 2H), 4.39 (q, J=7.2 Hz, 2H), 1.34 (t, J=7.2 Hz, 3H).

Step 2

A solution of ethyl 2-(3-(bromomethyl)phenyl)-2-oxoacetate (0.27 g, 1.0 mmol) and 2-bromoethanol (0.19 g, 1.5 mmol) in N,N-dimethylformamide (0.7 ml) and tetrahydrofuran (0.5 ml) was cooled to −60° C. under argon, and a mixture of N,N-dimethylformamide (0.3 ml) and potassium tert-butoxide solution (1M in tetrahydrofuran; 1.5 ml) was added dropwise over 30 minutes. The reaction was stirred for a further 95 minutes at −60° C., and was then quenched by addition of saturated aqueous ammonium chloride (3 ml). After warming to room temperature, the reaction mixture was diluted with water (10 ml) and with saturated aqueous sodium chloride (10 ml), then extracted with ethyl acetate (5×10 ml). Combined organic extracts were washed with saturated aqueous sodium chloride (3×10 ml); then dried over sodium sulfate; filtered and evaporated in vacuo to give the crude product. Purification on a Biotage™ SP1 system (25 g silica cartridge), eluting with 0-10% ethyl acetate in hexanes, gave ethyl 2-(3-(bromomethyl)phenyl)-1,3-dioxolane-2-carboxylate (0.17 g, 68%). $^1$H NMR (400 MHz, CDCl$_3$): δ 7.62 (dd, J=1.6, 1.6 Hz, 1H), 7.52 (dd, J=7.4, 1.6 Hz, 1H), 7.39 (dd, J=7.8, 1.6 Hz, 1H), 7.33 (dd, J=7.8, 7.4 Hz, 1H), 4.47 (s, 2H), 4.19 (q, J=7.1 Hz, 2H), 4.15-4.20 (m, 2H), 4.05-4.09 (m, 2H), 1.22 (t, J=7.1 Hz, 3H).

Step 3

A solution of n-butyllithium (2.5M in hexanes; 0.53 ml; 1.3 mmol) was added dropwise over 5 minutes to a suspension of copper(I) iodide (0.13 g, 0.66 mmol) in cyclopentyl methyl ether (2.6 ml) at −10° C. under nitrogen. The dark blue mixture was stirred at −10° C. for 15 minutes; was then cooled to −40° C.; and was treated dropwise over 10 minutes with a solution of 2-(3-(bromomethyl)phenyl)-1,3-dioxolane-2-carboxylate (0.17 g, 0.55 mmol) in cyclopentyl methyl ether (0.55 ml). The reaction was allowed to warm to −10° C. over 35 minutes, and was then quenched by addition of 1M aqueous ammonium chloride (1.4 ml). After warming to room temperature, the reaction mixture was partitioned between ethyl acetate (10 ml) and water (15 ml). The organic phase was washed with saturated aqueous sodium chloride (15 ml); then dried over sodium sulfate; filtered and evaporated in vacuo to give ethyl 2-(3-pentylphenyl)-1,3-dioxolane-2-carboxylate (0.1 g, 60%). $^1$H NMR (400 MHz, CDCl$_3$): δ 7.37-7.43 (m, 2H), 7.10-7.30 (m, 2H), 3.95-4.22 (m, 6H), 2.52-2.62 (m, 2H), 1.52-1.64 (m, 2H), 1.28-1.39 (m, 4H), 1.18-1.26 (m, 3H), 0.79-0.93 (m, 3H).

Step 4

A solution of ethyl 2-(3-pentylphenyl)-1,3-dioxolane-2-carboxylate (0.09 g, 0.3 mmol) in trifluoroacetic acid (2 ml) and water (2 ml) was stirred at room temperature overnight. The reaction mixture was diluted with water (20 ml) and ethyl acetate (40 ml), and the pH of the aqueous phase was adjusted to pH 7 by gradual addition of solid sodium bicarbonate (3.0 g). The organic phase was then dried over sodium sulfate; filtered and evaporated in vacuo to give the crude product. Purification on a Biotage™ SP1 system (25 g silica cartridge), eluting with 0-3% ethyl acetate in hexanes, gave ethyl 2-oxo-2-(3-pentylphenyl)acetate (8 mg, 10%). $^1$H NMR (400 MHz, CDCl$_3$): δ 7.71-7.75 (m, 2H), 7.41 (d, J=7.6 Hz, 1H), 7.35 (dd, J=8.0, 7.6 Hz, 1H), 4.39 (q, J=7.2 Hz, 2H), 2.60 (t, J=7.8 Hz, 2H), 1.53-1.60 (m, 2H), 1.36 (t, J=7.2 Hz, 3H), 1.23-1.30 (m, 4H), 0.82 (t, J=7.1 Hz, 3H).

Step 5

A solution of ethyl 2-oxo-2-(3-pentylphenyl)acetate (8 mg, 0.03 mmol) in acetonitrile (0.6 ml) was treated with a 50 mg/ml aqueous solution of lithium hydroxide (0.15 ml, 0.3 mmol) and the reaction was stirred at room temperature overnight. The reaction mixture was quenched with 1M aqueous hydrochloric acid (10 ml), and was extracted with ethyl acetate (10 ml). The organic phase was then washed with saturated aqueous sodium chloride (10 ml); dried over sodium sulfate; filtered and evaporated in vacuo to give 2-oxo-2-(3-pentylphenyl)acetic acid (5.8 mg, 83%). $^1$H NMR (400 MHz, CDCl$_3$): δ 8.17 (d, J=7.6 Hz, 2H), 8.11 (s, 1H), 7.46 (d, J=7.6 Hz, 1H), 7.38 (dd, J=7.6, 7.6 Hz, 1H), 2.61 (t, J=7.7 Hz, 2H), 1.62-1.67 (m, 2H), 1.30-1.37 (m, 4H), 0.83 (t, J=6.9 Hz, 3H).

Step 6

A solution of 2-oxo-2-(3-pentylphenyl)acetic acid (6 mg, 0.02 mmol) in ethanol (0.4 ml) was treated with a 10 mg/ml aqueous solution of sodium bicarbonate (0.19 ml, 0.02 mmol) and the reaction was stirred at room temperature overnight. The reaction mixture was evaporated in vacuo, and the residue was dissolved in water (1 ml); filtered (0.2 micron); and lyophilized to give sodium 2-oxo-2-(3-pentylphenyl)acetate (3.5 mg, 58%). $^1$H NMR (400 MHz, CD$_3$OD): δ 7.77-7.79 (m, 2H), 7.38-7.45 (m, 2H), 2.67 (t, J=7.7 Hz, 2H), 1.60-1.68 (m, 2H), 1.28-1.39 (m, 4H), 0.90 (t, J=7.0 Hz, 3H); $^{13}$C NMR (101 MHz, CD$_3$OD): δ 196.04, 172.87, 143.53, 133.78, 133.76, 129.28, 128.43, 126.94, 35.44, 31.32, 31.06, 22.37, 13.16; LRMS (ESI negative): m/z 218.8 (100%, M-Na$_+$); UPLC (System B): 4.7 min. UPLC System B: Mobile phase A=0.1% aqueous formic acid; mobile phase B=0.1% formic acid in acetonitrile; solid phase=HSS T3 column; gradient=5-100% B in A over 10 minutes.

Example 19: Compound XIX; Sodium Salt of 2-(2-Hydroxy-3-pentylphenyl)acetic Acid

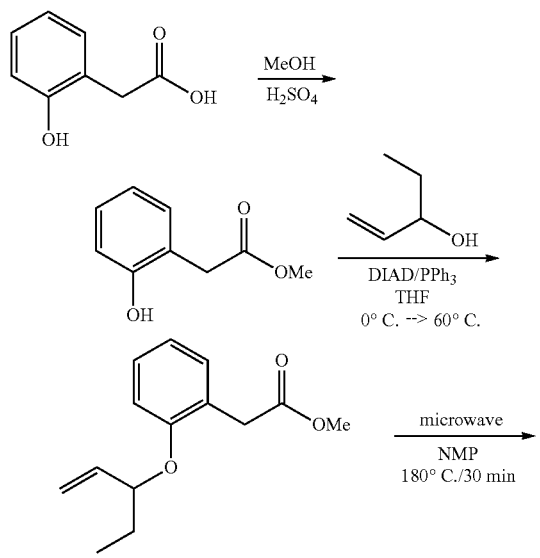

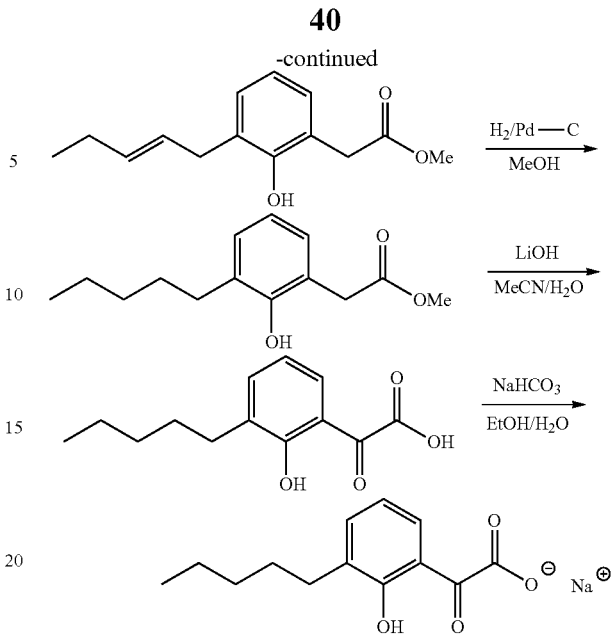

Step 1

A solution of 2-(2-hydroxyphenyl)acetic acid (3.00 g, 19.7 mmol) in methanol (40 ml) was treated with sulfuric acid (0.95 ml, 17.8 mmol) and the reaction was stirred at room temperature for 18 hours. The reaction mixture was diluted with ethyl acetate (250 ml), and the solution was washed with water (2×150 ml) and with saturated aqueous sodium chloride (150 ml); dried over sodium sulfate; filtered and evaporated in vacuo to give the crude product. Recrystallization from hot hexanes gave methyl 2-(2-hydroxyphenyl)acetate (2.83 g, 87%). $^1$H NMR (400 MHz, CDCl$_3$): δ 7.20 (ddd, J=7.7, 7.4, 1.8 Hz, 1H), 7.09-7.11 (m, 1H), 6.94 (dd, J=8.0, 1.2 Hz, 1H), 6.88 (ddd, J=7.4, 7.4, 1.2 Hz, 1H), 3.75 (s, 3H), 3.69 (s, 2H).

Step 2

A solution of methyl 2-(2-hydroxyphenyl)acetate (1.00 g, 6.0 mmol), triphenylphosphine (2.37 g, 9.0 mmol) and pent-1-en-3-ol (0.78 g, 9.0 mmol) in tetrahydrofuran (30 ml) was cooled to 0° C. under nitrogen, and diisopropyl azodicarboxylate (1.86 ml; 9.0 mmol) was added dropwise over 10 minutes. The reaction was then heated to 60° C. for 21.5 hours. Solvent was evaporated in vacuo and the residue was extracted with 5% ethyl acetate in hexanes. The extract was filtered and evaporated in vacuo to give the crude product. Purification on a Biotage™ SP1 system (120 g silica cartridge), eluting with 0-3% ethyl acetate in hexanes, gave methyl 2-(2-(pent-1-en-3-yloxy)phenyl)acetate (0.39 g, 28%). $^1$H NMR (400 MHz, CDCl$_3$): δ 7.21-7.26 (m, 1H), 7.20 (d, J=7.6 Hz, 1-1), 6.91 (ddd, J=7.4, 7.4, 1.0 Hz, 1H), 6.87 (d, J=8.0 Hz, 1H), 5.84 (ddd, J=17.4, 10.7, 6.0 Hz, 1H), 5.26 (d, J=17.4 Hz, 1H), 5.22 (d, J=10.7 Hz, 1H), 4.63 (dt, J=6.0, 6.0 Hz, 2H), 3.70 (s, 3H), 3.68 (s, 2H), 1.71-1.87 (m, 2H), 1.02 (t, J=7.5 Hz, 3H); $^{13}$C NMR (101 MHz, CDCl$_3$): δ 172.58, 156.28, 137.75, 131.19, 128.50, 123.87, 120.52, 116.66, 113.18, 79.76, 52.00, 36.61, 28.71, 9.62.

Step 3

A solution of methyl 2-(2-(pent-1-en-3-yloxy)phenyl)acetate (0.24 g, 1.0 mmol) in N-methyl-2-pyrrolidone (1.0 ml) was irradiated with microwave radiation in a Biotage Initiator at 180° C. for 30 minutes, then for 15 minutes. The solution was diluted with ethyl acetate (25 ml), then washed with water (4×25 ml) and with saturated aqueous sodium chloride (25 ml); dried over sodium sulfate; filtered and evaporated in vacuo to give the crude product. Purification on a Biotage™ SP1 system (40 g silica cartridge), eluting with 0-7% ethyl acetate in hexanes, gave methyl (E)-2-(2-hydroxy-3-(pent-2-enyl)phenyl)acetate (0.89 g, 37%). $^1$H NMR (400 MHz, CDCl$_3$): δ 7.09 (s, 1H), 7.08 (dd, J=7.4, 1.6 Hz, 1H), 7.01 (dd, J=7.6, 1.6 Hz, 1H), 6.85 (dd, J=7.6, 7.4 Hz, 1H), 5.59-5.70 (m, 2H), 3.75 (s, 3H), 3.69 (s, 2H), 3.41 (d, J=4.7 Hz, 2H), 2.04-2.11 (m, 2H), 1.01 (t, J=7.4 Hz, 3H); $^{13}$C NMR (101 MHz, CDCl$_3$): δ 174.31, 153.53, 134.44, 129.86, 129.32, 128.62, 127.13, 121.08, 120.82, 52.79, 37.59, 34.17, 25.77, 13.97.

Step 4

Methyl (E)-2-(2-hydroxy-3-(pent-2-enyl)phenyl)acetate (0.14 g, 0.6 mmol) was hydrogenated as for Compound I, step 3, but using methanol as solvent, to give methyl 2-(2-hydroxy-3-pentylphenyl)acetate (0.11 g, 76%). $^1$H NMR (400 MHz, CDCl$_3$): δ 7.57 (s, 1H), 7.11 (dd, J=7.4, 1.6 Hz, 1H), 6.96 (dd, J=7.4, 1.6 Hz, 1H), 6.84 (dd, J=7.4, 7.4 Hz, 1H), 3.76 (s, 3H), 3.70 (s, 2H), 2.68 (t, J=7.8 Hz, 2H), 1.61-1.67 (m, 2H), 1.36-1.43 (m, 4H), 0.93 (t, J=7.0 Hz, 3H); $^{13}$C NMR (101 MHz, CDCl$_3$): δ 175.01, 153.48, 131.75, 129.98, 128.75, 120.74, 120.60, 53.01, 38.30, 32.10, 30.50, 29.91, 22.87, 14.34.

Step 5

Methyl 2-(2-hydroxy-3-pentylphenyl)acetate (0.11 g, 0.5 mmol) was hydrolysed as for Compound I, step 4, using acetonitrile/water (4:1) as solvents, to give 2-(2-hydroxy-3-pentylphenyl)acetic acid (0.57 g, 57%). $^1$H NMR (400 MHz, CDCl$_3$): δ 8.70 (br s, 1H), 7.09 (dd, J=7.6, 1.6 Hz, 11), 6.98 (dd, J=7.4, 1.6 Hz, 1H), 6.84 (dd, J=7.6, 7.4 Hz, 11H), 3.68 (s, 2H), 2.62 (t, J=7.8 Hz, 2H), 1.57-1.65 (m, 2H), 1.31-1.40 (m, 4H), 0.91 (t, J=7.0 Hz, 3H); $^{13}$C NMR (101 MHz, CDCl$_3$): δ 179.89, 152.79, 130.92, 130.04, 128.98, 121.08, 120.24, 37.74, 32.02, 30.34, 29.78, 22.80, 14.30.

Step 6

2-(2-Hydroxy-3-pentylphenyl)acetic acid (22 mg, 0.098 mmol) was converted to the sodium salt as for Compound I, step 5 to give sodium 2-(2-hydroxy-3-pentylphenyl)acetate (24 mg, 98%). $^1$H NMR (400 MHz, CD$_3$OD): δ 6.91 (dd, J=7.5, 1.6 Hz, 1H), 6.87 (dd, J=7.5, 1.6 Hz, 1H), 6.66 (dd, J=7.5, 7.5 Hz, 1H), 3.49 (s, 2H), 2.59 (t, J=7.7 Hz, 2H), 1.55-1.62 (m, 2H), 1.28-1.38 (m, 4H), 0.90 (t, J=7.0 Hz, 3H); $^{13}$C NMR (101 MHz, CD$_3$OD): δ 180.26, 154.27, 130.75, 128.21, 127.90, 124.24, 119.23, 42.91, 31.83, 30.21, 29.82, 22.51, 13.29; LRMS (ESI negative): m/z 220.8 (100%, M-Na$^+$); UPLC (System A): 5.0 min. UPLC System A: Mobile phase A=10 mM aqueous ammonium formate; mobile phase B=acetonitrile; solid phase=HSS T3 column; gradient=5-100% B in A over 10 minutes.

Example 20: Compound XX; Sodium Salt of 2-(2-Benzyl-3-hydroxy-5-pentylphenyl)acetic Acid

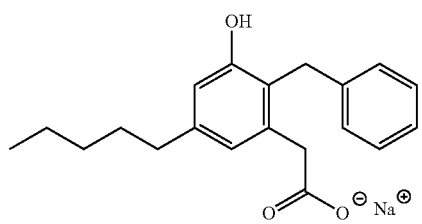 [SMILES: CCCCCc1cc(O)c(Cc2ccccc2)c(CC(=O)[O-])c1 ; [Na+]]

The above compound was prepared as for example 2 (as for compound XI) from methyl (E)-2-(2-benzyl-3-(benzyloxy)-5-(pent-1-enyl)phenyl)acetate. $^1$H NMR (400 MHz, CD$_3$OD): □7.13-7.18 (m, 4H), 7.03-7.09 (m, 1H), 6.63 (d, J=1.6 Hz, 1H), 6.57 (d, J=1.6 Hz, 1H), 4.07 (s, 2H), 3.37 (s, 2H), 2.48 (t, J=7.7 Hz, 2H), 1.56-1.64 (m, 2H), 1.28-1.39 (m, 4H), 0.90 (t, J=6.9 Hz, 3H); $^{13}$C NMR (101 MHz, CD$_3$OD): □ 179.51, 155.24, 141.67, 141.46, 138.05, 128.22, 127.83, 125.14, 123.51, 121.79, 113.06, 42.65, 35.61, 31.66, 31.13, 31.10, 22.49, 13.33; LRMS (ESI+): m/z 312.9 (90%, M Na$^+$+2H$^+$); UPLC (System A): 6.0 min. (UPLC System A: Mobile phase A=10 mM aqueous ammonium formate; mobile phase B=acetonitrile; solid phase=HSS T3 column; gradient=5-100% B in A over 10 minutes.

Example 21: Effect of Compound I on the Bleomycin-Induced Pulmonary Fibrosis Mouse Model Intratracheal instillation of the anticancer drug bleomycin into the mouse results in acute inflammation followed by a chronic fibrotic response. Therefore, evaluation of candidate antifibrotic drugs such as Compound I can be undertaken by treatment of the mice at appropriate time points and histologic, biochemical and cellular readouts may be used to monitor candidate drug efficacy in this model.

Male C57BL6 mice are administered intratracheal instillation of bleomycin sulphate (0.025 U) at day 0, randomized and administered Compound I (oral administration, 100 mg/kg and 200 mg/kg) on day 7 to day 20.

Figure 1:
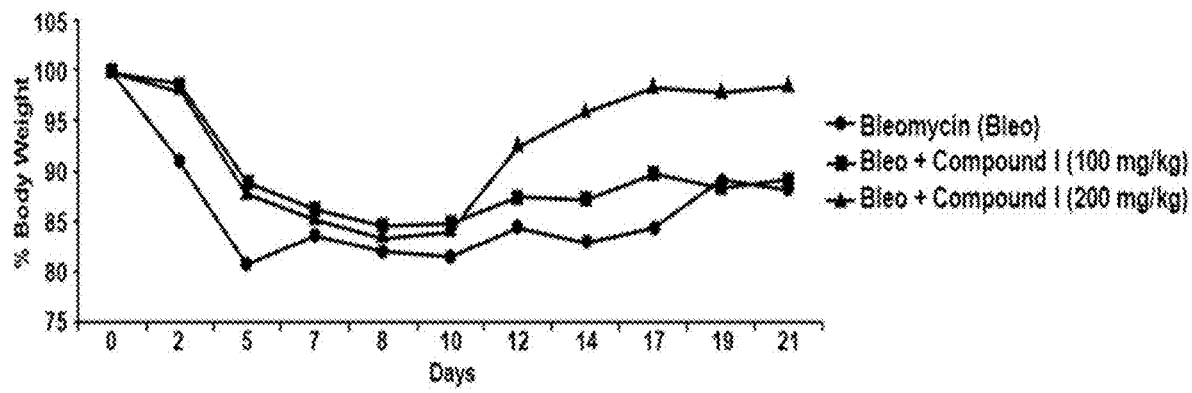
FIG. 1 shows the recovery of the body weight loss in bleomycin-induced pulmonary fibrosis mouse model following oral treatment with Compound I at a dose of 100 and 200 mg/kg compare to oral treatment with vehicle (water) (Bleo).

Intratracheal instillation of bleomycin induced a significant loss in body weight from day 5 to day 21. Oral treatment with 200 mg/kg of Compound I reduced this body weight loss (FIG. 1).

Figure 2:
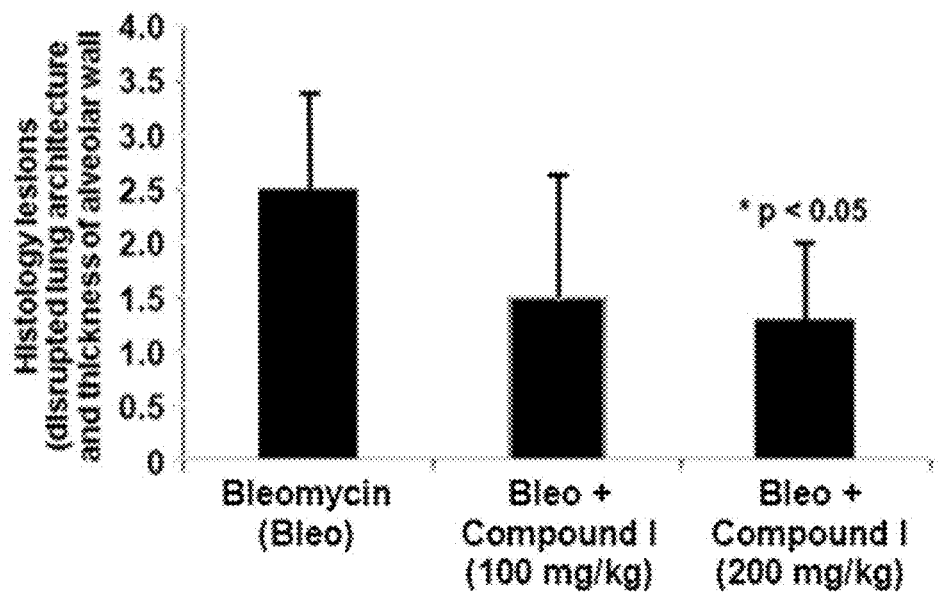
FIG. 2 shows an evaluation using HEP (Hemalun with Eosin/Ploxine) and Masson's trichrome staining of histologic samples of lungs from bleomycin-induced pulmonary fibrosis mouse model following oral treatment with Compound I at a dose of 100 and 200 mg/kg or oral treatment with vehicle (water) (Bleo) showing significant reduction of lesions.

Histological examination of lungs from these animals revealed interesting differences. As illustrated in FIG. 2, lungs from Compound I-treated animals showed a significant reduction of lesions. Lesions score was evaluated using HEP (Hemalun with Eosin/Ploxine) and Masson's trichrome staining. Lesions score was recorded as 1) Consolidation as shown by disrupted lung architecture (cellular and/or fibrosis) and 2) Alveolar wall as shown by thickness and shrinking outside of consolidated area. Treatment with Compound I reduced histological lesions in a dose-dependent manner.

Figure 3:
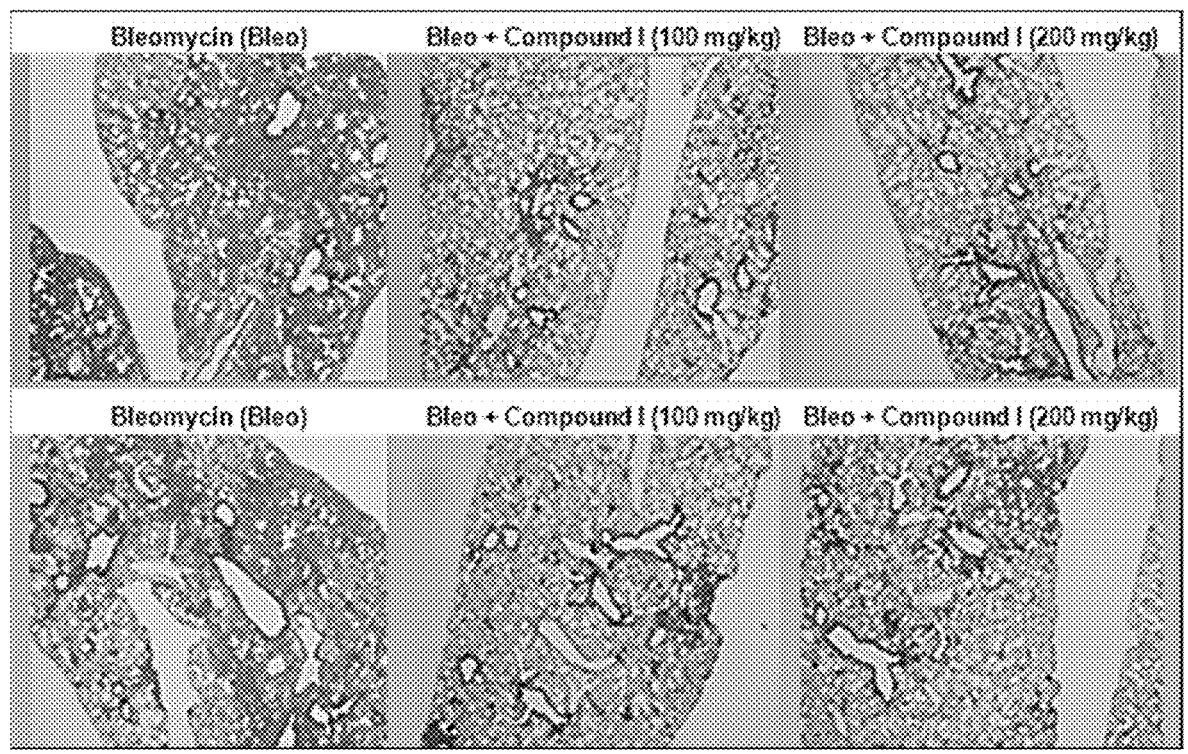
FIG. 3 presents photomicrographs of lung tissue from bleomycin-induced pulmonary fibrosis mouse model following oral treatment with Compound I at a dose of 100 and 200 mg/kg or oral treatment with vehicle (water) (Bleo).
Figure 4:
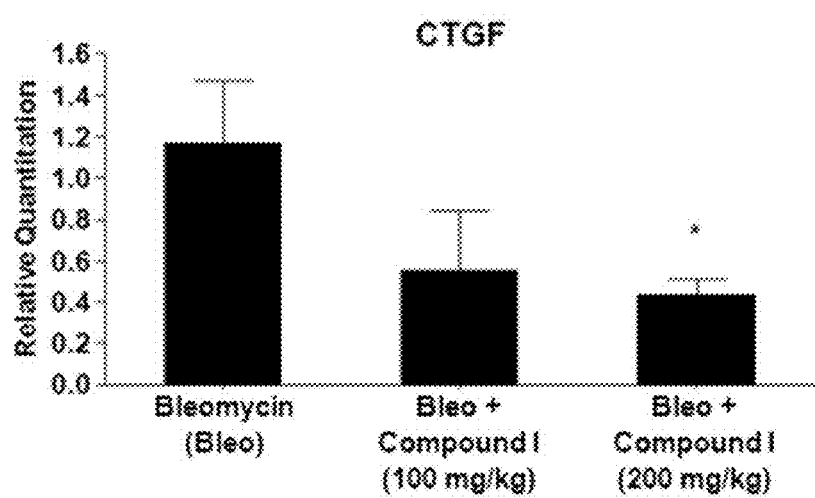
FIG. 4 represents the CTGF content of lung tissue from bleomycin-induced pulmonary fibrosis mouse model following oral treatment with Compound I at a dose of 100 and 200 mg/kg or oral treatment with vehicle (water) (Bleo).

FIG. 3 presents photomicrographs from lung tissue of bleomycin-induced pulmonary fibrosis. It is evident that treatment with Compound I reduced lesions and fibrosis in lungs. Further analysis of the lung tissue was undertaken. CTGF, collagen 1 and IL-23p19 mRNA expression was quantified by real-time PCR. Our results show that oral administration of Compound I significantly decreased the expression of these inflammatory and fibrotic markers in lungs as shown in FIGS. 4, 5 and 6, respectively.

Overall, our results suggest that treatment with Compound 1 may be beneficial to prevent the progression, or induce the regression of lung injury that results from the clinical use of anti-cancer chemotherapeutic agents such as bleomycin. Furthermore, our results suggest that treatment with Compound I may be beneficial to prevent the progression of or treat pulmonary fibrosis, including idiopathic pulmonary fibrosis (IPF).

Example 22: Effect of Compound I and Pirfenidone on the Bleomycin-Induced Pulmonary Fibrosis Mouse Model Pirfenidone demonstrated sufficient drug efficacy for the treatment of IPF in clinical trials to procure approval in Europe and Canada. It was therefore evaluated side-by-side with Compound I in the bleomycin-induced pulmonary fibrosis mouse model by the same protocol described in Example 4 above. Compound I (200 mg/kg) and pirfenidone (400 mg/kg) were orally administered either alone or in combination.

Compound I and pirfenidone were solubilized in PBS. In the combination therapy, pirfenidone was solubilized in a solution of Compound I. No toxicity was reported with Compound I treatment. Treatment with pirfenidone induced severe vertigo that was reduced in the combination therapy (Table 1).

TABLE 1

Toxicity related to drug. Compound I and pirfenidone were solubilized in PBS. In the combination therapy, pirfenidone was solubilized in a solution of Compound I.

| | |
|---|---|
| Compound I (200 mg/kg) | No toxicity observed |
| Pirfenidone (400 mg/kg) | Vertigo++++ |
| Compound I + pirfenidone | Vertigo++ |

Histological examination of lungs from these animals revealed interesting differences. As illustrated in FIG. 7, the percentage of lungs affected by bleomycin was lower in animals treated with Compound I and the combination therapy (Compound I and pirfenidone).

Lesions score was evaluated using HEP (Hemalun with Eosin/Ploxine) and Masson's trichrome staining and recorded as 1) Consolidation as shown by disrupted lung architecture (cellular and/or fibrosis), and 2) Alveolar wall as shown by thickness and shrinking outside of consolidated area. As presented in FIG. 8, treatment with Compound I significantly reduced histological lesions compared to pirfenidone which demonstrated no reduction of fibrosis at the histological level. Combination of Compound I and pirfenidone reduced further histological lesions.

The lesions score as determined by the percentage of leukocyte infiltration (inflammatory zone) multiplied by the percentage of collagen found in the leukocyte infiltrate was quantified by histomorphometry using Masson's trichrome staining. Bleomycin induces a strong increase in the percentage of collagen in the leukocyte infiltration and this is significantly reduced with the oral treatment with Compound I as shown FIG. 9.

FIG. 10 presents photomicrographs from lung tissue of bleomycin-induced pulmonary fibrosis stained with HEP. It is evident that treatment with Compound I reduced lesions and fibrosis in lungs as observed by a reduction of disrupted lung architecture and interstitial thickness of alveolar wall and cellular infiltration. Pirfenidone alone has no effect.

Visual grading of pulmonary fibrosis was also determined according to Ashcroft's score. Briefly, the entire fields of each lung section were read by a blinded examiner, and each field was visually graded from 0 to 8. Criteria for grading lung fibrosis were as follows: Grade 0=normal lung; Grade 1=minimal fibrous thickening of alveolar or bronchiolar walls; Grade 3=moderate thickening of walls without obvious damage to lung architecture; Grade 5=increased fibrosis with definitive damage to lung structure and formation of fibrous bands or small fibrous masses; Grade 7=severe distortion of structure and large fibrous area; Grade 8=total fibrous obliteration of lung fields.

Masson's stain showed that alveolar spaces were widened and filled with collagen fibers, indicating proliferative fibroblastic lesions in bleomycin-induced lung fibrosis (FIG. 11) that were reduced with oral treatment with Compound I or combination of Compound I and pirfenidone. Pirfenidone alone demonstrated weak activity when graded according to Ashcroft's method.

IPF is a chronic interstitial lung disease which results in end-stage fibrosis. The pathogenesis is believed to be related to a dysregulation in cross-talk between inflammatory and structural cells, mediated by various cytokines, chemokines and growth factors, which are responsible for the maintenance of tissue homeostasis and which coordinate the response to injury. Amongst many cytokines tested, IL-1-β, IL-17 and IL-23 demonstrate marked inflammation, tissue damage and chronic fibrosis; tumor necrosis factor-α (TNF-α) and IL-6 induce inflammation and mild fibrosis; IL-4 and IL-13 promote fibrocytes differentiation and fibrosis; TGF-β and CTGF cause minor inflammation but marked progressive chronic fibrosis. In fact, transforming growth factor (TGF)-β1 is one of the main profibrogenic cytokines involved in the pathogenesis of lung fibrosis. It induces fibroblast differentiation into myofibroblasts, which produce high levels of collagen and concomitantly loss of lung elasticity and reduction of the respiratory function.

In order to determine the effect of Compound I on pulmonary fibrosis, further analysis of the lung tissue was undertaken. TGF-β, CTGF, IL-23 and IL-6 mRNA expression was quantified by real-time PCR. Our results show that oral administration of Compound I and combination therapy significantly decreased the expression of these inflammatory and fibrotic markers in lungs as shown in FIGS. 12, 13, 14 and 15, respectively. Oral administration of pirfenidone had no effect on CTGF mRNA expression but decreased TGF-β, IL-23 and IL-6 mRNA expression.

IPF is characterized by exaggerated fibroblast proliferation and accumulation of collagens and fibronectin. Altered fibronectin expression, degradation, and organization have been associated with lung fibrosis. Our results show that intratracheal aspiration of bleomycin increases both collagen 1 and fibronectin (FN-1) mRNA expression. Oral treatment with Compound I, pirfenidone and combination therapy induced a significant reduction of these two fibrotic markers to the control level (FIGS. 16 and 17). In addition, treatment with Compound I induced a weak reduction of collagen 3 mRNA expression, while pirfenidone treatment has no effect. However, the combination therapy significantly suppressed collagen 3 expression close to the level of control (FIG. 18).

Example 23: Effect of Compound I on the CCl₄-Induced Liver Fibrosis Mouse Model

Hepatic fibrosis is an outcome of many chronic liver diseases, including hepatitis B virus, hepatitis C virus, alcoholic liver disease, non-alcoholic steatohepatitis and diverse chronic intoxication. It was thus desired to evaluate the effect of Compound I on murine CCl₄-induced liver fibrosis. Intoxication with CCl₄ results in hepatocyte damage, necrosis, inflammation, and fibrosis, which spreads to link the vascular structures that feed into and drain the hepatic sinusoid (the portal tract and central vein radicle, respectively), and over 8-30 weeks results in the development of fibrosis to hepatocellular carcinoma. Therefore, evaluation of candidate antifibrotic drugs such as Compound I can be undertaken by treatment of the mice at appropriate time points and histologic, biochemical and cellular readouts may be used to monitor candidate drug efficacy in this model.

CCl4 (10% in corn oil, 2 ml/kg) was intraperitoneally injected twice a week for 16 weeks in male C57BL/6.

Compound I (200 mg/kg) was orally administered every day from day 1 to day 113. Mice were euthanasized and histology and liver fibrotic markers were analyzed.

To determine if Compound I has an effect on liver fibrosis, hydroxyproline level was used to measure the collagen content in the tissue, which is indicative of liver fibrosis. Oral treatment with Compound I induced a significant reduction of hydroxyproline level in liver (FIG. 19).

The reduction of collagen level in liver tissue was also observed in histological micrographs using the Masson's Trichrome staining. FIG. 20, Compound I induced a significant reduction of collagen score.

The Masson's trichrome stain the cytoplasm, keratin, muscle fibers and intracellular fibers in red colour; nuclei in black colour and collagen (fibrous tissue) in blue color. As illustrated in FIG. 21, all control mice revealed a normal distribution of collagen. Extensive collagen deposition and bridging fibrosis were evident in CCl4-induced animals while significant reduction of collagen deposition and bridging formation between portal-portal of portal-central canal was observed in Compound I treated animals.

Another experiment has been performed with Compound 1 and Compound V where CCL4 (10% in olive oil, 2 ml/kg) was intraperitoneally injected twice a week for 8 weeks in male C57BL/6. Compound I and compound V were orally administered (100 and 200 mg/kg) every day from day 1 to day 58. Mice were euthanasized and collagen content (marker of fibrosis) in the liver was quantified by histomorphometry using Masson's trichrome staining. Oral treatment with Compound 1 and Compound V induced a significant reduction of collagen content in liver (FIG. 22).

Example 24: Antifibrotic Effect of Compound on Skin Fibrosis

The effect of Compound of the invention on skin fibrosis was studied using normal human dermal fibroblasts (NHDF).

In vitro analysis was undertaken to determine the effect of Compound I on TGF-β-induced CTGF, collagen 1 and α-SMA (markers of fibrosis) on normal human dermal fibroblasts (NHIDF). Expression of the profibrotic (CTGF) and fibrotic markers (collagen 1 and α-SMA) were determined by quantitative real-time PCR. As shown in FIGS. 23, 24 and 25, TGF-β (5 ng/ml) induces an upregulation of CTGF, collagen 1 and α-SMA transcript expression which is inhibited by Compound I (500 μM). Also, treatment of cells with Compound I alone resulted in a decreased basal expression of CTGF, collagen 1 and α-SMA.

Myofibroblasts are terminally differentiated cells derived from fibroblasts, epithelial and mesenchymal stem/stromal (fibrocytes) cells that play an important role in tissue fibrosis via increased matrix synthesis such as collagen. α-SMA is a well-known marker of myofibroblast. Our results indicate that Compound I inhibits fibroblast differentiation as demonstrated by 90 percent inhibition of α-SMA in TGF-β induced fibroblasts.

Myofibroblasts also exhibit an enhanced migratory phenotype (Suganuma et al. 1995) and are capable of releasing numerous pro-fibrotic mediators. The next experiments (scratch assay, invasion/migration) were designed to determine the effect of Compound I on EGF-stimulated normal human dermal fibroblasts (NHDF). In summary, mitomycin-treated NHDF were stimulated with EGF and incubated in the presence or absence (control) of Compound I (0.5 mM). EGF stimulated fibroblast invasion into the scratch which is inhibited by Compound I (FIG. 26).

Example 25: Antifibrotic Effect of Compound on Fibrotic Marker on Fibroblast and Epithelial Cells CTGF, collagen 1 and α-SMA are fibrotic markers produced by activated fibroblasts and by epithelial cells that undergo to epithelial-mesenchymal transition (EMT). TGF-β was used to induce EMT in HK-2 cells (epithelial cells) and also to induce activated fibroblasts (normal human dermal fibroblast (NHDF) and rat fibroblast (NRK-49F) to secrete collagen and express strongly α-SMA. Expression of fibrotic markers (collagen 1 and α-SMA) were determined by quantitative real-time PCR. As shown in Table 2, compound of the invention inhibited collagen 1 and α-SMA in both epithelial cells and fibroblasts.

Table 2: Percentage of inhibition of collagen in epithelial cells (HK2 cells) and fibroblasts (NHDF) and percentage of inhibition of α-SMA in fibroblasts (NRK-49F and NHDF) has been determined for several compounds according the invention. In all cases, the mRNA of collagen and α-SMA has been measured, and the inhibition was evaluated in presence of a respective concentration of the tested compound. The compounds have been tested at different concentrations [mM]. All compounds reduce the expression of collagen and α-SMA in HK-2, NHDF and NRK-49F cells.

TABLE 2

| | Collagen | | α-SMA | |
|---|---|---|---|---|
| Compound | HK-2 cells % inhibition [mM] | NHDF cells % inhibition [mM] | NRK-49F cells % inhibition [mM] | NHDF cells % inhibition [mM] |
| Compound I | 86% [0.5] | 65% [0.5] | 85% [0.5] | 99% [0-5] |
| Compound II | 43% [0.5] | 40% [0.5] | 66% [0.5] | |
| Compound III | 100% [0.5] | | 100% [0.25] | |
| Compound IV | n.d. | | 64% [0.5] | |
| Compound V | 100% [0.5] | 100% [0.5] | 100% [0.5] | 100% [0.5] |
| Compound VI | n.d. | | 90% [0.125] | |
| Compound VII | n.d. | | 100% [0.25] | |
| Compound VIII | n.d. | | 86% [0.25] | |
| Compound IX | n.d. | | 82% [0.5] | |
| Compound X | n.d. | | 46% [0.1] | |
| Compound XI | n.d. | | 80% [0.1] | |
| Compound XII | n.d. | | 49% [0.1] | |
| Compound XIII | n.d. | | 84% [0.5] | |
| Compound XIV | 72% [0.5] | 26% [0.5] | 92% [0.5] | |

TABLE 2-continued

|  | Collagen | | α-SMA | |
| --- | --- | --- | --- | --- |
| Compound | HK-2 cells % inhibition [mM] | NHDF cells % inhibition [mM] | NRK-49F cells % inhibition [mM] | NHDF cells % inhibition [mM] |
| Compound XV | 100% [0.5] | | 100% [0.5] | |
| Compound XVI | 100% [0.5] | | 100% [0.25] | |
| Compound XVII | 0% [0.25] | | 66% [0.5] | |
| Compound XVIII | n.d. | | 100% [0.25] | |
| Compound XIX | 100% [0.25] | | 100% [0.25] | |
| Compound XX | 73% [0.125] | | 95% [0.0625] | | n.d. means not determined

Example 26: Effect of Compound I on Heart Fibrosis Mouse Model

Implantation of a femoral catheter increases the presence of heart fibrosis in our 5/6 nephrectomized (5/6-Nx) model and it was used to assess the effect of Compound I on heart fibrosis. In summary, male 6-week old Sprague-Dawley rats were subjected to 5/6-Nx or sham operations. Briefly, two-thirds of the left kidney was removed on day 0 followed by the right total nephrectomy on day 7. A catheter was implanted via the femoral vein on day 7. Sham operated rats underwent exposition of the kidneys and removal of the perirenal fat and were used as controls. Animals that underwent the sham operation were treated with vehicle (water) and were used as controls. On day 21, rats were randomized based on their glomerular filtration rate (GFR) results. 5/6-Nx animals were treated with three times a week intravenous administration of Compound I (10 mg/kg), or with daily oral administration with Compound I (200 mg/kg). Heart fibrosis was determined by the measurement of hydroxyproline (collagen content) and by histological evaluation (HPE and Masson's trichrome staining).

As mentioned, implantation of catheter for intravenous administration of compounds in catheterized 5/6 nephrectomized animals is inducing heart fibrosis compare to oral treatment (no catheter). Oral treatment is identified herein with the expression "po" that means "per os"; intravenous administration is identified with the expression "iv" for "intravenous". As exemplified in FIG. 27, 5/6-Nx rats have weak heart lesions. However, implantation of a catheter induced a significant increase (4 times) of heart lesions (fibrosis, necrosis and inflammation).

It can see that treatment with intravenous Compound I reduces significantly ($p<0.05$) total heart lesions as shown in FIG. 28 which include a significant reduction of inflammation as reported in FIG. 29 and a significant reduction of necrosis as reported in FIG. 30.

Further analysis was undertaken to determine the heart collagen content by measuring hydroxylproline, which is detected specifically in collagen. Hydroxyproline content (collagen) is significantly increased in heart of nephrectomized rats, as reported in FIG. 31. Both, intravenous and oral treatments with Compound I, induce a significant reduction of hydroxyproline content (FIG. 30).

This reduction in hydroxyproline (collagen) content correlates with the histological photomicrographs of heart stained with Masson's trichrome staining which is used to stain collagen (blue). FIGS. 32 and 33 show photomicrographs of the heart of a representative animal at a magnification view of 40× and 100× respectively, where the Compound I was administered orally, in comparison with a nephrectomised animal that did not received Compound I. FIG. 34 shows photomicrographs of the heart of a representative animal at a magnification view of 40×, where the Compound I was administered intravenously, in comparison with a nephrectomised animal that did not received Compound I. FIGS. 32, 33 and 34 are photomicrographs of the heart of animals showing similar serum creatinine level. In all photomicrographs, it is evident that intravenous and oral treatment with Compound I reduces fibrosis (blue-colored collagen deposition).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A kit comprising a pharmaceutical composition for slowing progression of, and/or treating, a fibrotic disease in a subject in need thereof, wherein said pharmaceutical composition is formulated for treating pulmonary fibrosis, liver fibrosis, skin fibrosis or cardiac fibrosis, and wherein said pharmaceutical composition comprises a pharmaceutically-acceptable carrier and a compound represented by the formula:

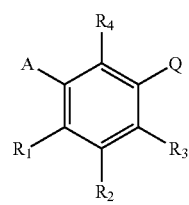

or a pharmaceutically acceptable salt thereof, wherein
A is C5 alkyl, C6 alkyl, C5 alkenyl, C6 alkenyl, C(O)—(CH$_2$)n-CH$_3$ or CH(OH)—(CH$_2$)n-CH3 wherein n is 3 or 4;

R₁ is H, OH or F;
R₂ is H, OH, F or CH₂—OH;
R₃ is CH₂Ph;
R₄ is H, OH or F;
Q is
1) (CH₂)mC(O)OH wherein m is 1 or 2,
2) CH(CH₃)C(O)OH,
3) C(CH₃)₂C(O)OH,
4) CH(F)—C(O)OH,
5) CF₂—C(O)OH, or
6) C(O)—C(O)OH;

wherein the kit further comprises instructions for administering a therapeutically effective amount of the compound to the subject suffering from said fibrotic disease; and wherein the fibrotic disease is pulmonary fibrosis, liver fibrosis, skin fibrosis or cardiac fibrosis.

2. The kit of claim 1, wherein the therapeutically effective amount and the instructions are for administration to a human subject.

3. The kit of claim 1, comprising instructions for administering between about 1 to about 50 mg/kg of the compound daily and orally to a human subject.

4. The kit of claim 1, wherein the pharmaceutical composition comprises between about 0.01 to about 10% (w/w) of the compound, and wherein the kit comprises instructions for daily and topical administration to a human subject, for the treatment of skin fibrosis.

5. The kit of claim 1, wherein the fibrotic disease is pulmonary fibrosis.

6. The kit of claim 1, wherein the fibrotic disease is liver fibrosis.

7. The kit of claim 1, wherein the fibrotic disease is skin fibrosis.

8. The kit of claim 1, wherein the fibrotic disease is cardiac fibrosis.

9. The kit of claim 4, wherein the concentration of the compound is between about 0.1 to about 5% (w/w).

10. The kit of claim 9, wherein the concentration of the compound is between about 1 to about 5% (w/w).

11. The kit according to claim 1, wherein the pharmaceutically acceptable salt of said compound is sodium, potassium, lithium, ammonium, calcium, magnesium, manganese, zinc, iron, or copper.

12. The kit of claim 11, wherein the pharmaceutically acceptable salt of said compound is sodium.

13. The kit of claim 1, wherein the compound is one of the following compounds:

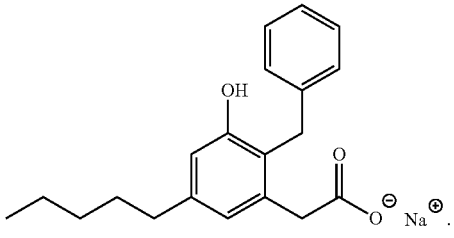

Compound XX

14. A method for slowing progression of, and/or treating, a fibrotic disease in a subject in need thereof, wherein the method comprises providing the kit of claim 1, and administering to the subject the pharmaceutical composition.

15. The method of claim 14, wherein the fibrotic disease is pulmonary fibrosis, liver fibrosis, skin fibrosis or cardiac fibrosis.

16. The method of claim 15, wherein the pulmonary fibrosis is idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, pulmonary hypertension, or chronic obstructive pulmonary disease.

17. The method of claim 15, wherein the liver fibrosis is resulting from a chronic liver disease, hepatitis B virus infection, hepatitis C virus infection, hepatitis D virus infection, schistosomiasis, alcoholic liver disease or non-alcoholic steatohepatitis, obesity, diabetes, protein malnutrition, coronary artery disease, auto-immune hepatitis, cystic fibrosis, alpha-1-antitrypsin deficiency, primary biliary cirrhosis, drug reaction or exposure to toxins.

18. The method of claim 15, wherein the skin fibrosis is scarring, hypertrophic scarring, keloid scarring, dermal fibrotic disorder, wound healing, delayed wound healing, psoriasis or scleroderma.

19. The method of claim 15, wherein the cardiac fibrosis is cardiomyopathy or congestive heart failure.

* * * * *

UNITED STATES PATENT AND TRADEMARK OFFICE
CERTIFICATE OF CORRECTION

PATENT NO. : 11,267,779 B2
APPLICATION NO. : 16/580747
DATED : March 8, 2022
INVENTOR(S) : Lyne Gagnon et al.

Page 1 of 2

It is certified that error appears in the above-identified patent and that said Letters Patent is hereby corrected as shown below:

In the Specification

Column 14,
Line 67, "(NHIDF)" should read --(NHDF)--.

Column 28,
Lines 44-45, "(0.2 m)" should read --(0.2 μm)--.

Column 32,
Line 7, "= 7.7 Iz)," should read --=7.7 Hz),--.

Column 35,
Line 25, "(m, 61H)," should read --(m, 6H),--.

Column 39,
Line 35, "M- Na+);" should read --M- Na$^+$);--.

Column 40,
Lines 12-16, " 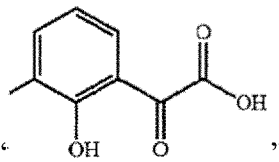 " should read -- 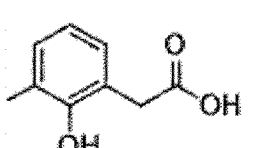 --.

Column 40,
Lines 17-22, " 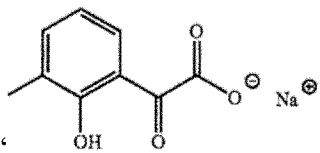 " should read -- 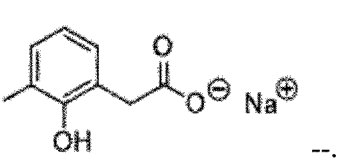 --.

Signed and Sealed this
Twenty-seventh Day of December, 2022

Katherine Kelly Vidal
*Director of the United States Patent and Trademark Office*

Column 42,
Line 9, "M Na$^+$" should read --M - Na$^+$--.

Column 45,
Line 42, "(NHIDF)" should read --(NHDF)--.